United States Patent
Parvulescu et al.

(10) Patent No.: US 9,296,714 B2
(45) Date of Patent: Mar. 29, 2016

(54) MICROPOWDER AND MOLDING CONTAINING A ZEOLITIC MATERIAL CONTAINING TI AND ZN

(71) Applicant: BASF SE, Ludwigshafen (DE)

(72) Inventors: Andrei-Nicolae Parvulescu, Heidelberg (DE); Ulrich Mueller, Neustadt (DE); Joaquim Henrique Teles, Waldsee (DE); Bianca Seelig, Cologne (DE); Philip Kampe, Antwerp (BE); Markus Weber, Limburgerhof (DE); Robert Bayer, Sinsheim (DE); Karsten Seidel, Mannheim (DE); Peter Resch, Hettenleidelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/759,663

(22) Filed: Feb. 5, 2013

(65) Prior Publication Data

US 2013/0204018 A1 Aug. 8, 2013

Related U.S. Application Data

(60) Provisional application No. 61/595,704, filed on Feb. 7, 2012.

(51) Int. Cl.
| | | |
|---|---|---|
| *C01B 39/12* | (2006.01) | |
| *B01J 29/70* | (2006.01) | |
| *C07D 301/12* | (2006.01) | |
| *B01J 29/04* | (2006.01) | |
| *B01J 35/00* | (2006.01) | |
| *B01J 35/02* | (2006.01) | |
| *B01J 37/00* | (2006.01) | |
| *C01B 37/00* | (2006.01) | |
| *C01B 39/02* | (2006.01) | |
| *C01B 39/06* | (2006.01) | |
| *B01J 29/89* | (2006.01) | |

(52) U.S. Cl.
CPC ............. *C07D 301/12* (2013.01); *B01J 29/041* (2013.01); *B01J 29/7088* (2013.01); *B01J 29/89* (2013.01); *B01J 35/002* (2013.01); *B01J 35/023* (2013.01); *B01J 37/0009* (2013.01); *B01J 37/0045* (2013.01); *C01B 37/005* (2013.01); *C01B 39/026* (2013.01); *C01B 39/065* (2013.01); *C01B 39/12* (2013.01); *B01J 2229/18* (2013.01); *B01J 2229/37* (2013.01); *B01J 2229/42* (2013.01)

(58) Field of Classification Search
CPC ...... B01J 29/041; B01J 23/52; B01J 37/0009; B01J 29/061; B01J 29/7007; B01J 29/7088; B01J 29/89; B01J 2229/18; B01J 2229/37; B01J 2229/42; C07D 303/48; C07D 301/06; C07D 301/12; C01B 39/026; C01B 39/065; C01B 39/12

See application file for complete search history.

(56) References Cited

U.S. PATENT DOCUMENTS

| | | | |
|---|---|---|---|
| 6,114,552 A | 9/2000 | Han et al. | |
| 6,114,587 A * | 9/2000 | Climent Olmedo et al. | . 568/433 |
| 6,759,540 B2 | 7/2004 | Oguchi et al. | |
| 7,273,826 B2 | 9/2007 | Miller et al. | |
| 7,476,770 B2 | 1/2009 | Miller et al. | |
| 7,608,728 B2 | 10/2009 | Mueller et al. | |
| 2007/0276166 A1* | 11/2007 | Miller et al. | 568/959 |
| 2012/0148487 A1* | 6/2012 | Katz et al. | 423/718 |

FOREIGN PATENT DOCUMENTS

| | | | |
|---|---|---|---|
| JP | 2008-200553 | | 9/2008 |
| JP | 2008200553 | * | 9/2008 |

OTHER PUBLICATIONS

"Framework Type MWW" IZA p. 1-2 1997.*
Framework Type MWW IZA p. 1-2 1997.*
Peng Wu, et al., "Hydrothermal Synthesis of a Novel Titanosilicate with MWW Topology", Chemisty Letters, 2000, pp. 774-775.
Peng Wu, et al., "A Novel Titanosilicate with MWW Structure. I. Hydrothermal Synthesis, Elimination of Extraframework Titanium, and Characterizations", J. PHYS. CHEM. B, vol. 105, No. 15, 2001, pp. 2897-2905.

* cited by examiner

*Primary Examiner* — David M Brunsman
(74) *Attorney, Agent, or Firm* — Marshall, Gerstein & Borun LLP

(57) ABSTRACT

The present invention relates to a micropowder, wherein the particles of the micropowder have a Dv10 value of at least 2 micrometer and the micropowder comprises mesopores which have an average pore diameter in the range of from 2 to 50 nm and comprise, based on the weight of the micropowder, at least 95 weight-% of a microporous aluminum-free zeolitic material of structure type MWW containing titanium and zinc.

37 Claims, 27 Drawing Sheets

200 micrometer

MICROPOWDER AND MOLDING CONTAINING A ZEOLITIC MATERIAL CONTAINING TI AND ZN

The present invention relates to a micropowder, the particles of which have a Dv10 value of at least 2 micrometer, wherein said micropowder comprises mesopores having an average pore diameter in the range of from 2 to 50 nm and comprise, based on the weight of the micropowder, at least 95 weight-% of a microporous aluminum-free zeolitic material of structure type MWW containing titanium and zinc. Further, the present invention relates to a molding which comprises said micropowder, wherein the molding preferably further comprises at least one binder, in particular a silica binder. Yet further, the present invention relates to a process for the preparation of said micropowder and said molding, wherein the process comprises (i) providing a suspension containing a microporous aluminum-free zeolitic material of structure type MWW containing titanium and zinc, (ii) subjecting the suspension provided in (i) to spray-drying to obtain a micropowder; and (iii) optionally calcining the micropowder obtained in (ii). Still further, the present invention relates to a preferred use of said micropowder and said molding, in particular of said molding, as a catalyst, in particular for the epoxidation of propylene. Also, the present invention relates to a process for the epoxidation of propylene wherein as catalyst, said micropowder or said molding, in particular said molding is employed.

Catalysts based on titanium (Ti) containing zeolitic materials such as zeolitic materials of structure type MWW are known to be efficient catalysts for epoxidation reactions such as the epoxidation of propylene. In this respect, reference is made, for example, to Chemistry Letters (2000) pp. 774-775, J. Phys. Chem. B 105 (2001) p. 2897, U.S. Pat. No. 6,759,540, or U.S. Pat. No. 7,608,728.

In published Japanese patent application JP 2008-200553 A, a zeolitic material is described which contains zinc (Zn) in addition to Ti. This zeolitic material is prepared by contacting a titanosilicate having an MWW structure or a structure similar to MWW (TiMWW) with zinc compounds. The disclosure of this patent application is restricted to the preparation of a zeolitic powder which is obtained by treating TiMWW with a zinc compound. The thus resulting zeolitic powder is employed as catalyst for the epoxidation of propylene. According to the working examples, the respectively obtained selectivities for propylene oxide based on the consumed hydrogen peroxide were 89% and 92% whereas, according to the comparative example where TiMWW had been employed as catalyst, a respective selectivity of only 73% was observed.

U.S. Pat. No. 7,273,826 and U.S. Pat. No. 7,476,770 disclose the preparation an epoxidation catalyst which comprises a titanium or a vanadium zeolite, a binder and zinc oxide. This catalyst is prepared by subjecting a mixture of the zeolite, a binder source, and a zinc oxide source to rapid-drying. The resulting catalysts are described to be suitable for olefin epoxidation.

As suitable zeolitic materials, the zeolites known as TS-1 (titanium silicalite 1), TS-2 (titanium silicalite 2) and TS-3 (titanium silicalite 3) are disclosed. Further, a list of titanium containing molecular sieves having framework structure isomorphous to zeolite beta, mordenite, ZSM-48, ZSM-12, MCM-22 (MWW) and MCM-41 is described. According to these documents, it is especially preferred to employ the catalyst in epoxidation reactions where hydrogen peroxide is generated in situ. Therefore, the main focus of the documents is to be seen in catalysts which additionally contain a noble metal such as palladium. In this respect, reference is made to the working examples where exclusively a modified TS-1 catalyst is employed which was prepared by spray-drying a mixture comprising TS-1, colloidal silica binder and zinc oxide. Palladium as noble metal is then applied to the spray-dried product by ion exchange. This catalyst, i.e. the noble metal-treated spray-dried material, is then employed in an epoxidation reaction where methanol is used as solvent. With regard to the spray-drying step, it is disclosed in the working examples that the air feed temperature of the spray-drier is in the range of from 416 to 437° C. As to the spray-dried material as such, the only information which is given is the chemical composition comprising 0.35 weight-% zinc.

It was an object of the present invention to provide a novel micropowder comprising a zinc and titanium containing zeolitic material of structure type MWW which has advantageous characteristics, in particular when used as intermediate product for the preparation of a catalyst in the form of a molding.

It was another object of the present invention to provide a novel molding comprising the novel micropowder, in particular a molding having advantageous properties, preferably if used in epoxidation reactions.

It was yet another object of the present invention to provide a process for the preparation of said micropowder and said molding, in particular to provide a process resulting in a molding having advantageous properties, preferably if used in epoxidation reactions.

Surprisingly, it was found that a novel micropowder with particles exhibiting a specific size and pore characteristics represents such advantageous micropowder which is, in particular, a perfectly suitable intermediate for the preparation of a catalyst in the form of a molding.

As to said molding and the preparation thereof, it was found that by a specific post-treatment of a molding prepared based on said intermediate, the characteristics of the molding can be drastically improved, in particular in case the molding is employed as catalyst for the preparation of propylene oxide via epoxidation of propene.

Therefore, the present invention relates to a micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW).

The present invention relates also to a molding, comprising said micropowder, the molding preferably further comprising at least one binder, preferably a silica binder.

The present invention also relates to a process comprising
(i) providing a suspension containing a microporous aluminum-free zeolitic material of structure type MWW containing titanium and zinc (ZnTiMWW);
(ii) subjecting the suspension provided in (i) to spray-drying to obtain a micropowder;
(iii) optionally calcining the micropowder obtained in (ii).

The present invention also relates to said process, further comprising
(iv) shaping the micropowder obtained in (ii) or (iii) to obtain a molding;
(v) optionally drying and/or calcining the molding obtained in (iv).

The present invention also relates to said process, further comprising (vi) subjecting the molding obtained in (iv) or (v), preferably in (v), to a water-treatment;

(vii) optionally drying and/or calcining the water-treated molding.

The present invention also relates to the use of said micropowder or of said molding as a catalyst, preferably as a catalyst for preparing propylene oxide from propene with hydrogen peroxide as oxidizing agent in acetonitrile as solvent.

According to the present invention, it is conceivable that if hydrogen peroxide is used as oxidizing agent, the hydrogen peroxide is formed in situ during the reaction from hydrogen and oxygen or from other suitable precursors.

However, most preferably, the term "using hydrogen peroxide as oxidizing agent" as used in the context of the present invention relates to an embodiment where hydrogen peroxide is not formed in situ but employed as starting material, preferably in the form of a solution, preferably an at least partially aqueous solution, more preferably an aqueous solution, said preferably aqueous solution having a preferred hydrogen peroxide concentration in the range of from 20 to 60, more preferably from 25 to 55 weight-%, based on the total weight of the solution.

According to the present invention, a microporous aluminum-free zeolitic material of structure type MWW containing titanium and zinc (ZnTiMWW) is comprised in the inventive micropowder. The term "aluminum-free" as used in this context of the present invention relates to a ZnTiMWW which may contain aluminum only in traces as impurities which may result, for example, from aluminum impurities in the starting materials from which the ZnTiMWW is prepared. In particular, no aluminum source is used for the preparation of the ZnTiMWW. Typically, the aluminum-free ZnTiMWW according to the present invention contains at most 100 weight-ppm, preferably at most 50 weight-ppm of aluminum, based on the total weight of the ZnTiMWW.

The Micropowder

As mentioned above, the present invention relates to a micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW).

In the context of the present invention, it was surprisingly found that such a micropowder containing ZnTiMWW having particles with a certain particle size distribution is especially suitable for the preparation of a molding based on this micropowder. Due to a preferred use of the ZnTiMWW as catalytically active material, in particular in industrial-size processes, the preparation of such moldings was found to be of major importance since for example in continuous-type processes where the catalyst is employed as fixed-bed catalysts, moldings containing ZnTiMWW are one of the most preferred embodiments how the ZnTiMWW can be used as catalytically active material. Accordingly, it was found that the Dv10 values should have a certain minimum size which means that the micropowder should exhibit a certain minimum coarseness. Therefore, according to the present invention, the particles of the micropowder have a Dv10 value of at least 2 micrometer.

The term "Dv10 value" as referred to in the context of the present invention describes the average particle size where 10 vol. % of the particles of the micropowder have a smaller size. Similarly, the term "Dv50 value" as referred to in the context of the present invention describes the average particle size where 50 vol. % of the particles of the micropowder have a smaller size, and the term "Dv90 value" as referred to in the context of the present invention describes the average particle size where 90 vol. % of the particles of the micropowder have a smaller size. In particular, the Dv10, Dv50, and Dv90 values as referred to in the context of the present invention are to be understood as being determined using the apparatus and the respective parameters as specifically described in Reference Example 8.

Preferably, the Dv10 value, in micrometer, is at least 2.5, more preferably at least 3. More preferably, the Dv10 value, in micrometer, is less than 7, more preferably at most 6.5, more preferably at most 6, more preferably at most 5.5. Preferred ranges of the Dv10 value, in micrometer, are from 2 to less than 7, 2 to 6.5, 2 to 6, 2 to 5.5, 2.5 to less than 7, 2.5 to 6.5, 2.5 to 6, 2.5 to 5.5, 3 to less than 7, 3 to 6.5, 3 to 6, 3 to 5.5, with the range of from 3 to 5.5 being most preferred.

Generally, no specific restrictions exist with regard to the Dv50 and Dv90 values of the micropowder of the present invention. Preferably, the Dv50 value, in micrometer, is at least 7, more preferably in the range of from 7 to 25. Preferably, the Dv90 value, in micrometer, is at least 12, preferably in the range of from 12 to 85, such as at least 26, more preferably in the range of from 26 to 85. More preferably, the Dv50 value, in micrometer, is in the range of from 7 to 25 and the Dv90 value, in micrometer, is in the range of from 14 to 85 such as from 26 to 85.

Further according to the present invention, it was surprisingly found that such a micropowder containing ZnTiMWW having mesopores is especially suitable for the preparation of a molding based on this micropowder. Due to a preferred use of the ZnTiMWW as catalytically active material, in particular in industrial-size processes, the preparation of such moldings was found to be of major importance as described hereinabove. Accordingly, it was found that the mesopores of the micropowder render the micropowder an especially suitable intermediate for the preparation of the moldings since the presence of the mesopores which may act as transport pores during the use of the moldings in catalytic processes allows for a simplified process for the production of the moldings starting from such a micropowder since it is possible to avoid the use of an additional mesopore-forming agent during production of the molding. This advantage is further described in detail hereinunder. Therefore, according to the present invention, the micropowder comprises mesopores having an average pore diameter (4V/A) in the range of from 2 to 50 nm as determined by Hg porosimetry according to DIN 66133.

The term "4V/A" as used in this context of the present invention relates to four times the accumulated volume V of the pores between 2 and 50 nm, divided by A which relates to the accumulated surface of the pores between 2 and 50 nm.

Preferably, the mesopores have an average pore diameter (4V/A) in the range of from 5 to 50 nm, more preferably from 10 to 50 nm, more preferably from 10 to 45 nm, more preferably from 15 to 45 nm, more preferably from 15 to 35 nm, more preferably from 20 to 35 nm, more preferably from 20 to 30 nm, as determined by Hg porosimetry according to DIN 66133.

Further according to the present invention, it was surprisingly found that such a micropowder containing ZnTiMWW having mesopores is especially suitable for the preparation of a molding if the micropowder, in addition to the micropores of the ZnTiMWW and the mesopores, contains macropores. While it is not known exactly why such a micropowder is especially suitable, in particular if used as intermediate for the preparation of a molding containing ZnTiMWW, it might be possible that the presence of such macropores facilitates the workability of the formable mass, prepared from the micropowder, which is formed to yield the molding. Further, it might be possible that the micropowder which is contained in the finally obtained molding exhibits improved transport characteristics if used as catalyst in a process as already discussed hereinabove.

Therefore, according to the present invention, the micropowder additionally comprises macropores having an average pore diameter (4V/A) in the range of from more than 50 nm as determined by Hg porosimetry according to DIN 66133. As to the term "4V/A", reference is made to the respective discussion hereinabove.

Preferably, the macropores have an average pore diameter (4V/A) in the range of from 0.05 to 3 micrometer, more preferably from 0.05 to 2 micrometer, more preferably from 0.05 to 1 micrometer, more preferably from 0.05 to 0.5 micrometer, more preferably from 0.05 to 0.1 micrometer, as determined by Hg porosimetry according to DIN 66133.

According to the present invention, the micropowder contains ZnTiMWW which is a microporous zeolitic material. Generally, the micropores of the ZnTiMWW have an average pore diameter in the range of up to 2 nm as determined by nitrogen adsorption according to DIN 66135. Preferably, the micropores of the ZnTiMWW have an average pore diameter in the range of up to less than 2 nm, more preferably from 0.3 to 1.9 nm, more preferably from 0.4 to 1.8 nm, more preferably from 0.5 to 1.7 nm, more preferably from 0.6 to 1.6 nm, more preferably from 0.7 to 1.5 nm, more preferably from 0.8 to 1.4 nm, more preferably from 0.9 to 1.3 nm, more preferably from 1.0 to 1.2 nm, as determined by nitrogen adsorption according to DIN 66135.

Generally, it is conceivable that the micropowder of the present invention contains the ZnTiMWW in arbitrary amounts. For example, it may be conceivable that the micropowder, apart from the ZnTiMWW, further contains at least one chemical compound acting as binder material. Examples of such binders are metal oxides, such as, for example, $SiO_2$, $Al_2O_3$, $TiO_2$, $ZrO_2$ or MgO or clays or mixtures of two or more of these oxides, or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety, and graphite. Further binders might be, for example, clays, such as, for example, montmorillonites, kaolins, metakaolin, hectorite, bentonites, halloysites, dickites, nacrites or anaxites. According to this conceivable embodiment, the micropowder may contain, based on the weight of the micropowder, up to 95 weight-% or up to 90 weight-% or up to 85 weight-% or up to 80 weight-% or up to 75 weight-% or up to 70 weight-% or up to 65 weight-% or up to 60 weight-% or up to 55 weight-% or up to 50 weight-% or up to 45 weight-% or up to 40 weight-% or up to 35 weight-% or up to 30 weight-% or up to 25 weight-% or up to 20 weight-% or up to 15 weight-% or up to 10 weight-% or up to 5 weight-% of one or more binder materials.

According to an especially preferred embodiment of the present invention, the ZnTiMWW containing micropowder contains essentially no chemical compound other than the ZnTiMWW zeolitic material as such. Preferably, the micropowder of the invention comprises, based on the weight of the micropowder, at least 95, more preferably at least 96 weight-%, more preferably at least 97 weight-%, more preferably at least 98 weight-%, more preferably at least 99 weight-%, more preferably at least 99.5 weight-%, more preferably at least 99.7 weight-% of the ZnTiMWW.

As to the ZnTiMWW which is contained in the micropowder of the present invention, no specific restrictions exist as far as the Zn content of the ZnTiMWW is concerned. Generally, Zn contents, calculated as elemental Zn, in the range of from, for example, up to 5 weight-% are conceivable, with conceivable ranges of from 0.01 to 5 weight-%, or from 0.02 to 4 weight-%, or from 0.05 to 3 weight-%, or from 0.1 to 2 weight-%. Surprisingly, in particular if used as catalytically active material, more particularly if used as catalytically active material in epoxidation processes as described in detail hereinbelow, it was found that it is of particular advantage if the Zn content of the ZnTiMWW is in a narrow range of from 1.0 to 2.0 weight-%, preferably of from 1.1 to 1.95 weight-%, more preferably of from 1.2 to 1.9 weight-%, more preferably of from 1.3 to 1.85 weight-%, calculated as Zn and based on the weight of the ZnTiMWW. Contrary to JP 2008-200553 A where either a very low or a very high Zn content is disclosed, it was found that a narrow range of the Zn content of the ZnTiMWW allows for highly improved epoxidation results, in particular in view of the selectivity of the process with regard to epoxidized compound relative to the oxidizing agent.

As to the ZnTiMWW which is contained in the micropowder of the present invention, no specific restrictions exist as far as the Ti content of the ZnTiMWW is concerned. Generally, Ti contents, calculated as elemental Ti, in the range of from, for example, up to weight-% are conceivable, with conceivable ranges of from 0.01 to 5 weight-%, or from 0.02 to 4 weight-%, or from 0.05 to 3 weight-%, or from 0.1 to 2 weight-%. In particular if used as catalytically active material, more particularly if used as catalytically active material in epoxidation processes as described in detail hereinbelow, it was found that it is of particular advantage if the Ti content of the ZnTiMWW is in a narrow range of from 1.0 to 2.0 weight-%, preferably of from 1.1 to 1.9 weight-%, more preferably of from 1.2 to 1.8 weight-%, calculated as Ti and based on the weight of the ZnTiMWW.

According to the present invention, the crystallinity of the ZnTiMWW which is contained in the inventive micropowder, as determined by X-ray diffraction (XRD) analysis, may vary in broad ranges. For example, the crystallinity of the ZnTiMWW may be at least 20%, preferably at least 30%, more preferably at least 40%, more preferably at least 50%, more preferably at least 60%, more preferably at least 70%. According to a preferred embodiment of the present invention, the crystallinity of the ZnTiMWW which is contained in the inventive micropowder is at least 80%, preferably at least 81%, more preferably at least 82%, more preferably at least 83%, more preferably at least 84%, more preferably at least 85%. Each value is to be understood as having a measurement inaccuracy of plus/minus 10%.

Contrary to the teaching of U.S. Pat. No. 7,273,826 and U.S. Pat. No. 7,476,770 which both disclose spray-powders which are used as catalysts and, for this purpose, must contain at least one noble metal, it was found in the context of the present invention that micropowders are preferred, in particular if used as catalytically active materials, which contain ZnTiMWW and which are essentially free of noble metals. Therefore, according to particularly preferred embodiments of the present invention, the micropowder comprises, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.

Usually, as described hereinabove, ZnTiMWW is prepared from a precursor of type B-MWW, a boron containing zeolite having framework structure MWW. However, in particular if used as catalytically active material, more particularly if used as catalytically active material in epoxidation processes as described in detail hereinbelow, boron contained in the ZnTiMWW and, thus, in the inventive micropowder, may decrease the catalytic performance. Therefore, preferably, the micropowder of the present invention comprises, based on the total weight of the micropowder and calculated as element, less than 0.1 weight-%, more preferably less than 0.08 weight-%, more preferably less than 0.06 weight-%, more preferably less than 0.04 weight-%, more preferably less than 0.02 weight-%, more preferably less than 0.01 weight-% of boron. Therefore, it is preferred to prepare the ZnTiMWW from a deboronated precursor of type B-MWW.

As discussed above, the micropowder of the present invention is, for example, of particular advantage if it is used as an intermediate for the preparation of a molding. Especially for this purpose, it was found that for the preparation of a formable mass from which the molding is prepared, a specific bulk density of the micropowder is advantageous. Preferably, the bulk density of the micropowder of the present invention is in the range of from 20 to 250 g/ml, more preferably from 30 to 200 g/ml, more preferably from 40 to 180 g/ml, more preferably from 50 to 160 g/ml, more preferably from 60 to 140 g/ml, more preferably from 70 to 120 g/ml, more preferably from 80 to 100 g/ml.

Preferably, the total organic carbon (TOC) content of the micropowder of the present invention is less than 1 weight-%, preferably less than 0.9 weight-%, more preferably less than 0.8 weight-%, more preferably less than 0.7 weight-%, more preferably less than 0.6 weight-%, more preferably less than 0.5 weight-%, more preferably less than 0.4 weight-%, more preferably less than 0.3 weight-%.

According to an especially preferred embodiment, the present invention relates to a micropowder, the particles of which having a Dv10 value in the range of from 3 to 5.5 micrometer, said micropowder comprising mesopores having an average pore diameter (4V/A) in the range of from 20 to 30 nm as determined by Hg porosimetry according to DIN 66133, and comprising, based on the weight of the micropowder, at least 99.7 weight-% of a microporous aluminum-free zeolitic material of structure type MWW containing titanium and zinc (ZnTiMWW), wherein the micropores of the ZnTiMWW preferably have an average pore diameter in the range of from 1.0 to 1.2 nanometer as determined by nitrogen adsorption according to DIN 66135.

According to an especially preferred embodiment, the present invention relates to a micropowder, the particles of which having a Dv10 value in the range of from 3 to 5.5 micrometer, said micropowder comprising mesopores having an average pore diameter (4V/A) in the range of from 20 to 30 nm as determined by Hg porosimetry according to DIN 66133, and comprising, based on the weight of the micropowder, at least 99.7 weight-% of a microporous aluminum-free zeolitic material of structure type MWW containing titanium and zinc (ZnTiMWW), wherein the micropores of the ZnTiMWW preferably have an average pore diameter in the range of from 1.0 to 1.2 nanometer as determined by nitrogen adsorption according to DIN 66135, wherein the ZnTiMWW contains zinc in an amount of from 1.2 to 1.9 weight-%, calculated as Zn and based on the weight of the ZnTiMWW.

According to an especially preferred embodiment, the present invention relates to a micropowder, the particles of which having a Dv10 value in the range of from 3 to 5.5 micrometer, said micropowder comprising mesopores having an average pore diameter (4V/A) in the range of from 20 to 30 nm as determined by Hg porosimetry according to DIN 66133, said micropowder further comprising macropores having an average pore diameter (4V/A) in the range of from 0.05 to 3 micrometer, as determined by Hg porosimetry according to DIN 66133, and comprising, based on the weight of the micropowder, at least 99.7 weight-% of a microporous aluminum-free zeolitic material of structure type MWW containing titanium and zinc (ZnTiMWW), wherein the micropores of the ZnTiMWW preferably have an average pore diameter in the range of from 1.0 to 1.2 nanometer as determined by nitrogen adsorption according to DIN 66135.

According to an especially preferred embodiment, the present invention relates to a micropowder, the particles of which having a Dv10 value in the range of from 3 to 5.5 micrometer, said micropowder comprising mesopores having an average pore diameter (4V/A) in the range of from 20 to 30 nm as determined by Hg porosimetry according to DIN 66133, said micropowder further comprising macropores having an average pore diameter (4V/A) in the range of from 0.05 to 3 micrometer, as determined by Hg porosimetry according to DIN 66133, and comprising, based on the weight of the micropowder, at least 99.7 weight-% of a microporous aluminum-free zeolitic material of structure type MWW containing titanium and zinc (ZnTiMWW), wherein the micropores of the ZnTiMWW preferably have an average pore diameter in the range of from 1.0 to 1.2 nanometer as determined by nitrogen adsorption according to DIN 66135, wherein the ZnTiMWW contains zinc in an amount of from 1.2 to 1.9 weight-%, calculated as Zn and based on the weight of the ZnTiMWW.

As far as the preparation of the micropowder of the present invention is concerned, no particular restrictions exist provided that a micropowder is obtained having above-described characteristics. Most preferably, the micropowder of the present invention is prepared via rapid-drying a suspension containing the ZnTiMWW wherein spray-granulating or spray-drying, preferably spray-drying a suspension containing the ZnTiMWW is especially preferred. Therefore, the micropowder of the present invention is preferably a spray powder which is preferably obtainable or obtained by spray-drying. Concerning this preferred embodiment, the term "micropowder" as used in the context of the present invention could be replaced by the term "spray powder".

Therefore, the present invention also relates to a process comprising
(i) providing a suspension containing a microporous aluminum-free zeolitic material of structure type MWW containing titanium and zinc (ZnTiMWW);
(ii) subjecting the suspension provided in (i) to spray-drying to obtain a micropowder;
(iii) optionally calcining the micropowder obtained in (ii).

As mentioned above, spray-drying is the preferred method according to the present invention how the micropowder of the invention is prepared. However, other rapid-drying methods such as fluidized-bed spray-granulation or fluidized-bed granulation may also be conceivable.

According to preferred embodiment, the micropowder obtained according to (ii) or (iii), preferably (iii), is the micropowder as defined above. Therefore, the present invention also relates to a process for the preparation of a micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW), said process comprising (i) providing a suspension containing a microporous aluminum-free zeolitic material of structure type MWW containing titanium and zinc (ZnTiMWW);
(ii) subjecting the suspension provided in (i) to spray-drying to obtain a micropowder;
(iii) optionally calcining the micropowder obtained in (ii).

Providing the Suspension According to (i)

ZnTiMWW

The ZnTiMWW based on which the suspension in (i) is provided, can be prepared according to all conceivable methods. For example, it is possible to prepare a microporous aluminum-free zeolitic material of structure type MWW containing titanium (TiMWW) and subject the TiMWW to a suitable treatment to obtain the ZnTiMWW. Further, it is possible to prepare an aluminum-free zeolitic material of structure type MWW (MWW) and subject the MWW to a suitable treatment to obtain the ZnTiMWW wherein, for example, both Zn and Ti are suitably incorporated in the MWW. Further, it is conceivable to prepare aluminum-free zeolitic material of structure type MWW wherein, during the synthesis of the MWW-type framework, Ti is introduced and the resulting material is subjected to a suitable treatment to incorporate Zn, or Zn is introduced and the resulting material is subjected to a suitable treatment to incorporate Ti, or both Zn and Ti are introduced. As conceivable methods for the preparation of TiMWW, the processes as described, for example, in U.S. Pat. No. 6,114,551, or in Wu et al., "Hydrothermal Synthesis of a novel Titanosilicate with MWW Topology", Chemistry Letters (2000), pp. 774-775 may be mentioned.

According to a preferred process, an aluminum-free zeolitic material of structure type MWW containing Ti (TiMWW) is prepared in a first stage, and in a second stage, the TiMWW is subjected to a suitable treatment to obtain the ZnTiMWW.

According to a preferred embodiment of the present invention, the ZnTiMWW is prepared according to a process comprising (I) preparing an aluminum-free zeolitic material of structure type MWW containing boron (B-MWW);
(II) deboronating the B-MWW to obtain an aluminum-free zeolitic material of structure type MWW (MWW);
(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation to obtain the ZnTiMWW.

Therefore, the present invention also relates to the process as defined above, wherein the ZnTiMWW used for providing the suspension according to (i) is prepared by a process comprising (I) preparing an aluminum-free zeolitic material of structure type MWW containing boron (B-MWW);
(II) deboronating the B-MWW to obtain an aluminum-free zeolitic material of structure type MWW (MWW);
(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation to obtain the ZnTiMWW.

Stage (I)

As far as (I) is concerned, no specific restrictions exist. Preferably, a suitable starting mixture, preferably an aqueous mixture, containing the B-MWW precursors, preferably the B containing precursor and the Si containing precursor, preferably including at least one suitable micropore-forming agent, is subjected to hydrothermal crystallization under autogenous pressure. For crystallization purposes, it may be conceivable to use at least one suitable seeding material. As suitable Si containing precursors, fumed silica or colloidal silica, preferably colloidal silica such as, for example, ammonia-stabilized colloidal silica such as Ludox® AS-40 may be mentioned by way of example. As suitable boron containing precursor, boric acid, $B_2O_3$, borate salts, preferably boric acid may be mentioned by way of example. As suitable micropore-forming agent, piperidine, hexamethylene imine, or mixtures of piperidine and hexamethylene imine may be mentioned by way of example. Preferably, the crystallization time is in the range of from 3 to 8 days, more preferably from 4 to 6 days. During hydrothermal synthesis, the crystallization mixture may be stirred. The temperatures applied during crystallization are preferably in the range of from 160 to 200° C., more preferably from 160 to 180° C.

After hydrothermal synthesis, the obtained crystalline zeolitic material B-MWW precursor is preferably suitably separated from the mother liquor. All methods of separating the B-MWW precursor from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the B-MWW precursor is preferably separated from its mother liquid by filtration to obtain a filter cake which is preferably subjected to washing, preferably with water. Subsequently, the filter cake, optionally further processed to obtained a suitable suspension, is subjected to spray drying or to ultrafiltration. Prior to separating the B-MWW precursor from its mother liquor, it is possible to increase the B-MWW precursor content of the mother liquor by concentrating the suspension. If washing is applied, it is preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm.

After separation of the B-MWW from the suspension, preferably achieved via filtration, and after washing, the washed filter cake containing the B-MWW precursor is preferably subjected to pre-drying, for example by subjecting the filter cake to a suitable gas stream, preferably a nitrogen stream, for a time preferably in the range of from 4 to 10 h, more preferably from 5 to 8 h.

Subsequently, the pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. Such drying can be accomplished, for example, by spray-drying. Further, it is possible to separate the B-MWW precursor from its mother liquor via a suitable filtration method, followed by washing and spray-drying.

After drying, the B-MWW precursor is preferably subjected to calcination to obtain the B-MWW at temperatures in the range of from 500 to 700° C., more preferably from 550 to 675° C., more preferably from 600 to 675° C. in a suitable atmosphere such as technical nitrogen, air, or lean air, preferably in air or lean air.

Preferably, in stage (I), the B-MWW is prepared by a process whose preferred steps and conditions are defined by the following embodiments 1 to 28 and the respective dependencies as indicated:

1. A process for preparing an aluminum-free boron containing zeolitic material comprising the framework structure MWW (B-MWW), comprising
   (a) hydrothermally synthesizing a B-MWW precursor from a synthesis mixture containing water, a silicon source, a boron source, and an MWW template compound obtaining the B-MWW precursor in its mother liquor, the mother liquor having a pH above 9;
   (b) adjusting the pH of the mother liquor, obtained in (a) and containing the B-MWW precursor, to a value in the range of from 6 to 9;
   (c) separating the B-MWW precursor from the pH-adjusted mother liquor obtained in (b) by filtration in a filtration device.
2. The process of embodiment 1, wherein in (a), at least 95 weight-%, preferably at least 99 weight-%, more preferably at least 99.9 weight-% of the synthesis mixture consist of the water, the silicon source, the boron source, and the template compound.
3. The process of embodiment 1 or 2, wherein in (a), the silicon source is selected from the group consisting of fumed silica, colloidal silica, and a mixture thereof, the silicon source preferably being colloidal silica, more preferably ammonia-stabilized silica, the boron source is selected from the group consisting of boric acid, borates, boron oxide, and a mixture of two or more thereof, the boron source preferably being boric acid, and the MWW template compound selected from the group consisting of piperidine, hexamethylene imine, N,N,N,N',N',N'-hexamethyl-1,5-pentanediammonium ion, 1,4-bis(N-methylpyrrolidinium) butane, octyltrimethylammonium hydroxide, heptyltrimethylammonium hydroxide, hexyltrimethylammonium hydroxide, N,N,N-trimethyl-1-adamantylammonium hydroxide, and a mixture of two or more thereof, the MWW template compound preferably being piperidine.
4. The process of any of embodiments 1 to 3, wherein in (a), the synthesis mixture contains the boron source, calculated as elemental boron, relative to the silicon source, calculated as elemental silicon, in a molar ratio in the range of from 0.4:1 to 2.0:1, preferably from 0.6:1 to 1.9:1, more preferably from 0.9:1 to 1.4:1, the water relative to the silicon source, calculated as elemental silicon, in a molar ratio in the range of from 1:1 to 30:1, preferably from 3:1 to 25:1, more preferably from 6:1 to 20:1; and the template compound relative to the silicon source, calculated as elemental silicon, in a molar ratio in the range of from 0.4:1 to 2.0:1, preferably from 0.6:1 to 1.9:1, more preferably from 0.9:1 to 1.4:1.
5. The process of any of embodiments 1 to 4, wherein in (a), the hydrothermal synthesizing is carried out at a temperature in the range of from 160 to less than 180° C., preferably from 170 to 175° C., for a period of time in the range of from 1 to 72 h, preferably from 6 to 60 h, more preferably from 12 to 50 h.
6. The process of any of embodiments 1 to 5, wherein in (a), the hydrothermal synthesizing is carried out at least partially under stirring.
7. The process of any of embodiments 1 to 6, wherein in (a), the synthesis mixture additionally contains a seeding material, preferably a zeolitic material comprising the framework structure MWW, more preferably a boron containing zeolitic material comprising the framework structure MWW.
8. The process of embodiment 7, wherein the synthesis mixture contains the seeding material, relative to the silicon source, in a weight ratio in the range of from 0.01:1 to 1:1, preferably from 0.02:1 to 0.5:1, more preferably from 0.03:1 to 0.1:1, calculated as amount of seeding material in kg relative to silicon contained in the silicon source calculated as silicon dioxide in kg.
9. The process of any of embodiments 1 to 8, wherein the pH of the mother liquor obtained from (a) is above 10, preferably in the range of from 10.5 to 12, more preferably from 11 to 11.5.
10. The process of any of embodiments 1 to 9, wherein in (b), the pH of the mother liquor obtained in (a) is adjusted to a value in the range of from 6.5 to 8.5, preferably from 7 to 8.
11. The process of any of embodiments 1 to 10, wherein in (b), the pH is adjusted by a method comprising
    (i) adding an acid to the mother liquor obtained from (a) containing the B-MWW precursor, wherein the adding is preferably carried out at least partially under stirring.
12. The process of embodiment 11, wherein in (i), the adding is carried out at a temperature in the range of from 20 to 70° C., preferably from 30 to 65° C., more preferably from 40 to 60° C.
13. The process of embodiment 11 or 12, wherein in (i), the acid is an inorganic acid, preferably an aqueous solution containing the inorganic acid.
14. The process of embodiment 13, wherein the inorganic acid is selected from the group consisting of phosphoric acid, sulphuric acid, hydrochloric acid, nitric acid, and a mixture of two or more thereof, the inorganic acid preferably being nitric acid.
15. The process of any of embodiments 11 to 14, the method additionally comprising
    (ii) stirring the mother liquor to which the acid was added according to (i), wherein during (ii), no acid is added to the mother liquor.
16. The process of embodiment 15, wherein in (ii), the stirring is carried out at a temperature in the range of from 20 to 70° C., preferably from 25 to 65° C., more preferably from 30 to 60° C.
17. The process of any of embodiments 1 to 16, wherein in (b), the size of the particles contained in the mother liquor, expressed by the respective Dv10, Dv50, and Dv90 value, is increased for at least 2%, preferably at least 3%, more preferably at least 4.5% regarding Dv10, for at least 2%, preferably at least 3%, more preferably at least 4.5% regarding Dv50, and for at least 5%, preferably at least 6%, more preferably at least 7% regarding Dv90.
18. The process of any of embodiments 1 to 17, wherein the pH-adjusted mother liquor obtained from (b) has a solids content in the range of from 1 to 10 weight-%, preferably from 4 to 9 weight-%, more preferably from 7 to 8 weight-%, based on the total weight of the pH-adjusted mother liquor obtained from (b).
19. The process of any of embodiments 1 to 18, wherein the pH-adjusted mother liquor obtained from (b) has a filtration resistance in the range of from 10 to 50 mPa*s/m$^2$, preferably from 15 to 45 mPa*s/m$^2$, more preferably from 20 to 40 mPa*s/m$^2$.
20. The process of any of embodiments 1 to 19, further comprising (d) washing the B-MWW precursor obtained from (c), preferably the filter cake obtained from (c), wherein the washing is preferably performed using water was washing agent.

21. The process of embodiment 20, wherein in (d), the filter cake obtained from (c) is has a washing resistance in the range of from 10 to 50 mPa*s/m², preferably from 15 to 45 mPa*s/m², more preferably from 20 to 40 mPa*s/m².

22. The process of embodiment 20 or 21, wherein the washing is carried out until the conductivity of the filtrate is at most 300 microSiemens/cm, preferably at most 250 microSiemens/cm, more preferably at most 200 microSiemens/cm.

23. The process of any of embodiments 1 to 22, further comprising
   (e) drying the B-MWW precursor obtained from (c), preferably from (d), at a temperature in the range of from 20 to 50° C., preferably from 20 to 40° C., more preferably from 20 to 30° C., wherein the drying is preferably carried out by subjecting the B-MWW to a gas stream, preferably a nitrogen stream.

24. The process of any of embodiments 1 to 23, wherein the residual moisture of the B-MWW precursor obtained from (c), preferably from (d), more preferably from (e), is in the range of from 80 to 90 weight-%, preferably from 80 to 85 weight-%.

25. The process of any of embodiments 1 to 24, further comprising
   (f) preparing a suspension, preferably an aqueous suspension, containing the B-MWW precursor obtained from to (c), preferably from (d), more preferably from (e), and having a solids content in the range of from 10 to 20 weight-%, preferably from 12 to 18 weight-%, more preferably from 14 to 16 weight-%;
   (g) spray drying the suspension obtained from (f) containing the B-MWW precursor, obtaining a spray powder;
   (h) calcining the spray powder obtained from (g) containing the B-MWW precursor, preferably at a temperature in the range of from 500 to 700° C., more preferably from 550 to 650° C., more preferably from 575 to 625° C. for a period of time in the range of from 1 to 24 h, preferably from 2 to 18 h, more preferably from 6 to 12 h, obtaining a spray powder of which at least 99 weight-%, more preferably at least 99.5 weight-% consist of the B-MWW.

26. The process of embodiment 25, wherein in (h), the calcining is carried out in continuous mode, preferably in a rotary calciner, preferably at a throughput in the range of from 0.5 to 20 kg spray powder per h.

27. The process of embodiment 25 or 26, wherein the degree of crystallinity of the B-MWW contained in the spray powder obtained from (h) is at least (75±5) %, preferably at least (80±5) %, as determined via XRD.

28. The process of any of embodiments 25 to 27, wherein the BET specific surface area of the B-MWW contained in the spray powder obtained from (h) is at least 300 m²/g, preferably in the range of from 300 to 500 m²/g, as determined according to DIN 66131.

According to the present invention, the B-MWW obtained has a B content preferably in the range of from 1.2 to 2.4 weight-% or from 1.4 to 2.4 weight-%, calculated as elemental B. Further, the B-MWW obtained has a Si content preferably in the range of from 38 to 45 weight-% or from 38 to 44 weight-%, calculated as elemental Si. Further, the B-MWW obtained has a C content (total organic carbon, TOC) preferably in the range of from 0.14 to 0.25 weight-%, more preferably from 0.15 to 0.22 weight-%, more preferably from 0.16 to 0.20 weight-%, calculated as elemental C. More preferably, the B-MWW obtained has a C content (total organic carbon, TOC) of less than 0.3 weight-%, more preferably less than 0.2 weight-%, more preferably less than 0.1 weight-%.

Stage (II)

As far as (II) is concerned, no specific restrictions exist. Preferably, the deboration of the B-MWW to obtain the aluminum-free zeolitic material of structure type MWW (MWW) is achieved via suitable treatment of the B-MWW with a liquid solvent system which may or may not contain at least one inorganic and/or at least one organic acid, or a salt thereof. Conceivable acids are, for example, hydrochloric acid, sulfuric acid, nitric acid, phosphoric acid, formic acid, acetic acid, propionic acid, oxalic acid, and tartaric acid. Preferred acids are inorganic acids, with nitric acid being especially preferred. The liquid solvent system is preferably selected from the group consisting of water, monohydric alcohols, polyhydric alcohols, and mixtures of two or more thereof.

According to a preferred embodiment of the present invention, the liquid solvent system is selected from the group consisting of water, monohydric alcohols, polyhydric alcohols, and mixtures of two or more thereof, and wherein said liquid solvent system does not contain an inorganic or organic acid or a salt thereof, the acid being selected from the group consisting of hydrochloric acid, sulfuric acid, nitric acid, phosphoric acid, formic acid, acetic acid, propionic acid, and tartaric acid. More preferably, the liquid solvent system does not contain an inorganic or organic acid, or a salt thereof. Even more preferably, the liquid solvent system is selected from the group consisting of water, methanol, ethanol, propanol, ethane-1,2-diol, propane-1,2-diol, propane-1,3-diol, propane-1,2,3-triol, and mixtures of two or more thereof. Most preferably, the liquid solvent system is water.

The treatment according to (II) is preferably carried out at a temperature in the range of from 75 to 125° C., more preferably from 85 to 115° C., for a time preferably in the range of from 8 to 15 h, more preferably from 9 to 12 h.

The obtained deboronated crystalline zeolitic material MWW is preferably suitably separated from the suspension further comprising water and/or acid. All methods of separating the MWW from the suspension are conceivable. These methods include, for example, filtration, ultrafiltration, diafiltration and centrifugation methods or, for instance, spray drying processes and spray granulation processes. A combination of two or more of these methods can be applied. According to the present invention, the MWW is preferably separated from the suspension by filtration to obtain a filter cake which is preferably subjected to washing, preferably with water. Subsequently, the filter cake, optionally further processed to obtain a suitable suspension, is subjected to spray drying or to ultrafiltration. Prior to separating the MWW from the suspension, it is possible to increase the MWW content of the suspension by concentrating the suspension. If washing is applied, it may be preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm.

After separation of the MWW from the suspension, preferably achieved via filtration, and after washing, the washed filter cake containing the MWW is preferably subjected to pre-drying, for example by subjecting the filter cake to a suitable gas stream, preferably a nitrogen stream, for a time preferably in the range of from 4 to 10 h, more preferably from 5 to 8 h.

Subsequently, the pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. Such drying can be accomplished, for example, by spray-drying. Further, it is possible to separate the MWW from the suspension via a suitable filtration method, followed by washing and spray-drying.

After drying, the MWW can be subjected to calcination at temperatures in the range of from 500 to 700° C., more preferably from 550 to 675° C., more preferably from 600 to 675° C. in a suitable atmosphere such as technical nitrogen, air, or lean air, preferably in air or lean air. Preferably, no calcination is carried out according to (II).

Preferably, stage (II) is carried by a process whose preferred steps and conditions are defined by the following embodiments 1 to 7 and the respective dependencies as indicated:

1. A process for the preparation of a zeolitic material, comprising
    (i) providing the boron-containing zeolitic material of structure type MWW (B-MWW) obtained according to stage (I);
    (ii) deboronating the B-MWW by treating the B-MWW with a liquid solvent system thereby obtaining a deboronated B-MWW (MWW);
    wherein the liquid solvent system is selected from the group consisting of water, monohydric alcohols, polyhydric alcohols, and mixtures of two or more thereof, and wherein said liquid solvent system does not contain an inorganic or organic acid or a salt thereof, the acid being selected from the group consisting of hydrochloric acid, sulfuric acid, nitric acid, phosphoric acid, formic acid, acetic acid, propionic acid, oxalic acid, and tartaric acid.
2. The process of embodiment 1, wherein the liquid solvent system does not contain an inorganic or organic acid, or a salt thereof.
3. The process of embodiment 1 or 2, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water.
4. The process of any of embodiments 1 to 3, wherein the treating according to (ii) is carried out at a temperature in the range of from 50 to 125° C.
5. The process of any of embodiments 1 to 4, wherein the treating according to (ii) is carried out for a time in the range of from 6 to 20 h.
6. The process of any of embodiments 1 to 5, wherein the treating according to (ii) is carried out in at least 2 separate steps, wherein between at least 2 treating steps, the MWW is dried, preferably at a temperature in the range of from 100 to 150° C.
7. The process of any of embodiments 1 to 6, further comprising
    (iii) post-treating the MWW obtained from (ii) by a process comprising
        (iii.1) separating the MWW from the liquid solvent system;
        (iii.2) preferably drying the separated MWW, preferably by spray-drying;
        (iii.3) optionally calcining the MWW obtained from (a) or (b), preferably at temperatures in the range of from 500 to 700° C.

According to the present invention, the MWW obtained has a B content preferably of at most 0.1 weight-%, more preferably at most 0.09 weight-%, more preferably at most 0.08 weight-%, calculated as elemental B. Further, the MWW obtained has a Si content preferably in the range of from 39 to 45 weight-%, calculated as elemental Si. Further, the MWW obtained has a C content (total organic carbon, TOC) preferably in the range of from 0.15 to 0.30 weight-%, more preferably from 0.18 to 0.27 weight-%, more preferably from 0.20 to 0.25 weight-%, calculated as elemental C. More preferably, the B-MWW obtained has a C content (total organic carbon, TOC) of less than 0.3 weight-%, more preferably less than 0.2 weight-%, more preferably less than 0.1 weight-%.

Stage (III)

As far as (III) is concerned, no specific restrictions exist. Preferably, a suitable starting mixture, preferably an aqueous mixture, containing the MWW and a Ti containing precursor, and preferably containing at least one suitable micropore-forming agent, is subjected to hydrothermal crystallization under autogenous pressure. It may be conceivable to use at least one suitable seeding material. As suitable Ti containing precursor, tetraalkylorthotitanates such as tetrabutylorthotitanate may be mentioned by way of example. As suitable micropore-forming agent, piperidine, hexamethylene imine, or mixtures of piperidine and hexamethylene imine may be mentioned by way of example. Preferably, the crystallization time is in the range of from 4 to 8 days, more preferably from 4 to 6 days. During hydrothermal synthesis, the crystallization mixture may be stirred. The temperatures applied during crystallization are preferably in the range of from 160 to 200° C., more preferably from 160 to 180° C.

After hydrothermal synthesis, the obtained crystalline zeolitic material TiMWW is preferably suitably separated from the mother liquor. All methods of separating the TiMWW from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the TiMWW is preferably separated from its mother liquid by filtration to obtain a filter cake which is preferably subjected to washing, preferably with water. Subsequently, the filter cake, optionally further processed to obtained a suitable suspension, is subjected to spray drying or to ultrafiltration. Prior to separating the TiMWW from its mother liquor, it is possible to increase the TiMWW content of the mother liquor by concentrating the suspension. If washing is applied, it is preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm.

After separation of the TiMWW from its mother liquor, preferably achieved via filtration, and after washing, the washed filter cake containing the TiMWW is preferably subjected to pre-drying, for example by subjecting the filter cake to a suitable gas stream, preferably a nitrogen stream, for a time preferably in the range of from 4 to 10 h, more preferably from 5 to 8 h.

Subsequently, the pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. Such drying can be accomplished, for example, by spray-drying.

After drying, the TiMWW may be subjected to calcination at temperatures in the range of from 500 to 700° C., more preferably from 550 to 675° C., more preferably from 600 to 675° C. in a suitable atmosphere such as technical nitrogen, air, or lean air, preferably in air or lean air. Preferably, no calcination is carried out according to (III).

According to the present invention, the TiMWW obtained has a Ti content preferably in the range of from 2.1 to 2.7 weight-%, more preferably from 2.2 to 2.6 weight-%, more preferably from 2.3 to 2.5 weight-%, calculated as elemental Ti. Further, the TiMWW obtained has a Si content preferably in the range of from 34 to 40 weight-%, more preferably from 35 to 39 weight-%, more preferably from 36 to 38 weight-%, calculated as elemental Si. Further, the TiMWW obtained has a C content (total organic carbon, TOC) preferably in the range of from 7.0 to 8.0 weight-%, more preferably from 7.2 to 7.8 weight-%, more preferably from 7.4 to 7.6 weight-%, calculated as elemental C.

Stage (IV)

Stage (IV) of the process of the present invention preferably serves for reducing the Ti content of the TiMWW as obtained from stage (III), which reduction of the Ti content is preferably achieved by the acid treatment, and preferably also for reducing the carbon content, which reduction of the carbon content is preferably achieved by the calcination as described below. It is noted that according to a conceivable embodiment of the present invention, it may be possible to prepare a TiMWW in stage (III) which already exhibits the desired Ti content. Further, it may be possible in stage (III) to carry out a suitable calcination which results in a carbon content which is low enough so that the respectively obtained TiMWW could be processed further according to stage (V).

Generally, as far as (IV) is concerned, no specific restrictions exist. Preferably, the acid treatment of the TiMWW as obtained according to stage (III) to obtain the finally desired aluminum-free zeolitic material of structure type TiMWW is achieved via suitable treatment of the TiMWW with at least one acid, preferably an inorganic acid, more preferably nitric acid. The treatment according to (IV) is preferably carried out at a temperature in the range of from 75 to 125° C., more preferably from 85 to 115° C., for a time preferably in the range of from 17 to 25 h, more preferably from 18 to 22 h.

After the acid treatment, the obtained crystalline zeolitic material TiMWW is preferably suitably separated from the suspension further comprising an acid. All methods of separating the TiMWW from the suspension are conceivable. These methods include, for example, filtration, ultrafiltration, diafiltration and centrifugation methods or, for instance, spray drying processes and spray granulation processes. A combination of two or more of these methods can be applied. According to the present invention, the TiMWW is preferably separated from the suspension by filtration to obtain a filter cake which is preferably subjected to washing, preferably with water. Subsequently, the filter cake, optionally further processed to obtained a suitable suspension, is subjected to spray drying or to ultrafiltration. Prior to separating the TiMWW from the suspension, it is possible to increase the TiMWW content of the suspension by concentrating the suspension. If washing is applied, it may be preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm.

After separation of the TiMWW from the suspension, preferably achieved via filtration, and after washing, the washed filter cake containing the TiMWW is preferably subjected to pre-drying, for example by subjecting the filter cake to a suitable gas stream, preferably a nitrogen stream, for a time preferably in the range of from 4 to 10 h, more preferably from 5 to 8 h.

Subsequently, the pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. Such drying can be accomplished, for example, by spray-drying. Further, it is possible to separate the TiMWW from the suspension via a suitable filtration method, followed by washing and spray-drying.

After drying, the TiMWW is preferably subjected to calcination at temperatures in the range of from 500 to 700° C., more preferably from 550 to 675° C., more preferably from 600 to 675° C. in a suitable atmosphere such as technical nitrogen, air, or lean air, preferably in air or lean air.

Preferably, stages (III) and (IV) are carried out by a process whose preferred steps and conditions are defined by the following embodiments 1 to 27 and the respective dependencies as indicated:

1. A process for the preparation of a titanium-containing zeolitic material having an MWW framework structure comprising
   (i) providing the deboronated crystalline zeolitic material MWW obtained according to stage (II);
   (ii) incorporating titanium into the zeolitic material provided in (i) comprising
      (ii.1) preparing an aqueous synthesis mixture containing the zeolitic material provided in (i), an MWW template compound and a titanium source, wherein the molar ratio of the MWW template compound relative to Si, calculated as $SiO_2$ and contained in the zeolitic material provided in (i), is in the range of from 0.5:1 to 1.4:1;
      (ii.2) hydrothermally synthesizing a titanium-containing zeolitic material having an MWW framework structure from the aqueous synthesis mixture prepared in (ii.1), obtaining a mother liquor comprising the titanium-containing zeolitic material having an MWW framework structure;
   (iii) spray-drying the mother liquor obtained from (ii.2) comprising the titanium-containing zeolitic material having an MWW framework structure.

2. The process of embodiment 1, wherein in (ii.1), the MWW template compound is selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, the MWW template compound preferably being piperidine.

3. The process of embodiment 1 or 2, wherein in (ii.1), the titanium source is selected from the group consisting of tetrabutylorthotitanate, tetraisopropylorthotitanate, tetraethylorthotitanate, titanium dioxide, titanium tetrachloride, titanium tert-butoxide, and a mixture of two or more thereof, the titanium source preferably being tetrabutylorthotitanate.

4. The process of any of embodiments 1 to 3, wherein in the aqueous synthesis mixture in (ii.1), the molar ratio of Ti, calculated as $TiO_2$ and contained in the titanium source, relative to Si, calculated as $SiO_2$ and contained in the zeolitic material having a molar ratio $B_2O_3:SiO_2$ of at most 0.02:1, is in the range of from 0.005:1 to 0.1:1, preferably from 0.01:1 to 0.08:1, more preferably from 0.02:1 to 0.06:1.

5. The process of any of embodiments 1 to 4, wherein in the aqueous synthesis mixture in (ii.1), the molar ratio of $H_2O$ relative to Si, calculated as $SiO_2$ and contained in the zeolitic material having a molar ratio $B_2O_3:SiO_2$ of at most 0.02:1, is in the range of from 8:1 to 20:1, preferably from 10:1 to 18:1, more preferably from 12:1 to 16:1.
6. The process of any of embodiments 1 to 5, wherein in the aqueous synthesis mixture in (ii.1), the molar ratio of the MWW template compound relative to Si, calculated as $SiO_2$ and contained in the zeolitic material provided in (i), is in the range of from 0.5:1 to 1.7:1, preferably from 0.8:1 to 1.5:1, more preferably from 1.0:1 to 1.3:1.
7. The process of any of embodiments 1 to 6, wherein in (ii.2), the hydrothermal synthesizing is carried out at a temperature in the range of from 80 to 250° C., preferably from 120 to 200° C., more preferably from 160 to 180° C.
8. The process of any of embodiments 1 to 7, wherein in (ii.2), the hydrothermal synthesizing is carried out for a period in the range of from 10 to 100 h, more preferably from 20 to 80 h, more preferably from 40 to 60 h.
9. The process of any of embodiments 1 to 8, wherein in (ii.2), the hydrothermal synthesizing is carried out in a closed system under autogenous pressure.
10. The process of any of embodiments 1 to 9, wherein neither during (ii.2), nor after (ii.2) and before (iii), the titanium-containing zeolitic material having an MWW framework structure is separated from its mother liquor.
11. The process of any of embodiments 1 to 10, wherein the mother liquor subjected to (iii) comprising the titanium-containing zeolitic material having an MWW framework structure has a solids content, optionally after concentration or dilution, in the range of from 5 to 25 weight-%, more preferably from 10 to 20 weight-%, based on the total weight of the mother liquor comprising the titanium-containing zeolitic material.
12. The process of any of embodiments 1 to 11, wherein during spray-drying in (iii), the drying gas inlet temperature is in the range of from 200 to 350° C. and the drying gas outlet temperature is in the range of from 70 to 190° C.
13. The process of any of embodiments 1 to 12, wherein the zeolitic material having an MWW framework structure obtained from (iii) has a Si content in the range of from 30 to 40 weight-%, calculated as elemental Si, a total organic carbon content (TOC) in the range of from 0 to 14 weight-%, and a Ti content of from 2.1 to 2.8 weight-%, calculated as elemental titanium, in each case based on the total weight of the zeolitic material.
14. The process of any of embodiments 1 to 13, further comprising
(iv) treating the titanium-containing zeolitic material having an MWW framework structure obtained from (iii) with an aqueous solution having a pH of at most 5.
15. The process of embodiment 14, wherein after (iii) and before (iv), the spray-dried titanium-containing zeolitic material having an MWW framework structure obtained from (iii) is not subjected to calcination.
16. The process of embodiment 14 or 15, wherein in (iv), the weight ratio of the aqueous solution relative to the titanium-containing zeolitic material having an MWW framework structure is in the range of from 10:1 to 30:1, preferably from 15:1 to 25:1, more preferably from 18:1 to 22:1.
17. The process of any of embodiments 14 to 16, wherein in (iv), the aqueous solution comprises an inorganic acid, preferably selected from the group consisting of phosphoric acid, sulphuric acid, hydrochloric acid, nitric acid, and a mixture of two or more thereof, the aqueous solution preferably comprising nitric acid.
18. The process of any of embodiments 14 to 17, wherein in (iv), the aqueous solution has a pH in the range of from 0 to 5, preferably from 0 to 3, more preferably from 0 to 2.
19. The process of any of embodiments 14 to 18, wherein in (iv), the titanium-containing zeolitic material having an MWW framework structure is treated with the aqueous solution at a temperature in the range of from 50 to 175° C., preferably from 70 to 125° C., more preferably from 95 to 105° C.
20. The process of any of embodiments 14 to 19, wherein in (iv), the titanium-containing zeolitic material having an MWW framework structure is treated with the aqueous solution for a period in the range of from 0.1 to 6 h, preferably from 0.3 to 2 h, more preferably from 0.5 to 1.5 h.
21. The process of any of embodiments 14 to 20, wherein the treating according to (iv) is carried out in a closed system under autogenous pressure.
22. The process of any of embodiments 14 to 21, further comprising
(v) separating the titanium-containing zeolitic material having an MWW framework structure obtained from (iv) from the aqueous solution, optionally followed by washing the separated titanium-containing zeolitic material having an MWW framework.
23. The process of embodiment 22, wherein (v) comprises drying the separated and optionally washed titanium-containing zeolitic material having an MWW framework structure.
24. The process of any of embodiments 14 to 23, further comprising
(vi) preparing a suspension, preferably an aqueous suspension containing the titanium-containing zeolitic material having an MWW framework structure obtained from (iv), preferably from (v), said suspension having a solids content preferably in the range of from 5 to 25 weight-%, more preferably from 10 to 20 weight-%, based on the total weight of the suspension, and subjecting the suspension to spray-drying.
25. The process of embodiment 24, wherein during spray-drying, the drying gas inlet temperature is in the range of from 200 to 330° C. and the drying gas outlet temperature is in the range of from 120 to 180° C.
26. The process of any of embodiments 14 to 25, further comprising
(vii) calcining the titanium containing zeolitic material having an MWW framework structure obtained from (iv), preferably from (v), more preferably from (vi), wherein the calcining is preferably carried out at a temperature in the range of from 400 to 800° C., more preferably from 600 to 700° C.
27. The process of embodiment 26, wherein in (vii), the calcining is carried out in continuous mode, preferably with a rate in the range of from 0.2 to 2.0 kg zeolitic material per hour, more preferably from 0.5 to 1.5 kg zeolitic material per hour.

According to the present invention, the TiMWW obtained has a Ti content preferably in the range of from 1.3 to 1.9 weight-%, more preferably from 1.4 to 1.8 weight-%, calculated as elemental Ti. Further, the TiMWW obtained has a Si content preferably in the range of from 39.5 to 45.5 weight-%, more preferably from 40.5 to 44.5 weight-%, calculated as elemental Si. Further, the TiMWW obtained has a C content (total organic carbon, TOC) preferably in the range of from 0.10 to 0.25 weight-%, more preferably from 0.11 to 0.20 weight-%, more preferably from 0.13 to 0.18 weight-%, calculated as elemental C. More preferably, the B-MWW obtained has a C content (total organic carbon, TOC) of less than 0.3 weight-%, more preferably less than 0.2 weight-%, more preferably less than 0.1 weight-%.

Stage (V)

According to stage (V), the TiMWW preferably obtained according to stage (IV) is subjected to a suitable Zn treatment to obtain the ZnTiMWW used for the preparation of the suspension according to (i).

Generally, as far as (V) is concerned, no specific restrictions exist provided that above-defined preferred ZnTiMWW can be obtained having the preferred Zn and Ti content. Most preferably, stage (V) comprises at least one suitable impregnation stage, more preferably at least one wet impregnation stage.

Concerning this impregnation stage, it is preferred to contact the TiMWW preferably as obtained according to (IV) is contacted with at least one suitable Zn-containing precursor in at least one suitable solvent (wet impregnation), most preferably water. As suitable Zn-containing precursor, water-soluble Zn salts are especially preferred, with zinc acetate dihydrate being especially preferred. It is further preferred to prepare a solution of the Zn-containing precursor, preferably an aqueous solution, and to suspend the TiMWW in this solution.

Further preferably, impregnation is carried out at elevated temperatures, relative to room temperature, preferably in the range of from 75 to 125° C., more preferably from 85 to 115° C., for a time preferably in the range of from 3.5 to 5 h, more preferably from 3 to 6 h. Stirring the suspension during impregnation is preferred.

After the impregnation, the obtained ZnTiMWW is preferably suitably separated from the suspension. All methods of separating the ZnTiMWW from the suspension are conceivable. Especially preferably, separation is carried out via filtration, ultrafiltration, diafiltration or centrifugation methods. A combination of two or more of these methods can be applied. According to the present invention, the ZnTiMWW is preferably separated from the suspension by filtration to obtain a filter cake which is preferably subjected to washing, preferably with water. If washing is applied, it may be preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm.

Subsequently, the preferably washed filter cake is subjected to pre-drying, for example by subjecting the filter cake to a suitable gas stream, preferably a nitrogen stream, for a time preferably in the range of from 5 to 15 h, more preferably from 8 to 12.

According to the present invention, the ZnTiMWW obtained from impregnation, preferably washing, and preferably pre-drying, has a Zn content preferably in the range of from 1.0 to 2.0 weight-%, more preferably from 1.1 to 1.7 weight-%, more preferably from 1.2 to 1.6 weight-%, more preferably from 1.3 to 1.5 weight-%, calculated as elemental Zn. Further, the ZnTiMWW obtained has a Ti content preferably in the range of from 1.0 to 2.0 weight-%, more preferably from 1.3 to 1.9 weight-%, more preferably from 1.4 to 1.8 weight-%, more preferably from 1.5 to 1.7 weight-%, calculated as elemental Ti. Further, the ZnTiMWW obtained has a Si content preferably in the range of from 39 to 45 weight-%, more preferably from 40 to 44 weight-%, more preferably from 41 to 43 weight-%, calculated as elemental Si. Further, the ZnTiMWW obtained has a C content (total organic carbon, TOC) preferably in the range of from 1.1 to 1.7 weight-%, more preferably from 1.2 to 1.6 weight-%, more preferably from 1.3 to 1.5 weight-%, calculated as elemental C.

Therefore, the present invention also relates to above-defined process, wherein the ZnTiMWW according to (i) contains zinc in an amount of from 1.0 to 2.0 weight-%, preferably of from 1.1 to 1.7 weight-%, more preferably of from 1.2 to 1.6 weight-%, more preferably of from 1.3 to 1.5 weight-%, calculated as Zn, and titanium in an amount of from 1.0 to 2.0 weight-%, preferably from 1.3 to 1.9 weight-%, preferably of from 1.4 to 1.8 weight-%, more preferably of from 1.5 to 1.7 weight-%, calculated as Ti and based on the weight of the ZnTiMWW.

The Impregnated ZnTiMWW as Such

In this context, it is noted that in JP 2008-200553 A, only ZnTiMWW is disclosed having either a high or a low Zn content. Compared to these values, the ZnTiMWW material according to the present invention has a Zn content in a narrow range of from 1.0 to 2.0 weight-%, preferably from 1.2 to 1.9 weight-% such as of from 1.1 to 1.7 weight-%, or of from 1.2 to 1.6 weight-%, or of from 1.3 to 1.5 weight-%, calculated as elemental Zn and based on the weight of the ZnTiMWW, which narrow Zn content was surprisingly found to allow for very good catalytic results if the ZnTiMWW is used as catalyst, either as such, or in the form of a micropowder containing the ZnTiMWW as such, or in the form of a molding containing said micropowder, in particular if used as catalytically active agent for the preparation of propylene oxide from propene, more preferably for the preparation of propylene oxide from propene in acetonitrile as solvent, more preferably for the preparation of propylene oxide from propene in acetonitrile as solvent using hydrogen peroxide as oxidizing agent.

Specifically, it was found that this narrow Zn content range allows for said catalytic results if, at the same time, the Ti content of the ZnTiMWW is in the range of from 1.0 to 2.0 weight-%, preferably from 1.2 to 1.9 weight-%, such as of from 1.4 to 1.8 weight-%, or of from 1.5 to 1.7 weight-%, calculated as elemental Ti and based on the weight of the ZnTiMWW.

Therefore, according to a general aspect, the present invention relates to a microporous aluminum-free zeolitic material of structure type MWW containing titanium and zinc (ZnTiMWW), having a Zn content in the range of from 1.0 to 2.0 weight-%, preferably of from 1.2 to 1.9 weight-%, calculated as elemental Zn and based on the weight of the ZnTiMWW.

Also, the present invention relates to said microporous aluminum-free zeolitic material of structure type MWW containing titanium and zinc (ZnTiMWW), having a Zn content in the range of from 1.0 to 2.0 weight-%, from 1.2 to 1.9 weight-% such as of from 1.1 to 1.7 weight-%, or of from 1.2 to 1.6 weight-%, or of from 1.3 to 1.5 weight-%, calculated as elemental Zn and based on the weight of the ZnTiMWW, additionally having a Ti content of the ZnTiMWW is in the range of from 1.0 to 2.0 weight-%, preferably from 1.3 to 1.9 weight-%, more preferably of from 1.4 to 1.8 weight-%, such as of from 1.5 to 1.7 weight-%, calculated as elemental Ti and based on the weight of the ZnTiMWW.

Yet further, the present invention relates to a process for the preparation of microporous aluminum-free zeolitic material of structure type MWW containing titanium and zinc (ZnTiMWW), in particular for the preparation of above-described ZnTiMWW, comprising (I) preparing an aluminum-free zeolitic material of structure type MWW containing boron (B-MWW);
(II) deboronating the B-MWW to obtain an aluminum-free zeolitic material of structure type MWW (MWW);

(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation to obtain the ZnTiMWW;
wherein stages (I) to (V) are as defined above.

If the ZnTiMWW is to be used as such, it is conceivable to subject the preferably pre-dried impregnated ZnTiMWW to a drying stage according to which the preferably pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. It is to be understood that in this specific context of the present invention, drying is not carried out via a rapid-drying method such as spray-drying but via conventional drying such as drying the ZnTiMWW in a suitable oven or the like.

After drying, the ZnTiMWW may be subjected to calcination at temperatures in the range of from 400 to 700° C., preferably from 500 to 700° C., more preferably from 550 to 675° C., more preferably from 625 to 675° C. in a suitable atmosphere such as technical nitrogen, air, or lean air, preferably in air or lean air. This calcination is preferably carried out in a muffle furnace, rotary furnace and/or a belt calcination furnace, wherein the calcination is generally carried out for 0.5 hour or more, for example for a time in the range of from 0.25 to 12 hours, preferably of from 0.5 to 6 hours. During calcination, it is possible to keep the temperatures constant or to change the temperatures continuously or discontinuously. If calcination is effected twice or more often, the calcination temperatures in the individual steps may be different or identical.

If used as catalytically active agent, it is especially preferred that the ZnTiMWW as such, or the catalyst such as a micropowder or a molding containing the ZnTiMWW as such and/or said micropowder, is essentially free of noble metals. Therefore, according to particularly preferred embodiment of the present invention, the ZnTiMWW as such and as described above, comprises, based on the total weight of the ZnTiMWW and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.

Yet further, the present invention relates to a process for the preparation of microporous aluminum-free zeolitic material of structure type MWW containing titanium and zinc (ZnTiMWW), in particular for the preparation of above-described ZnTiMWW, comprising
(I) preparing an aluminum-free zeolitic material of structure type MWW containing boron (B-MWW);
(II) deboronating the B-MWW to obtain an aluminum-free zeolitic material of structure type MWW (MWW);
(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation to obtain the ZnTiMWW; wherein stages (I) to (V) are as defined above.

Thus, this general aspect of the present invention is further defined by the following embodiments and the combination of embodiments characterized by the respective dependencies:

1. A microporous aluminum-free zeolitic material of structure type MWW containing titanium and zinc (ZnTiMWW), having a Zn content in the range of from 1.0 to 2.0 weight-%, calculated as elemental Zn and based on the weight of the ZnTiMWW.
2. The ZnTiMWW of embodiment 1, having a Zn content in the range of from 1.2 to 1.9 weight-% such as of from 1.1 to 1.7 weight-%, of from 1.2 to 1.6 weight-%, calculated as elemental Zn and based on the weight of the ZnTiMWW.
3. The ZnTiMWW of embodiment 1 or 2, having a Ti content in the range of from 1.0 to 2.0 weight-%, calculated as elemental Ti and based on the weight of the ZnTiMWW.
4. The ZnTiMWW of any of embodiments 1 to 3, having a Ti content in the range of from 1.3 to 1.9 weight-%, preferably of from 1.4 to 1.8 weight-%, calculated as elemental Ti and based on the weight of the ZnTiMWW.
5. The ZnTiMWW of any of embodiments 1 to 4, having a Zn content in the range of from 1.3 to 1.5 weight-%, calculated as elemental Zn and based on the weight of the ZnTiMWW, and having a Ti content in the range of from 1.5 to 1.7 weight-%, calculated as elemental Ti and based on the weight of the ZnTiMWW.
6. The ZnTiMWW of any of embodiments 1 to 5, comprising, based on the total weight of the ZnTiMWW and calculated as element, less than 0.001 weight-%, preferably less than 0.0001 weight-% of a noble metal selected from the group consisting of gold, platinum, and a mixture of two or more thereof.
7. The ZnTiMWW of embodiment 6, wherein the noble metal is selected from the group consisting of gold, silver, platinum, palladium, iridium, ruthenium, osmium, and a mixture of two or more thereof.
8. The ZnTiMWW of any of embodiments 1 to 7, being contained in a micropowder and/or in a molding.
9. The ZnTiMWW of embodiment 8, wherein the particles of the micropowder have a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of the ZnTiMWW.
10. The ZnTiMWW of embodiment 8, wherein the molding comprises the micropowder as defined in embodiment 9, the molding preferably further comprising at least one binder, preferably a silica binder.
11. A process for the preparation of a microporous aluminum-free zeolitic material of structure type MWW containing titanium and zinc (ZnTiMWW), preferably for the preparation of the ZnTiMWW according to any of embodiments 1 to 7, the process comprising
(I) preparing an aluminum-free zeolitic material of structure type MWW containing boron (B-MWW);
(II) deboronating the B-MWW to obtain an aluminum-free zeolitic material of structure type MWW (MWW);
(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation, preferably wet impregnation, to obtain the ZnTiMWW.
12. The process of embodiment 11, further comprising
(VI) separating the ZnTiMWW from the impregnation solution, preferably by filtration, optionally comprising pre-drying the separated ZnTiMWW.
13. The process of embodiment 12, further comprising
(VII) drying the ZnTiMWW obtained from (VI), preferably at a temperature in the range of from 100 to 300° C.

14. The process of embodiment 13, wherein drying the ZnTiMWW is not carried out via spray-drying, preferably not carried out according to a rapid-drying method.
15. The process of any of embodiments 12 to 14, further comprising
    (VIII) calcining the ZnTiMWW obtained from (VI) or (VII), preferably at a temperature in the range of from 400 to 700° C.
16. A microporous aluminum-free zeolitic material of structure type MWW containing titanium and zinc (Zn-TiMWW), obtainable or obtained by the process according to any of embodiments 11 to 15.
17. Use of the microporous aluminum-free zeolitic material of structure type MWW containing titanium and zinc (Zn-TiMWW) according to any of embodiments 1 to 10 or 16 as catalytically active agent for the preparation of propylene oxide from propene, preferably in acetonitrile as solvent and/or preferably using hydrogen peroxide as oxidizing agent.
18. Use of the microporous aluminum-free zeolitic material of structure type MWW containing titanium and zinc (Zn-TiMWW) according to any of embodiments 1 to 7 or 16 as starting material for the preparation of a micropowder, preferably a micropowder as defined in embodiment 9.
19. Use of the microporous aluminum-free zeolitic material of structure type MWW containing titanium and zinc (Zn-TiMWW) according to any of embodiments 1 to 7, 9, or 16 as starting material for the preparation of a molding, the molding preferably further comprising at least one binder, preferably a silica binder.
20. A process for the preparation of propylene oxide from propene, preferably in acetonitrile as solvent and/or preferably using hydrogen peroxide as oxidizing agent, wherein the microporous aluminum-free zeolitic material of structure type MWW containing titanium and zinc (Zn-TiMWW) according to any of embodiments 1 to 10 or 16 is employed as catalyst.

The Suspension Provided in (i)

As discussed hereinabove, it is generally conceivable that the micropowder of the present invention contains the ZnTiMWW in arbitrary amounts. For example, it may be conceivable that the micropowder, apart from the ZnTiMWW, further contains at least one chemical compound acting as binder material. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxy-aluminates, such as, for example, aluminum triisopropylate, are particularly preferred as $Al_2O_3$ binders. Further conceivable binders might be amphiphilic compounds having a polar and a non-polar moiety and graphite.

Further binders might be, for example, clays, such as, for example, montmorillonites, kaolins, metakaoline, hectorite, bentonites, halloysites, dickites, nacrites or anaxites. According to this conceivable embodiment, the micropowder may contain, based on the weight of the micropowder, up to 95 weight-% or up to 90 weight-% or up to 85 weight-% or up to 80 weight-% or up to 75 weight-% or up to 70 weight-% or up to 65 weight-% or up to 60 weight-% or up to 55 weight-% or up to 50 weight-% or up to 45 weight-% or up to 40 weight-% or up to 35 weight-% or up to 30 weight-% or up to 25 weight-% or up to 20 weight-% or up to 15 weight-% or up to 10 weight-% or up to 5 weight-% of one or more binder materials.

These binders can be used as such or in the form of suitable precursor compounds which, either during spray-drying and/or the subsequent calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, may be preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 $m^2$/g. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Fransil® or Arc-Silica®. Inter alia, an ammoniacal solution of colloidal silica can be used according to the present invention.

According to a preferred embodiment of the present invention, no binder and no binder precursor is added to the micropowder containing ZnTiMWW when the suspension is prepared according to (i). Thus, according to a preferred embodiment of the present invention, the micropowder which is subjected to spray-drying according to (ii) does not contain a binder or a precursor of a binder.

If desired, at least on pore forming agent can be added when the suspension according to (i) is prepared. Pore forming agents which may be used are all compounds which, with regard to the micropowder produced, preferably provide the specific pore characteristics of the micropowder as defined hereinabove. Pore forming agents which may be used are preferably polymers which are dispersible, suspendable or emulsifiable in water or in aqueous solvent mixtures. Such polymers may be polymeric vinyl compounds, such as, for example, polyalkylene oxides, such as polyethylene oxides, polystyrene, polyacrylates, polymethacrylates, polyolefins, polyamides and polyesters, carbohydrates, such as, for example, cellulose or cellulose derivatives, such as, for example, methyl cellulose, or sugars or natural fibers. Further suitable pore forming agents may be, for example, pulp or graphite. If desired with regard the pore characteristics to be achieved, a mixture of two or more pore forming agents may be used. The pore forming agents can be removed by calcination according to (iii) to give the micropowder.

According to a preferred embodiment of the present invention, no pore forming agent is added to the micropowder containing ZnTiMWW when the suspension is prepared according to (i). Thus, according to a preferred embodiment of the present invention, the micropowder which is subjected to spray-drying according to (ii) does not contain a pore forming agent.

As far as the content of the suspension provided in (i) with regard to the ZnTiMWW is concerned, no specific restrictions exist. Preferably, such concentrations are chosen which allow for the preparation of the micropowder as discussed hereinabove. Preferably, the suspension provided in (i) has a solid content in the range of from 5 to 25 weight-%, preferably of from 10 to 20 weight-%. Preferred ranges are from 10 to 15 weight-% or from 11 to 16 weight-% or from 12 to 17 weight-% or from 13 to 18 weight-% or from 14 to 19 weight-% or from 15 to 20 weight-%.

When providing the suspension, the ZnTiMWW can be suspended in any suitable liquid or mixture of two or more liquids. Preferably, the ZnTiMWW is suspended in water or in a mixture of water and at least one further suitable liquid. Most preferably, the ZnTiMWW is suspended in water as sole liquid. Therefore, the suspension provided in (i) is preferably an aqueous suspension.

Therefore, according to a preferred embodiment, the suspension provided in (i) and subjected to spray-drying in (ii) essentially consists of the ZnTiMWW provided as discussed hereinabove, and water. Preferably, the content of the suspension, provided in (i) and subjected to spray-drying in (ii), with regard to both ZnTiMWW and water is at least 95 weight-%, more preferably at least 99 weight-%, more preferably at least 99.9 weight-%, based on the total weight of the suspension.

The Spray-Drying According to (ii)

According to (ii), the suspension provided in (i) is subjected to spray-drying.

Generally, spray-drying is a direct method of drying for example slurries or suspensions by feeding a well-dispersed liquid-solid slurry or suspension a suitable atomizer and subsequently flash-drying in a stream of hot gas. Thereby, the slurry or suspension is continuously passed over nozzles, atomizing discs or other suitable atomizing means (reference is made, for example, to Arthur Lefebvre, "Atomisation and Sprays", Hemisphere Publishing Corporation, 1989, ISBN 0-89116-603-3) and sprayed into a drying chamber which is suitably heated with at least one hot gas. Spray-drying is generally carried out continuously, either without or with (agglomerating mode) returning the solid to the spraying compartment. Spray-drying is disclosed, for example, in K. Masters, "Spray Drying Handbook", Longman Scientific & Technical, 1991, ISBN 0-582-06266-7. The atomizer mentioned above can be of several different types. Most common is wheel atomization which uses high-speed rotation of a wheel or a disc to break up the slurry into droplets that spin out from the wheel into a chamber and are flash-dried prior to hitting the chamber walls. The atomization may also be accomplished by single-component nozzles which rely on hydrostatic pressure to force the slurry through a small nozzle. Multi-component nozzles such as two-component nozzles are also used, where gas pressure is used to force the slurry through the nozzle. The use of a rotating sprayer is also conceivable.

According to the present invention, it is especially preferred to employ a drying gas having a temperature in the range of from 100 to 500° C., preferably in the range of from 150 to 450° C., more preferably in the range of from 200 to 400° C., more preferably in the range of from 250 to 350° C., more preferably in the range of from 275 to 325° C. As drying gas, air, lean air or oxygen-nitrogen mixtures with an oxygen content of up to 10 vol. %, preferably of up to 5 vol. %, more preferably of less than 5 vol. %, as, for example, of up to 2 vol. %, may be employed. It is preferred to use inert gases as drying gas. Technical nitrogen is especially preferred as drying gas. The flow rate of the drying gas is preferably in the range of from 400 to 700 kg/h, more preferably from 500 to 600 kg/h, more preferably from 525 to 575 kg/h such as 525, 530, 535, 540, 545, 550, 555, 560, 565, 570, or 575 kg/h.

According to the present invention, it is especially preferred to employ a nozzle gas having a temperature in the range of from 10 to 100° C., preferably in the range of from 15 to 75° C., more preferably in the range of from 20 to 50° C., more preferably in the range of from 20 to 30° C. As nozzle gas, air, lean air or oxygen-nitrogen mixtures with an oxygen content of up to 10 vol. %, preferably of up to 5 vol. %, more preferably of less than 5 vol. %, as, for example, of up to 2 vol. %, may be employed. It is preferred to use inert gases as nozzle gas. Technical nitrogen is especially preferred as nozzle gas. The flow rate of the nozzle gas is preferably in the range of from 10 to 50 kg/h, more preferably from 15 to 35 kg/h, more preferably from 20 to 25 kg/h.

As nozzle, a two-component nozzle is especially preferred. In particular, such a two-component nozzle has a diameter in the range of from 2 to 6 mm, preferably from 3 to 5 mm, more preferably from 3.5 to 4.5 mm, more preferably from 3.9 to 4.1 mm, more preferably of 4 mm.

Further, it is preferred to use a spray tower configured with a dehumidifier, a filter, and a scrubber, preferably in this sequence, through which configuration the drying gas together with the slurry to be sprayed is passed. According to this embodiment, the temperature of the drying gas as described hereinabove is to be understood as the initial temperature of the drying gas which is passed to the dehumidifier.

Therefore, the present invention relates to above-defined process, wherein in (ii), a spray-apparatus, preferably a spray-tower is used for spray-drying the suspension, said apparatus having at least one spray-nozzle, preferably at least one two-substance nozzle, more preferably one two-substance nozzle, said nozzle having a diameter in the range of from 3.5 to 4.5 mm, preferably from 3.9 to 4.1 mm.

Further, the present invention relates to said process, wherein in (ii), a spray-apparatus, preferably a spray-tower is used for spray-drying the suspension, said apparatus being operated with a nozzle gas having a temperature in the range of from 20 to 50° C., preferably of from 20 to 30° C., and a drying gas having a temperature in the range of from 250 to 350° C., preferably of from 275 to 325° C., said nozzle gas preferably being an inert gas, more preferably technical nitrogen, and said drying gas preferably being an inert gas, more preferably technical nitrogen.

The micropowder which is obtained from (ii) has a residual moisture content of preferably at most, more preferably less than 5 weight-%, more preferably of at most, more preferably less than 4 weight-%, more preferably of at most, more preferably less than 3 weight-%, more preferably of at most, more preferably less than 2 weight-%.

Further, the present invention also relates to the micropowder, obtainable or obtained by the process as discussed above.

The Calcination According to (iii)

According to (iii), the micropowder obtained from (ii) is optionally calcined. According to the present invention, it is preferred to subject the micropowder obtained from (ii) to calcination.

The calcination of the micropowder can be effected under any suitable gas atmosphere, wherein air and/or lean air is/are preferred. Furthermore, the calcination is preferably carried out in a muffle furnace, rotary furnace and/or a belt calcination furnace, wherein the calcination is generally carried out for 0.5 hour or more, for example for a time in the range of from 0.5 to 12 hours, preferably from 0.5 to 6 hours, more preferably from 1 to 3 hours. During calcination, it is possible to keep the temperatures constant or to change the temperatures continuously or discontinuously. If calcination is effected twice or more often, the calcination temperatures in the individual steps may be different or identical. The calcination temperatures are preferably in the range of from up to 700° C., preferably from 400 to 700° C., more preferably from 500 to 700° C., more preferably from 600 to 700° C., more preferably from 625 to 675° C. such as from 625 to 645° C. or from 635 to 655° C. or from 645 to 665° C. or from 655 to 675° C.

Therefore, the present invention relates to above-defined process, wherein in (iii), the micropowder is calcined at a temperature in the range of from 600 to 700° C. for a duration in the range of from 0.5 to 6 h.

Further, the present invention also relates to the micropowder, obtainable or obtained by the process as discussed above.

The micropowder as described above, preferably obtained from the process as described above, can be used as such for every conceivable purpose. According to a preferred embodiment, the micropowder is used as a catalyst, preferably as a catalyst in epoxidation reactions, more preferably as a catalyst for preparing propylene oxide from propene, more preferably as a catalyst for preparing propylene oxide from propene with hydrogen peroxide as oxidizing agent, more preferably as a catalyst for preparing propylene oxide from propene with hydrogen peroxide as oxidizing agent in acetonitrile as solvent.

Therefore, the present invention also relates to the use of the micropowder as described above, preferably obtained from the process as described above, as a catalyst, preferably as a catalyst in epoxidation reactions, more preferably as a catalyst for preparing propylene oxide from propene, more preferably as a catalyst for preparing propylene oxide from propene with hydrogen peroxide as oxidizing agent, more preferably as a catalyst for preparing propylene oxide from propene with hydrogen peroxide as oxidizing agent in acetonitrile as solvent.

Also, the present invention relates to an epoxidation process, preferably to a process for the preparation of propylene oxide from propene, more preferably to a process for the preparation of propylene oxide from propene with hydrogen peroxide as oxidizing agent, more preferably to a process for the preparation of propylene oxide from propene with hydrogen peroxide as oxidizing agent in acetonitrile as solvent, in which process the micropowder as described above, preferably obtained from the process as described above is employed as catalyst.

According to a preferred embodiment of the present invention, the micropowder as discussed above, preferably obtainable or obtained by the process as discussed above, is used as an intermediate for the preparation of a catalyst, more preferably as an intermediate for the preparation of a catalyst molding.

The Molding

Therefore, the present invention also relates to a molding comprising the micropowder, as described above, preferably obtainable or obtained from the process as described above. In particular, the present invention relates to a molding comprising a micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW). Preferably, the molding further comprises at least one binder, preferably a silica binder.

Further, more generally, the present invention also relates to a molding comprising a micropowder comprising, based on the weight of the micropowder, at least 95 weight-% of a microporous aluminum-free zeolitic material of structure type MWW containing titanium and zinc (ZnTiMWW). Preferably, the molding further comprises at least one binder, preferably a silica binder. According to this embodiment, the micropowder referred to may differ in at least one feature from the micropowder according to the present invention, for example in the Dv10 value and/or the pore characteristics.

Further, even more generally, the present invention also relates to a molding comprising a microporous aluminum-free zeolitic material of structure type MWW containing titanium and zinc (ZnTiMWW). Preferably, the molding further comprises at least one binder, preferably a silica binder. According to this embodiment, the ZnTiMWW may be in the form of a micropowder. In this respect, the micropowder may differ in at least one feature from the micropowder according to the present invention, for example in the Dv10 value and/or the pore characteristics. Further according to this embodiment, the ZnTiMWW may be contained in the molding in a form different from a micropowder; for example, the ZnTiMWW may be contained in the molding in the form of the microporous aluminum-free zeolitic material of structure type MWW containing titanium and zinc (ZnTiMWW) as described in detail in the section "The impregnated ZnTiMWW as such" hereinabove such as the microporous aluminum-free zeolitic material of structure type MWW containing titanium and zinc (ZnTiMWW) as described in the embodiments 1 to 7 in the section "The impregnated ZnTiMWW as such" hereinabove.

Preferably, the molding of the present invention comprises, in addition to the micropores of the ZnTiMWW, mesopores. It was found that the molding, in particular if used as catalyst, is especially useful if mesopores are present which may act as transport pores. Preferably, the mesopores have an average pore diameter (4V/A) in the range of from 5 to 40 nm, more preferably from 10 to 35 nm, more preferably from 15 to 30 nm, more preferably from 20 to 30 nm, as determined by Hg porosimetry according to DIN 66133.

Preferably, the molding of the present invention comprises, in addition to the mesopores and in addition to the micropores of the ZnTiMWW, macropores. Preferably, the macropores have an average pore diameter (4V/A) in the range of from 0.04 to 3 micrometer, more preferably from 0.04 to 2 micrometer, more preferably from 0.04 to 1 micrometer, more preferably from 0.04 to 0.5 micrometer, more preferably from 0.04 to 0.1 micrometer, as determined by Hg porosimetry according to DIN 66133.

It is further preferred that the molding of the present invention has a crystallinity, as determined by XRD analysis, of at least 55%, preferably in the range of from 55 to 75%, more preferably in the range of from 60 to 75%. Each value is to be understood as having a measurement inaccuracy of plus/minus 10%.

As mentioned above, the moldings of the present invention preferably contain a binder, in addition to the ZnTiMWW which is contained in the molding for example as micropowder. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaoline, hectorite, bentonites, halloysites, dickites, nacrites or anaxites. Silica binders are especially preferred.

According to this preferred embodiment, the moldings may contain, based on the weight of the moldings, up to 95 weight-% or up to 90 weight-% or up to 85 weight-% or up to 80 weight-% or up to 75 weight-% or up to 70 weight-% or up to 65 weight-% or up to 60 weight-% or up to 55 weight-% or up to 50 weight-% or up to 45 weight-% or up to 40 weight-% or up to 35 weight-% or up to 30 weight-% or up to 25 weight-% or up to 20 weight-% or up to 15 weight-% or up to 10 weight-% or up to 5 weight-% of one or more binder materials. Preferably, the moldings of the present invention contain from 10 to 50 weight-%, preferably from 15 to 40 weight %, more preferably from 20 to 30 weight-% binder, most preferably a silica binder.

While it is generally conceivable that the moldings of the present invention contain a further compound in addition to the ZnTiMWW which is contained in the moldings, for example, as micropowder which in turn preferably essentially consists of the ZnTiMWW, and in addition to the binder, preferably the silica binder, it is especially preferred that the moldings of the present invention essentially consist of the ZnTiMWW and binder, preferably the silica binder. Therefore, the present invention also relates to the molding as defined above, wherein the ZnTiMWW, preferably the micropowder together with the binder, preferably the silica binder, constitute at least 95 weight-%, preferably at least 99 weight-%, more preferably at least 99.9 weight-% of the molding.

Accordingly, the moldings of the present invention may contain, based on the weight of the moldings, up to 5 weight-% or up to 10 weight-% or up to 15 weight-% or up to 20 weight-% or up to 25 weight-% or up to 30 weight-% or up to 35 weight-% or up to 40 weight-% or up to 45 weight-% or up to 50 weight-% or up to 55 weight-% or up to 60 weight-% or up to 65 weight-% or up to 70 weight-% or up to 75 weight-% or up to 80 weight-% or up to 85 weight-% or up to 90 weight-% or up to 95 weight-% of the ZnTiMWW, for example in the form of the micropowder. Preferably, the moldings of the present invention contain from 50 to 90 weight-%, preferably from 60 to 85 weight %, more preferably from 70 to 80 weight-% of the ZnTiMWW, for example in the form of the micropowder.

Therefore, the present invention also relates to the molding as defined above, said molding containing from 10 to 50 weight-%, preferably from 15 to 40 weight %, more preferably from 20 to 30 weight-% binder, most preferably a silica binder, and from 50 to 90 weight-%, preferably from 60 to 85 weight %, more preferably from 70 to 80 weight-% of the ZnTiMWW, for example in the form of the micropowder as defined above.

Therefore, the present invention also relates to the molding as defined above, said molding containing from 10 to 50 weight-%, preferably from 15 to 40 weight %, more preferably from 20 to 30 weight-% binder, most preferably a silica binder, and from 50 to 90 weight-%, preferably from 60 to 85 weight %, more preferably from 70 to 80 weight-% of the ZnTiMWW, preferably in the form of the micropowder as defined above, wherein the ZnTiMWW, preferably the micropowder, together with the binder, preferably the silica binder, constitute at least 95 weight-%, preferably at least 99 weight-%, more preferably at least 99.9 weight-% of the molding.

Preferably, the moldings of the present invention are used as catalysts, in particular in epoxidation reactions such as, for example, for the preparation of propylene oxide from propene. For such catalytic reactions, it was surprisingly found that the concentration of the silanol groups has a decisive influence on the catalytic properties. Surprisingly, it was found that excellent catalytic properties are obtained in case the concentration of the silanol groups is in the range of from up to 6%. While silanol group concentrations in the range of from more than 3 to 6% represent already very good catalysts, exceptionally good catalysts were found to have silanol group concentrations in the range of up to 3% such as in the range of from 1 to 3% or from 2 to 3%. As to the specific determination of the silanol group concentration, reference is made to Reference Example 3.

Therefore, the present invention also relates to the molding as defined above, comprising the ZnTiMWW, preferably the micropowder as defined above, in an amount in the range of from 70 to 80 weight-% and the silica binder in an amount of from 30 to 20 weight-%, the micropowder together with the silica binder constituting at least 99 weight-%, preferably at least 99.9 of the molding, wherein the molding has a concentration of silanol groups with respect to the total number of Si atoms of at most 6%, preferably at most 3%, as determined according to $^{29}$Si MAS NMR.

As to the geometry of the moldings of the present invention, no specific restrictions exist. In particular, the respective geometry may be chosen depending on the specific needs of the specific use of the moldings. In case the moldings are used as catalysts, geometries such as strands, for example having rectangular, triangular hexagonal, quadratic, oval, or circular cross-section, stars, tablets, spheres, hollow cylinders, and the like are possible. One of the preferred geometries of the moldings of the present invention is a strand having circular cross-section. Such geometries are preferred if the moldings of the present invention are employed, for example, as fixed-bed catalysts, most preferably in continuous-type reactions. The diameter of these strands having circular cross-section which can be prepared, e.g., via extrusion processes, is preferably in a range of from 1 to 4 mm, more preferably from 1 to 3 mm, more preferably from 1 to 2 mm, more preferably from 1.5 to 2 mm, more preferably from 1.5 to 1.7 mm.

For the moldings of the present invention, in particular if used as catalysts such as fixed-bed catalysts, most preferably in continuous-type reactions, it is generally necessary that the moldings have superior mechanic resistance in order to allow for a long-term use in the reactor. Surprisingly, it was found that the moldings of the present invention, preferably in the form of strands having circular cross-section and a diameter of from 1.5 to 1.7 mm, exhibit such excellent mechanical properties. While it was found that such strands according to the present invention have a crush strength of the least 5 N and, thus, generally very good mechanical properties, especially preferred strands of the present invention exhibit a crush strength of up to 20 N, such as from 10 to 20 N, in particular from 11 to 20 N.

Therefore, the present invention also relates to the above-described molding being a strand having circular cross-section a diameter in the range of from 1.5 to 1.7 mm and having a crush strength of at least 5 N, preferably in the range of from 5 to 20 N, more preferably in the range of from 11 to 20 N, the crush strength being determined by crush strength test machine Z2.5/TS1S according to the method as described in the description. As to the specific determination of the crush strength, reference is made to Reference Example 2.

Further, it was found in the context of the present invention that moldings are preferred, in particular if used as catalysts, which contain ZnTiMWW, preferably in the form of the micropowder and which are essentially free of noble metals. Therefore, according to particularly preferred embodiment of the present invention, the molding comprises, based on the total weight of the molding and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.

Process for the Preparation of the Molding

Generally, there are no specific restrictions concerning a conceivable process for the preparation of the moldings of the present invention provided that above-defined characteristics can be obtained. According to a preferred embodiment of the present invention, the ZnTiMWW comprised in the molding is present in the form of a micropowder, preferably in the form of the micropowder as defined above.

Therefore, according to preferred embodiment, the present invention relates to a process, in particular to a process for the preparation of molding, the process comprising
(i) providing a suspension containing a microporous aluminum-free zeolitic material of structure type MWW containing titanium and zinc (ZnTiMWW);
(ii) subjecting the suspension provided in (i) to spray-drying to obtain a micropowder;
(iii) optionally calcining the micropowder obtained in (ii),
(iv) shaping the micropowder obtained in (ii) or (iii) to obtain a molding;
(v) optionally drying and/or calcining the molding obtained in (iv).

More preferably, the micropowder obtained from (ii), preferably from (iii), is the micropowder as defined above. According to this embodiment, the present invention relates to a process, in particular to a process for the preparation of molding, the process comprising
(i) providing a suspension containing a microporous aluminum-free zeolitic material of structure type MWW containing titanium and zinc (ZnTiMWW);
(ii) subjecting the suspension provided in (i) to spray-drying to obtain a micropowder;
(iii) calcining the micropowder obtained in (ii) to obtain a micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW),
(iv) shaping the micropowder obtained in (iii) to obtain a molding;
(v) optionally drying and/or calcining the molding obtained in (iv).

The shaping according to (iv) may be performed according to any conceivable manner provided that a molding is obtained comprising the micropowder as indicated, preferably the molding having above-defined features. Preferably, in a first stage (aa), a formable mass is prepared from the micropowder, and in a subsequent stage (bb), the formable mass is further processed to a molding having the desired geometry.

Therefore, the present invention also relates to above-defined process, wherein the shaping according to (iv) comprises
(aa) mixing the micropowder with a binder or a binder precursor, to obtain a mixture;
(bb) shaping the mixture obtained in (aa) to obtain the molding.

According to (aa), the micropowder is mixed with a binder or a binder precursor to obtain a mixture. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum tri-isopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaoline, hectorite, bentonites, halloysites, dickites, nacrites or anaxites. Silica binders are especially preferred.

These binders can be used as such or in the form of suitable precursor compounds which, either during spray-drying and/or the subsequent calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, may be preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 $m^2/g$. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention.

Especially preferred binder or binder precursors are silica binders or silica binder precursors.

As to the ratio of the amount of micropowder relative to the amount of silica contained in or resulting from the silica binder employed in (aa), it generally can be freely chosen. However, it was found that a specific weight ratio of micropowder relative to silica contained in or resulting from the silica binder (precursor) allows for preparing especially advantageous mixtures. Generally, the weight ratio of the ZnTiMWW contained in the micropowder relative to silica contained in or resulting from the silica binder is in the range of from 1:1 to 1:9, preferably from 2:3 to 1.51:8.5, more preferably from 3:7 to 1:4.

Therefore, the present invention also relates to above-defined process wherein (aa) comprises (aa) mixing the micropowder with a silica binder or a silica binder precursor, wherein the weight ratio of the ZnTiMWW contained in the micropowder relative to silica contained in or resulting from the silica binder is in the range of from 3:7 to 1:4 to obtain a mixture.

In stage (aa), it is further preferred to add at last one pasting agent to provide for an improved processability of the mixture in (bb). Preferred pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, carbohydrates such as cellulose, cellulose derivatives, water and mixtures of two or more of these compounds, such as water and cellulose or water and cellulose derivatives are used as pasting agent. In a particularly preferred embodiment of the process according to the invention, the at least one pasting agent is removed by drying and/or calcination, as further described below.

Therefore, the present invention relates to above-defined process wherein in (aa), a carbohydrate and/or water is/are added as pasting agent.

Preferably, the weight ratio of the ZnTiMWW contained in the micropowder relative to sum of the weight of the pasting agents, preferably water and/or carbohydrate, is in the range of from 1:1 to 1:4, preferably from 3:4 to 1:3. If a combination of water and a carbohydrate is employed as pasting agent, the preferred weight ratio of carbohydrate relative to the water is in the range of from 1:20 to 1:30, more preferably from 1:25 to 1:30.

The order of mixing of the respective components of the mixture according to (aa) can be chosen according to the specific needs. If for example, a combination of the micropowder, a binder, and a pasting agent is employed, it is possible both first to add the micropowder, then the pasting agent, and finally the binder, and to interchange the sequence with regard to the micropowder, the pasting agent, and the binder. According to a preferred embodiment, the micropowder and the carbohydrate are mixed and the binder or binder precursor is added before the water is added.

Surprisingly, it was found that the processability of the mixture obtained from mixing according to (aa) can be optimized by suitably choosing the duration of the mixing process. Especially preferred mixtures were obtained if the duration of the mixing process was between a specific minimum and maximum value, with a range of from 15 to 60 min being preferred, a range of from 30 to 55 min being more preferred, and a range of from 40 to 50 min being especially preferred.

As already discussed above, the moldings of the present invention may be shaped in (bb) in every conceivable geometry such as strands, for example having rectangular, triangular hexagonal, quadratic, oval, or circular cross-section, stars, tablets, spheres, hollow cylinders, and the like. One of the preferred geometries of the moldings of the present invention is a strand having circular cross-section. Such geometries are preferred if the moldings of the present invention are employed, for example, as fixed-bed catalysts, most preferably in continuous-type reactions. The diameters of these strands having circular cross-section are preferably in a range of from 1 to 4 mm, more preferably from 1 to 3 mm, more preferably from 1 to 2 mm, more preferably from 1.5 to 2 mm, more preferably from 1.5 to 1.7 mm. Depending on the specific geometry, the shaping process according to (bb) will be chosen. If, according to a preferred embodiment of the present invention, strands are prepared, the shaping according to (bb) preferably comprises subjecting the mixture obtained in (aa) to extrusion. Suitable extrusion apparatuses are described, for example, in "Ullmann's Enzyklopadie der Technischen Chemie", $4^{th}$ edition, vol. 2, page 295 et seq., 1972. In addition to the use of an extruder, an extrusion press can also be used for the preparation of the moldings. If necessary, the extruder can be suitably cooled during the extrusion process. According to the present invention, extrusion processes are preferred wherein per batch, the power consumption is in the range of from 1 to 10 A, preferably from 1.5 to 6 A, more preferably from 2 to 4 A. The strands leaving the extruder via the extruder die head can be mechanically cut by a suitable wire or via a discontinuous gas stream.

Therefore, the present invention also relates to above-defined process, wherein the shaping according to (iv) comprises (aa) mixing the micropowder with a binder or a binder precursor, preferably a silica binder or a silica binder precursor, wherein the weight ratio of the ZnTiMWW contained in the micropowder relative to silica contained in or resulting from the silica binder is in the range of from 3:7 to 1:4 to obtain a mixture, wherein the duration of the mixing process is preferably in the range of from 15 to 60 min;

(bb) shaping the mixture obtained in (aa) to obtain the molding, said shaping preferably comprising subjecting the mixture obtained in (aa) to extrusion from which preferably strands are obtained having a diameter preferably in the range of from 1.0 to 2.0 mm, more preferably of from 1.5 to 1.7 mm.

Generally, it is conceivable that a pore-forming agent, in particular a mesopore-forming agent is additionally employed in (aa) or added to the mixture obtained from (aa) prior to (bb). Such pore forming agents usually employed are preferably polymeric vinyl compounds, such as, for example, polyalkylene oxides, such as polyethylene oxides, polystyrene, polyacrylates, polymethacrylates, polyolefins, polyamides and polyesters. Such pore-forming agents may be employed if, for example, a ZnTiMWW containing micropowder is employed which differs from the micropowder according to the present invention, in particular with regard to the presence of the mesopores, or if ZnTiMWW is employed in a form different from a micropowder. As already discussed hereinabove, however, the micropowder of the present invention which is preferably used as starting material for the preparation of the inventive molding exhibits the specific Dv10 values and the specific mesopore characteristics which allow for a shaping process wherein none of the above-disclosed pore-forming agents is employed, neither as compound of the mixture obtained from (aa) nor as additive added to the mixture obtained from (aa) prior to (bb), nor as additive added during the shaping process according to (bb).

Therefore, the present invention relates to above-defined process, wherein in (iv), no mesopore-forming agent selected from the group consisting of polyalkylene oxides such as polyethylene oxides, polystyrene, polyacrylates, polymethacrylates, polyolefins, polyamides, and polyesters is added, preferably wherein in (iv) no mesopore-forming agent is added.

The molding obtained from shaping such as from extrusion is preferably dried and/or calcined. No specific restrictions exist concerning drying and calcination conditions provided that a molding is obtained which preferably exhibits above-defined features.

The drying is preferably carried out at temperatures in the range of from 80 to 160° C., more preferably from 90 to 155° C., more preferably from 100 to 150° C., and preferably for a duration in the range of from 6 to 24 h, more preferably from 10 to 20 h. The drying can be effected under any suitable gas atmosphere such as air, lean air, or nitrogen such as technical nitrogen, wherein air and/or lean air are preferred.

The calcination is preferably carried out at temperatures in the range of from 400 to 650° C., more preferably from 450 to 625° C., more preferably from 500 to 600° C., and preferably for a duration in the range of from 0.25 to 6 h, more preferably from 0.5 to 2 h.

The calcination can be effected under any suitable gas atmosphere such as air, lean air, or nitrogen such as technical nitrogen, wherein air and/or lean air are preferred.

Preferably, moldings are obtained from drying and calcination which already exhibit very good characteristics, in particular if used as catalysts as described above. In particular, the moldings obtained according to above-defined process preferably comprise the ZnTiMWW, preferably the micropowder as defined above, in an amount in the range of from 70 to 80 weight-% and the silica binder in an amount of from 30 to 20 weight-%, the micropowder together with the silica binder constituting at least 99 weight-%, preferably at least 99.9 of the molding, wherein the molding has a concentration of silanol groups with respect to the total number of Si atoms in the range of more than 3 to 6% as determined according to $^{29}$Si MAS NMR. Further, the moldings obtained according to above-defined process are preferably in the form of strands having circular cross-section and a diameter of from 1.5 to 1.7 mm and have a crush strength of at least 5 N, preferably in the range of from 5 to 10 N.

Further, the present invention relates to a molding, obtainable or obtained by the process as defined above, comprising steps (iv) and preferably (v), preferably (i), (ii), (iii), (iv) and preferably (v).

Post-Treatment with Water

A further major aspect of the present invention is the fact that it was surprisingly found that by a suitable post-treatment of the molding containing the ZnTiMWW, the characteristics of the moldings such as the concentration of silanol groups and the crush strength which are decisive in particular in case the moldings are employed as catalyst, preferably in epoxidation reactions such as the preparation of propylene oxide from propene, can still be remarkably improved.

Therefore, the present invention relates to above-defined process, further comprising
(vi) subjecting the molding obtained in (iv) or (v), preferably in (v), to a water-treatment;
(vii) optionally drying and/or calcining the water-treated molding.

Therefore, the present invention also relates to a process for the preparation of a molding, said process comprising
(i) providing a suspension containing a microporous aluminum-free zeolitic material of structure type MWW containing titanium and zinc (ZnTiMWW);
(ii) subjecting the suspension provided in (i) to spray-drying to obtain a micropowder;
(iii) calcining the micropowder obtained in (ii) to obtain a micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW);
(iv) shaping the micropowder obtained in (iii) to obtain a molding;
(v) preferably drying and calcining the molding obtained in (iv);
(vi) subjecting the molding obtained in (iv) or (v), preferably in (v), to a water-treatment;
(vii) preferably drying and/or calcining the water-treated molding.

According to a preferred embodiment of the present invention, said water treatment according to (vi) comprises treating the molding with liquid water at a pressure higher than ambient pressure. More preferably, the water treatment is carried out at temperatures higher than ambient temperature, preferably in the range of from 100 to 200° C., more preferably of from 125 to 175° C., more preferably of from 130 to 160° C., more preferably of from 135 to 155° C. more preferably of from 140 to 150° C. Further preferably, the water treatment is carried at these temperatures under autogenous pressure. Still more preferably, the water treatment of the molding is carried out in an autoclave. These temperatures are to be understood as the temperatures in the vessel where the water treatment is carried, for example in the autoclave.

Concerning the duration, it is preferred to carry out the water treatment for a time in the range of from 1 to 48 h, more preferably from 2 to 24 h, more preferably from 3 to 18 h, more preferably from 4 to 16 h, more preferably from 5 to 12 h, more preferably from 6 to 10 h. It was surprisingly found that durations of as low as from 6 to 10 h were sufficient to increase the quality of the moldings to a major extent.

Therefore, the present invention relates to above-defined process, wherein in (vi), the water-treatment comprises treating the molding with liquid water in an autoclave under autogenous pressure at a temperature in the range of from 100 to 200° C., preferably of from 125 to 175° C., more preferably of from 140 to 150° C. for a period of from 2 to 24 hours, preferably of from 6 to 10 h.

The time within which the water and the molding are heated to the above-defined preferred temperatures are generally not subject to any specific restrictions. Preferably, the heating ramp from ambient temperature to the preferred temperature is in the range of from 0.25 to 6 h, preferably from 0.5 to 3 h, more preferably from 1 to 2 h. After the water treatment, the suspension obtained from the water treatment is suitably cooled, preferably within 0.25 to 6 h, more preferably from 0.5 to 4 h, more preferably from 1 to 3 h.

Generally, no specific restrictions exist with regard to the amount of water used for the water treatment of the molding. However, it was found that the weight ratio of the moldings relative to the water used for the water treatment is preferably in the range of from 0.001:1 to 1:1, more preferably from 0.005:1 to 0.5:1, more preferably from 0.01:1 to 0.1:1. Even more preferably, the weight ratio of the moldings relative to the water used for the water treatment is in the range of from 0.02:1 to 0.08:1, more preferably of from 0.03:1 to 0.07:1, more preferably of from 0.04:1 to 0.06:1.

Concerning the order of mixing, no specific restrictions exist. It is conceivable to charge the moldings into the vessel, for example the autoclave, used for the water treatment, and subsequently charge the water into the vessel. Preferably, the water is at least partially charged into the vessel, and subsequently, the moldings are charged into the vessel.

While it may be generally conceivable that, in addition to the molding and the water, further compounds could be added for the purpose of the water treatment, it is especially preferred that no such further compound is employed for the inventive water treatment. Thus, the suspension of the molding and the water according to (vi) essentially consists of the moldings and the water. Therefore, the present invention also relates to above-defined process, wherein at least 95 weight-%, more preferably at least 99 weight-%, more preferably at least 99.9 weight-% of the suspension according to (vi) are comprised of the molding and the water used for the water treatment.

According to the present invention, it may be conceivable to additionally subject the molding to at least one steaming stage such as to steaming using water steam, either prior to or after (vi). However, it is especially preferred to avoid such steaming stage during the process of the present invention. Therefore, the present invention relates to above-defined process, wherein the molding is not subjected to steaming. Thus, preferably, the molding of the present invention is not subjected to steaming prior to, during, or after (vi).

In particular, the present invention relates to above-defined process, wherein in (vi), the water-treatment consists of treating the molding with liquid water in an autoclave under autogenous pressure at a temperature in the range of from 140 to 150° C. for a period of from 6 to 10 h, wherein, in the autoclave, the weight ratio of the molding relative to the water is in the range of from 0.04 to 0.06, and wherein, during the water-treatment, the suspension of the molding in the water is not stirred.

The molding obtained from the water treatment is preferably dried and/or calcined, more preferably dried and calcined according to (vii). No specific restrictions exist concerning drying and calcination conditions provided that a molding is obtained which preferably exhibits above-defined especially preferred features.

The drying according to (vii) is preferably carried out at temperatures in the range of from 80 to 160° C., more preferably from 90 to 155° C., more preferably from 100 to 150° C., and preferably for a duration in the range of from 6 to 24 h, more preferably from 10 to 20 h. The drying can be effected under any suitable gas atmosphere, wherein air and/or lean air are preferred.

The calcination is preferably carried out at temperatures in the range of from 300 to 600° C., more preferably from 350 to 550° C., more preferably from 400 to 500° C., and preferably for a duration in the range of from 0.25 to 6 h, more preferably from 1 to 3 h. The calcination can be effected under any suitable gas atmosphere such a sair, lean air, or nitrogen such as technical nitrogen, wherein air and/or lean air are preferred.

The time within which the molding is heated to the above-defined preferred temperatures is generally not subject to any specific restrictions. Preferably, the heating ramp from ambient temperature to the preferred temperature is in the range of from 0.25 to 10 h, preferably from 1 to 8 h, more preferably from 3 to 6 h. After the calcination, the molding is suitably cooled.

Therefore, the present invention relates to above-defined process, wherein in (vii), the water-treated molding is dried at a temperature in the range of from 100 to 150° C. for a duration in the range of from 10 to 20 h and calcined at a temperature in the range of from 400 to 500° C. for a duration in the range of from 1 to 3 h.

Surprisingly, it was found that above-discussed water treatment has a significant influence on the characteristics of the moldings, in particular the characteristics of the moldings if used as catalysts as described above. In particular, the moldings obtained according to above-defined process preferably comprise the ZnTiMWW, preferably the micropowder as defined above, in an amount in the range of from 70 to 80 weight-% and the silica binder in an amount of from 30 to 20 weight-%, the micropowder together with the silica binder constituting at least 99 weight-%, preferably at least 99.9 weight-% of the molding, wherein the molding has a concentration of silanol groups with respect to the total number of Si atoms of at most 3%, preferably in the range of from 0.5 to 3%, more preferably from 1 to 3%, as determined according to $^{29}$Si MAS NMR. As to the respective measurement, reference is made to Reference Example 3.

Further, the moldings obtained according to above-defined process are preferably in the form of strands having circular cross-section and a diameter of from 1.5 to 1.7 mm preferably have a crush strength in the range of more than 10 N, more preferably from more than 10 to 20 N, more preferably from 11 to 20 N, more preferably from 12 to 20 N. As to the respective measurement, reference is made to Reference Example 2.

Moreover, it was found that using the inventive water treatment has an effect on the molding related to the $Q^3$ and $Q^4$ structures. As described in Reference Example 4, the $^{29}$Si solid-state NMR experiments performed for the material of the moldings of the present invention showed that the intensity of the signals attributed to the $Q^3$ structures (and to the $Q^4$ structures influenced by the $Q^3$ structures) relative to the intensities of the signals attributed to the $Q^4$ structures decreased if the non-water-treated molding of the present invention is subjected to the inventive water treatment. Specifically, after the water treatment of the invention, a decrease of signal intensity at the left hand side of the $^{29}$Si solid-state NMR spectrum was observed, a region that includes $Q^3$ silanol structures. According to especially preferred examples, this left hand side of the spectrum is at or above about −104 ppm. Further, an increase of the signals at the right hand side of the spectrum was observed, which region comprises $Q^4$ structures exclusively. According to especially preferred examples, this right hand side of the spectrum is below about −110 ppm. Such a decrease in the intensity ratio of the signals attributed to silanol structures including $Q^3$ structures relative to the that the signals attributed to silanol structures attributed to $Q^4$ structures indicates that the inventive water treatment has a significant influence on the zeolitic framework structure which change provides, as is shown in the inventive examples, for a molding having better catalytic properties, in particular in case the molding is used as catalyst for the preparation of propylene oxide from propene, preferably using hydrogen peroxide as oxidizing agent, more preferably using hydrogen peroxide as oxidizing agent in acetonitrile a solvent. As to the respective measurement, reference is made to Reference Example 4.

Therefore, the present invention also relates to the molding as described above, the $^{29}$Si-NMR spectrum of said molding comprising six peaks at the following position peak 1 at −98+/−x ppm,
peak 2 at −104+/−x ppm,
peak 3 at −110+/−x ppm,
peak 4 at −113+/−x ppm,
peak 5 at −115+/−x ppm,
peak 6 at −118+/−x ppm, with x in any of the peaks being 1.5, preferably 1.0, more preferably 0.5,
wherein Q which is defined as $$Q=100*\{[a_1+a_2]/[a_4+a_5+a_6]\}/a_3$$

is at most 1.6, preferably at most 1.4 and more preferably at most 1.3, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3.

The present invention also relates to the molding as described above, the $^{29}$Si-NMR spectrum of said molding comprising six peaks at the following positions peak 1 at −98+/−x ppm,
peak 2 at −104+/−x ppm,
peak 3 at −110+/−x ppm,
peak 4 at −113+/−x ppm,
peak 5 at −115+/−x ppm,
peak 6 at −118+/−x ppm, with x in any of the peaks being 1.5, preferably 1.0, more preferably 0.5,
wherein Q which is defined as $$Q=100*\{[a_1+a_2]/[a_4+a_5+a_6]\}/a_3$$

is at most 2.5, preferably at most 1.6, preferably at most 1.4, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3.

Further, it was found that using the inventive water treatment, the hydrophobicity of the molding can be increased. Such an increase in the hydrophobicity and the respectively change in the chemical properties of the molding provides indicates that the inventive water treatment has a significant influence on the properties of the inventive moldings, as is shown in the inventive examples, in particular in case the molding is used as catalyst for the preparation of propylene oxide from propene, preferably using hydrogen peroxide as oxidizing agent, more preferably using hydrogen peroxide as oxidizing agent in acetonitrile a solvent. The term "hydrophobicity" as used in this context of the present application is determined according to the measurement of water adsorption/desorption isotherms. From these isotherms, the water uptake of given molding can be determined, and the lower the water uptake, the higher the hydrophobicity will be. As to the respective measurement, reference is made to Reference Example 6. Generally, a molding of the present has a water uptake in the range of up to 8 weight-%, more preferably from 2 to 8 weight-%, more preferably from 3 to 8 weight-%. The most preferred moldings according to the present invention preferably have a water uptake in the range of from 4 to 7 weight-%, such as from 4.5 to 6.5 weight-%.

Yet further, it was found that the inventive water-treatment had an influence on the silanol group characteristics. In particular, in the (infrared) IR spectrum of the moldings of the present invention, a first type of silanol groups is represented by a band in the region of $(377-3750)+/−20$ cm$^{-1}$, and a second type of silanol groups is represented by a band in the region of $(3670-3690)+/−20$ cm$^{-1}$. According to the present invention, it was found that the intensity ratio of the IR peak representing the silanol groups of the first type relative to the IR peak representing the silanol groups of the second type is preferably decreased by the inventive water treatment to values of at most 1.5, more preferably of at most 1.4. As to the respective measurement, reference is made to Reference Example 5.

Yet further, it was found that the inventive water-treatment had an influence on the silanol group characteristics. In particular, in the (infrared) IR spectrum of the moldings of the present invention, a first type of silanol groups is represented by a band in the region of $3746+/−20$ cm$^{-1}$, and a second type of silanol groups is represented by a band in the region of $3678+/−20$ cm$^{-1}$. According to the present invention, it was found that the intensity ratio of the IR peak representing the silanol groups of the first type relative to the IR peak representing the silanol groups of the second type is preferably decreased by the inventive water treatment to values of at most 1.5, more preferably of at most 1.4, more preferably of at most 1.3, more preferably of at most 1.2. As to the respective measurement, reference is made to Reference Example 5.

Such a decrease in the intensity ratio indicates that the inventive water treatment has a significant influence on the chemical properties of the inventive moldings, as is shown in the inventive examples, in particular in case the molding is used as catalyst for the preparation of propylene oxide from propene, preferably using hydrogen peroxide as oxidizing agent, more preferably using hydrogen peroxide as oxidizing agent in acetonitrile a solvent.

Further, the present invention relates to a molding, obtainable or obtained by the process as defined above, comprising steps (vi) and preferably (vii), more preferably (iv) and preferably (v), (vi) and preferably (vii), preferably (i), (ii), (iii), (iv) and preferably (v), (vi) and preferably (vii).

Generally, the present invention also relates to the use of a water treatment as defined above comprising (vi) and preferably (vii) for improving the catalytic properties of a molding comprising ZnTiMWW as catalytically active material, wherein the molding is preferably employed as catalyst for the preparation of propylene oxide from propene, preferably using hydrogen peroxide as oxidizing agent, more preferably using hydrogen peroxide as oxidizing agent in acetonitrile a solvent.

The molding as described above, preferably obtained from the process as described above, can be used as such for every conceivable purpose. According to a preferred embodiment, the molding is used as a catalyst, preferably as a catalyst in epoxidation reactions, more preferably as a catalyst for preparing propylene oxide from propene, more preferably as a catalyst for preparing propylene oxide from propene with hydrogen peroxide as oxidizing agent, more preferably as a catalyst for preparing propylene oxide from propene with hydrogen peroxide as oxidizing agent in acetonitrile as solvent.

Therefore, the present invention also relates to the use of the molding as described above, preferably obtainable or obtained from the process as described above, as a catalyst, preferably as a catalyst in epoxidation reactions, more preferably as a catalyst for preparing propylene oxide from propene, more preferably as a catalyst for preparing propylene oxide from propene with hydrogen peroxide as oxidizing agent, more preferably as a catalyst for preparing propylene oxide from propene with hydrogen peroxide as oxidizing agent in acetonitrile as solvent, wherein the epoxidation reaction is preferably a continuous reaction, and/or wherein the molding is employed as fixed-bed catalyst, wherein the selectivity with respect to propylene oxide relative to hydrogen peroxide after a run-time of 500 h is preferably at least 95%, preferably at least 96%.

Also, the present invention relates to an epoxidation process, preferably to a process for the preparation of propylene oxide from propene, more preferably to a process for the preparation of propylene oxide from propene with hydrogen peroxide as oxidizing agent, more preferably to a process for the preparation of propylene oxide from propene with hydrogen peroxide as oxidizing agent in acetonitrile as solvent, in which process the molding as described above, preferably obtained from the process as described above is employed as catalyst, wherein the epoxidation process is preferably a continuous process, and/or wherein the molding is employed as fixed-bed catalyst, wherein the selectivity with respect to propylene oxide relative to hydrogen peroxide after a runtime of 500 h is preferably at least 95%, preferably at least 96%.

The present invention is further characterized by the following embodiments, including the combinations of embodiments as indicated by the respective dependencies:

1. A micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW).
2. The micropowder of embodiment 1, having a Dv10 value in the range of from 2 to 5.5 micrometer, preferably from 3 to 5.5 micrometer.
3. The micropowder of embodiment 1 or 2, having a Dv50 value in the range of from 7 to 25 micrometer.
4. The micropowder of any of embodiments 1 to 3, wherein the mesopores have an average pore diameter (4V/A) in the range of from 10 to 50 nm, preferably of from 15 to 40 nm, more preferably of from 20 to 30 nm, as determined by Hg porosimetry according to DIN 66133.
5. The micropowder of any of embodiments 1 to 4, additionally comprising macropores having an average pore diameter (4V/A) in the range of from more than 50 nm, said macropores preferably having an average pore diameter in the range of from 0.05 to 3 micrometer, as determined by Hg porosimetry according to DIN 66133.
6. The micropowder of any of embodiments 1 to 5, wherein the micropores of the ZnTiMWW have an average pore diameter in the range of from 1.0 to 1.2 nanometer as determined by nitrogen adsorption according to DIN 66135.
7. The micropowder of any of embodiments 1 to 6, comprising, based on the weight of the micropowder, at least 99 weight-%, preferably at least 99.7 weight-% of the ZnTiMWW.
8. The micropowder of any of embodiments 1 to 7, wherein the ZnTiMWW contains zinc in an amount of from 1.0 to 2.0 weight-%, preferably of from 1.2 to 1.9 weight-%, calculated as Zn and based on the weight of the ZnTiMWW.
9. The micropowder of any of embodiments 1 to 8, wherein the ZnTiMWW contains titanium in an amount of from 1.0 to 2.0 weight-%, preferably of from 1.2 to 1.8 weight-%, calculated as Ti and based on the weight of the ZnTiMWW.
10. The micropowder of any of embodiments 1 to 9, having a crystallinity, as determined by X-ray diffraction (XRD) analysis, of at least (80+/−10) %, preferably of at least (85+/−10) %.
11. The micropowder of any of embodiments 1 to 10, comprising, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.
12. The micropowder of any of embodiments 1 to 11, comprising, based on the total weight of the micropowder and calculated as element, less than 0.1 weight.-%, preferably less than 0.01 weight-% of boron.
13. The micropowder of any of embodiments 1 to 12, having a bulk density of in the range of from 80 to 100 g/ml.
14. The micropowder of any of embodiments 1 to 13, being a spray powder, preferably obtainable or obtained by spray-drying.
15. The micropowder of any of embodiments 1 to 14, being comprised in a molding, said molding preferably additionally comprising a binder, preferably a silica binder.
16. The micropowder of any of embodiments 1 to 15 for use as a catalyst, or as an intermediate for the preparation of a catalyst, preferably for preparing propylene oxide from propene with hydrogen peroxide as oxidizing agent in acetonitrile as solvent.
17. A molding, comprising a microporous aluminum-free zeolitic material of structure type MWW containing titanium and zinc (ZnTiMWW), said molding preferably comprising a micropowder comprising, based on the weight of the micropowder, at least 95 weight-% of a microporous aluminum-free zeolitic material of structure type MWW containing titanium and zinc (ZnTiMWW), said molding more preferably comprising the micropowder according to any of embodiments 1 to 16, the molding preferably further comprising at least one binder, preferably a silica binder.
18. The molding of embodiment 17, comprising mesopores having an average pore diameter in the range of from 4 to 40 nm, preferably from 20 to 30 nm as determined by Hg porosimetry according to DIN 66133.
19. The molding of embodiment 17 or 18, having a crystallinity, as determined by XRD analysis, of at least (55+/−10)%, preferably in the range of from ((55 to 75)+/−10)%.
20. The molding of any of embodiments 17 to 19, comprising the micropowder in an amount in the range of from 70 to 80 weight-% and the silica binder in an amount in the range of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR.
21. The molding of any of embodiments 17 to 20, being a strand having a circular cross-section and a diameter in the range of from 1.5 to 1.7 mm and having a crush strength of at least 5 N, preferably in the range of from 5 to 20 N, more preferably in the range of from 12 to 20 N, the crush strength being determined by crush strength test machine Z2.5/TS1S according to the method as described in the description.
22. The molding of any of embodiments 17 to 21, the $^{29}$Si-NMR spectrum of said molding comprising six peaks at the following positions
   peak 1 at −98+/−x ppm,
   peak 2 at −104+/−x ppm,
   peak 3 at −110+/−x ppm,
   peak 4 at −113+/−x ppm,
   peak 5 at −115+/−x ppm,
   peak 6 at −118+/−x ppm,
with x in any of the peaks being 1.5, preferably 1.0, more preferably 0.5,
wherein Q which is defined as $$Q=100*\{[a_1+a_2]/[a_4+a_5+a_6]\}/a_3$$

is at most 2.5, preferably at most 1.6, preferably at most 1.4, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3.
23. The molding of any of embodiments 17 to 22, having a water uptake in the range of from 3 to 8 weight-%, preferably from 4 to 7 weight-%.

24. The molding of any of embodiments 17 to 23, the infrared spectrum of said molding comprising a band in the region of (3700-3750)+/−20 cm$^{-1}$ and a band in the region of (3670-3690)+/−20 cm$^{-1}$, wherein the intensity ratio of the band in the region of (3700-3750)+/−20 cm$^{-1}$ relative to the band in the region of (3670-3690)+/−20 cm$^{-1}$ is at most 1.5, preferably at most 1.4.

25. The molding according to any of embodiments 17 to 24 for use as a catalyst, preferably as catalyst for preparing propylene oxide from propene with hydrogen peroxide as oxidizing agent in acetonitrile as solvent in a continuous process, wherein the selectivity with respect to propylene oxide relative to hydrogen peroxide after a run-time of 500 h is at least 95%, preferably at least 96%.

26. A process comprising
    (i) providing a suspension containing a microporous aluminum-free zeolitic material of structure type MWW containing titanium and zinc (ZnTiMWW);
    (ii) subjecting the suspension provided in (i) to spray-drying to obtain a micropowder;
    (iii) optionally calcining the micropowder obtained in (ii), wherein the micropowder obtained in (ii) or (iii), preferably in (iii), is preferably the micropowder according to any of embodiments 1 to 14.

27. The process of embodiment 26, wherein the suspension provided in (i) has a solid content in the range of from 5 to 25 weight-%, preferably of from 10 to 20 weight-%, the suspension preferably being an aqueous suspension.

28. The process of embodiment 26 or 27, wherein the ZnTiMWW according to (i) contains zinc in an amount of from 1.0 to 2.0 weight-%, preferably of from 1.2 to 1.9 weight-%, calculated as Zn, and titanium in an amount of from 1.0 to 2.0 weight-%, preferably of from 1.2 to 1.8 weight-%, calculated as Ti and based on the weight of the ZnTiMWW.

29. The process of any of embodiments 26 to 28, wherein in (ii), a spray-apparatus, preferably a spray-tower is used for spray-drying the suspension, said apparatus having at least one spray-nozzle, preferably at least one two-component nozzle, said nozzle having a diameter in the range of from 3.5 to 4.5 mm.

30. The process of any of embodiments 26 to 29, wherein in (ii), a spray-apparatus, preferably a spray-tower is used for spray-drying the suspension, said apparatus being operated with a nozzle gas having a temperature in the range of from 20 to 50° C., preferably of from 20 to 30° C., and a drying gas having a temperature in the range of from 250 to 350° C., preferably of from 275 to 325° C., said nozzle gas preferably being an inert gas, more preferably technical nitrogen, and said drying gas preferably being an inert gas, more preferably technical nitrogen.

31. The process of any of embodiments 26 to 30, wherein in (iii), the micropowder is calcined at a temperature in the range of from 600 to 700° C. for a duration in the range of from 0.5 to 6 h.

32. The process of any of embodiments 26 to 31, further comprising
    (iv) shaping the micropowder obtained in (ii) or (iii) to obtain a molding;
    (v) optionally drying and/or calcining the molding obtained in (iv).

33. The process of embodiment 32, wherein the shaping according to (iv) comprises
    (aa) mixing the micropowder with a binder or a binder precursor, preferably a silica binder or a silica binder precursor, wherein the weight ratio of the ZnTiMWW contained in the micropowder relative to silica contained in or resulting from the silica binder is in the range of from 3:7 to 1:4, to obtain a mixture;
    (bb) shaping the mixture obtained in (aa) to obtain the molding, said shaping preferably comprising subjecting the mixture obtained in (aa) to extrusion from which preferably strands are obtained having a diameter preferably in the range of from 1.0 to 2.0 mm, more preferably of from 1.5 to 1.7 mm.

34. The process of embodiment 33, wherein in (aa), a carbohydrate and/or water is/are added as pasting agent.

35. The process of embodiment 33 or 34, wherein the mixing in (aa) is carried out for a duration in the range of from 15 to 60 min, preferably of from 30 to 55 min, more preferably of from 40 to 50 min.

36. The process of any of embodiments 32 to 35, wherein in (iv), no mesopore-forming agent selected from the group consisting of polyalkylene oxides such as polyethylene oxides, polystyrene, polyacrylates, polymethacrylates, polyolefins, polyamides, and polyesters is added.

37. The process of any of embodiments 32 to 36, wherein in (v), the molding is dried at a temperature in the range of from 100 to 150° C. for a duration in the range of from 10 to 20 h and calcined at a temperature in the range of from 500 to 600° C. for a duration in the range of from 0.5 to 2 h.

38. The process of any of embodiments 32 to 37, further comprising
    (vi) subjecting the molding obtained in (iv) or (v), preferably in (v), to a water-treatment;
    (vii) optionally drying and/or calcining the water-treated molding,
    wherein the molding obtained in (vi) or (vii), preferably in (vii), is preferably the molding according to embodiment 17.

39. The process of embodiment 38, wherein in (vi), the water-treatment comprises treating the molding with liquid water in an autoclave under autogenous pressure at a temperature in the range of from 100 to 200° C., preferably of from 125 bis 175° C., more preferably of from 140 to 150° C. for a period of from 2 to 24 hours, preferably of from 6 to 10 h.

40. The process of embodiment 38 or 39, wherein in (vi), the weight ratio of the molding relative to the water is in the range of from 0.02 to 0.08, preferably of from 0.03 to 0.07, more preferably of from 0.04 to 0.06.

41. The process of any of embodiments 38 to 40, wherein in (vii), the water-treated molding is dried at a temperature in the range of from 100 to 150° C. for a duration in the range of from 10 to 20 h and calcined at a temperature in the range of from 400 to 500° C. for a duration in the range of from 1 to 3 h.

42. The process of any of embodiments 32 to 41, wherein the molding is not subjected to steaming.

43. A micropowder, obtainable or obtained by a process according to any of embodiments 26 to 31.

44. A molding, obtainable or obtained by a process according to any of embodiments 32 to 42.

45. Use of the micropowder according to any of embodiments 1 to 14 or according to embodiment 43 or of the molding according to any of embodiment 17 to 24 or according to embodiment 44, as a catalyst, preferably as a catalyst for preparing propylene oxide from propene with hydrogen peroxide as oxidizing agent in acetonitrile as solvent.

The present invention is illustrated by the following examples and reference examples.

EXAMPLES

Reference Example 1

Preparation of a Microporous Aluminum-Free Zeolitic Material of Structure Type MWW Containing Titanium and Zinc (ZnTiMWW)

1.1 Preparation of Boron-Containing MWW 470.4 kg de-ionized water were provided in a vessel. Under stirring at 70 rpm (rounds per minute), 162.5 kg boric acid were suspended in the water. The suspension was stirred for another 3 h. Subsequently, 272.5 kg piperidine were added, and the mixture was stirred for another hour. To the resulting solution, 392.0 kg Ludox® AS-40 were added, and the resulting mixture was stirred at 70 rpm for another hour.

The finally obtained mixture was transferred to a crystallization vessel and heated to 170° C. within 5 h under autogenous pressure and under stirring (50 rpm). The temperature of 170° C. was kept essentially constant for 120 h; during these 120 h, the mixture was stirred at 50 rpm. Subsequently, the mixture was cooled to a temperature of from 50-60° C. within 5 h. The aqueous suspension containing B-MWW had a pH of 11.3 as determined via measurement with a pH electrode.

From said suspension, the B-MWW was separated by filtration. The filter cake was then washed with de-ionized water until the washing water had a conductivity of less than 700 microSiemens/cm From the thus obtained filter cake, an aqueous suspension having a solids content of 15 weight-% was prepared and subjected to spray-drying in a spray-tower with the following spray-drying conditions:
drying gas, nozzle gas: technical nitrogen
temperature drying gas:
   temperature spray tower (in): 288-291° C.
   temperature spray tower (out): 157-167° C.
   temperature filter (in): 150-160° C.
   temperature scrubber (in): 40-48° C.
   temperature scrubber (out): 34-36° C.
pressure difference filter: 8.3-10.3 mbar
nozzle:
   top-component nozzle supplier Gerig; size 0
   nozzle gas temperature: room temperature
   nozzle gas pressure: 2.5 bar
operation mode: nitrogen straight
apparatus used: spray tower with one nozzle
configuration: spray tower-filter-scrubber
gas flow: 1,900 kg/h
filter material: Nomex® needle-felt 20 m$^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 650° C. for 2 h. The calcined material had a boron (B) content of 1.9 wt. %, a silicon (Si) content of 41 wt. %, and a total organic carbon (TOC) content of 0.18 wt. %.

1.2 Preparation of Deboronated MWW a) Deboronation

Based on the spray-dried material obtained according to section 1.1 above, 4 batches of deboronated zeolite MWW were prepared. In each of the first 3 batches, 35 kg of the spray-dried material obtained according to section 1.1 and 525 kg water were employed. In the fourth batch, 32 kg of the spray-dried material obtained according to section 1.1 and 480 kg water were employed. In total, 137 kg of the spray-dried material obtained according to section 1.1 and 2025 kg water were employed.

For each batch, the respective amount of water was passed into a vessel equipped with a reflux condenser. Under stirring at 40 r.p.m., the given amount of the spray-dried material was suspended into the water. Subsequently, the vessel was closed and the reflux condenser put into operation. The stirring rate was increased to 70 r.p.m. Under stirring at 70 r.p.m., the content of the vessel was heated to 100° C. within 10 h and kept at this temperature for 10 h. Then, the content of the vessel was cooled to a temperature of less than 50° C.

The resulting deboronated zeolitic material of structure type MWW was separated from the suspension by filtration under a nitrogen pressure of 2.5 bar and washed four times with deionized water. After the filtration, the filter cake was dried in a nitrogen stream for 6 h.

The deboronated zeolitic material obtained in 4 batches (625.1 kg nitrogen-dried filter cake in total) had a residual moisture content of 79%, as determined using an IR (infrared) scale at 160° C.

b) Spray-Drying of the Nitrogen-Dried Filter Cake

From the nitrogen-dried filter cake having a residual moisture content of 79% obtained according to section a) above, an aqueous suspension was prepared with deionized water, the suspension having a solid content of 15 wt.-%. This suspension was subjected to spray-drying in a spray-tower with the following spray-drying conditions:
drying gas, nozzle gas: technical nitrogen
temperature drying gas:
   temperature spray tower (in): 304° C.
   temperature spray tower (out): 147-150° C.
   temperature filter (in): 133-141° C.
   temperature scrubber (in): 106-114° C.
   temperature scrubber (out): 13-20° C.
pressure difference filter: 1.3-2.3 mbar
nozzle:
   top-component nozzle: supplier Niro, diameter 4 mm
   nozzle gas throughput: 23 kg/h
   nozzle gas pressure: 2.5 bar
operation mode: nitrogen straight
apparatus used: spray tower with one nozzle
configuration: spray tower-filter-scrubber
gas flow: 550 kg/h
filter material: Nomex® needle-felt 10 m$^2$
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged.

The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried MWW material obtained had a B content of 0.08 wt. %, an Si content of 42 wt. %, and a TOC of 0.23 wt. %.

1.3 Preparation of TiMWW

Based on the deboronated MWW material as obtained according to section 1.2, a zeolitic material of structure type MWW containing titanium (Ti) was prepared, referred to in the following as TiMWW. The synthesis was performed in two experiments, described in the following as a) and b):

a) First Experiment

Starting materials:
deionized water: 244.00 kg
piperidine: 118.00 kg
tetrabutylorthotitanate: 10.90 kg
deboronated zeolitic material: 54.16 kg 54.16 kg of the deboronated zeolitic material of structure type MWW were transferred in to a first vessel A.

In a second vessel B, 200.00 kg deionized water were transferred and stirred at 80 r.p.m. 118.00 kg piperidine were added under stirring, and during addition, the temperature of the mixture increased for about 15° C. Subsequently, 10.90 kg tetrabutylorthotitanate and 20.00 kg deionized water were added. Stirring was then continued for 60 min.

The mixture of vessel B was then transferred into vessel A, and stirring in vessel A was started (70 r.p.m.). 24.00 kg deionized water were filled into vessel A and transferred to vessel B.

The mixture in vessel B was then stirred for 60 min. at 70 r.p.m. At the beginning of the stirring, the pH of the mixture in vessel B was 12.6, as determined with a pH electrode.

After said stirring at 70 r.p.m., the frequency was decreased to 50 r.p.m., and the mixture in vessel B was heated to a temperature of 170° C. within 5 h. At a constant stirring rate of 50 r.p.m., the temperature of the mixture in vessel B was kept at an essentially constant temperature of 170° C. for 120 h under autogenous pressure. During this crystallization of TiMWW, a pressure increase of up to 10.6 bar was observed. Subsequently, the obtained suspension containing TiMWW having a pH of 12.6 was cooled within 5 h.

The cooled suspension was subjected to filtration, and the separated mother liquor was transferred to waste water discharge. The filter cake was washed four times with deionized water under a nitrogen pressure of 2.5 bar. After the last washing step, the filter cake was dried in a nitrogen stream for 6 h.

From 246 kg of said filter cake, an aqueous suspension was prepared with deionized water, the suspension having a solid content of 15 wt.-%. This suspension was subjected to spray-drying in a spray-tower with the following spray-drying conditions:

drying gas, nozzle gas: technical nitrogen
temperature drying gas:
  temperature spray tower (in): 304° C.
  temperature spray tower (out): 147-152° C.
  temperature filter (in): 133-144° C.
  temperature scrubber (in): 111-123° C.
  temperature scrubber (out): 12-18° C.
pressure difference filter: 1.8-2.8 mbar nozzle:
  top-component nozzle: supplier Niro, diameter 4 mm
  nozzle gas throughput: 23 kg/h
  nozzle gas pressure: 2.5 bar
operation mode: nitrogen straight
apparatus used: spray tower with one nozzle
configuration: spray tower-filter-scrubber
gas flow: 550 kg/h
filter material: Nomex® needle-felt 10 m$^2$
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried TiMWW material obtained from the first experiment had a Si content of 37 wt. %, a Ti content of 2.4 wt.-%, and a TOC of 7.5 wt. %.

b) Second Experiment

The second experiment was carried out in the same way as the first experiment described in section a) above. The spray-dried TiMWW material obtained from the second experiment had a Si content of 36 wt. %, a Ti content of 2.4 wt.-%, a TOC of 8.0 wt. %

1.4 Acid Treatment of TiMWW

Each of the two spray-dried TiMWW materials as obtained in the first and the second experiment described in sections 1.3 a) and 1.3 b) above was subjected to acid treatment as described in the following in sections a) and b). In section c) hereinunder, it is described how a mixture of the materials obtained from a) and b) are spray-dried. In section d) hereinunder, it is described how the spray-dried material is calcined.

a) Acid Treatment of the Spray-Dried Material Obtained According to Section 1.3 a)

Starting materials:
  deionized water: 690.0 kg
  nitric acid: (53%): 900.0 kg
  spray-dried Ti-MWW 1.3. a): 53.0 kg 670.0 kg deionized water were filled in a vessel. 900 kg nitric acid were added, and 53.0 kg of the spray-dried TiMWW were added under stirring at 50 r.p.m. The resulting mixture was stirred for another 15 min. Subsequently, the stirring rate was increased to 70 r.p.m.

Within 1 h, the mixture in the vessel was heated to 100° C. and kept at this temperature and under autogenous pressure for 20 h under stirring. The thus obtained mixture was then cooled within 2 h to a temperature of less than 50° C.

The cooled mixture was subjected to filtration, and the filter cake was washed six times with deionized water under a nitrogen pressure of 2.5 bar. After the last washing step, the filter cake was dried in a nitrogen stream for 10 h. The washing water after the sixth washing step had a pH of about 2.7. 225.8 kg dried filter cake were obtained.

b) Acid Treatment of the Spray-Dried Material Obtained According to Section 1.3 b)

Starting materials:
  deionized water: 690.0 kg
  nitric acid: (53%): 900.0 kg
  spray-dried Ti-MWW 1.3. b): 55.0 kg The acid treatment of the spray-dried material obtained according to section 1.3 b) was carried in the same way as the acid treatment of the spray-dried material obtained according to section 1.3 a) as described in section 1.4 a). The washing water after the sixth washing step had a pH of about 2.7. 206.3 kg dried filter cake were obtained.

c) Spray-Drying of the Mixture of the Materials Obtained from 1.4 a) and 1.4 b)

From 462.1 kg of the mixture of the filter cakes obtained from 1.4 a) and 1.4 b), an aqueous suspension was prepared with deionized water, the suspension having a solid content of 15 wt.-%. This suspension was subjected to spray-drying in a spray-tower with the following spray-drying conditions:

drying gas, nozzle gas: technical nitrogen
temperature drying gas:
   temperature spray tower (in): 304-305° C.
   temperature spray tower (out): 151° C.
   temperature filter (in): 141-143° C.
   temperature scrubber (in): 109-118° C.
   temperature scrubber (out): 14-15° C.
pressure difference filter: 1.7-3.8 mbar
nozzle:
   top-component nozzle: supplier Niro, diameter 4 mm
   nozzle gas throughput: 23 kg/h
   nozzle gas pressure: 2.5 bar
operation mode: nitrogen straight
apparatus used: spray tower with one nozzle
configuration: spray tower-filter-scrubber
gas flow: 550 kg/h
filter material: Nomex® needle-felt 10 m$^2$
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried acid-treated TiMWW material had a Si content of 42 wt. %, a Ti content of 1.6 wt.-%, and a TOC of 1.7 wt. %.

d) Calcination of the Spray-Dried Material Obtained According to 1.4. C)

The spray-dried material was then subjected to calcination at 650° C. in a rotary furnace for 2 h. The calcined material had a Si content of 42.5 wt. %, a Ti content of 1.6 wt.-% and a TOC content of 0.15 wt. %. The Langmuir surface are determined via nitrogen adsorption at 77 K according to DIN 66134 was 612 m$^2$/g, the multipoint BET specific surface area determined via nitrogen adsorption at 77 K according t DIN 66134 was 442 m$^2$/g. The total intrusion volume determined according to Hg porosimetry according to DIN 66133 was 4.9 ml/g (milliliter/gram), the respective total pore area 104.6 m$^2$/g. The degree of crystallization determined via XRD was 80%, the average crystallite size 31 nm. The XRD of the material is shown in FIG. 1.

1.5 Impregnation of TiMWW with Zn

The acid-treated, spray-dried and calcined material as obtained according to 1.4 d) was then subjected to an impregnation stage.

Starting materials:
   deionized water: 2610.0 kg
   zinc acetate dihydrate: 15.93 kg
   calcined Ti-MWW 1.4 d): 87.0 kg Impregnation was carried out in 3 batches a) to c) as follows:

a) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 1.4 d) were suspended. Subsequently, the vessel was closed and the reflux condenser put into operation. The stirring rate was increased to 70 r.p.m.

b) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 1.4 d) were suspended. Subsequently, the vessel was closed and the reflux condenser put into operation. The stirring rate was increased to 70 r.p.m.

c) In a vessel equipped with a reflux condenser, a solution of 930 kg deionized water and 5.67 kg zinc acetate dihydrate was prepared within 30 min. Under stirring (40 r.p.m.), 31 kg of the calcined Ti-MWW material obtained according to 1.4 d) were suspended. Subsequently, the vessel was closed and the reflux condenser put into operation. The stirring rate was increased to 70 r.p.m.

In all batches a) to c), the mixture in the vessel was heated to 100° C. within 1 h and kept under reflux for 4 h at a stirring rate of 70 r.p.m. Then, the mixture was cooled within 2 h to a temperature of less than 50° C. For each batch a) to c), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h.

For batch a), 106.5 kg nitrogen-dried filter cake were finally obtained. For batch b), 107.0 kg nitrogen-dried filter cake were finally obtained. For batch c), 133.6 kg nitrogen-dried filter cake were finally obtained.

The thus dried Zn-impregnated TiMWW material (Zn-TiMWW), for each batch, had a Si content of 42 wt. %, a Ti content of 1.6 wt.-%, a Zn content of 1.4 wt. % and a TOC of 1.4 wt. %.

Reference Example 2

Determination of the Crush Strength of the Moldings of the Present Invention

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH &

Co. Technische Dokumentation, August-Nagel-Strasse 11, D-89079 Ulm, Germany. The title page of the instructions handbook is shown in FIG. 9.

With said machine, a given strand as described in Examples 2 and 3, having a diameter of 1.7 mm, is subjected to an increasing force via a plunger having a diameter of 3 mm until the strand is crushed. The force at which the strand crushes is referred to as the crushing strength of the strand.

The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 3

Determination of the Silanol Concentration of the Moldings of the Present Invention For the determination of the silanol concentration, the $^{29}$Si MAS NMR experiments were carried out at room temperature on a VARIAN Infinityplus-400 spectrometer using 5.0 mm $ZrO_2$ rotors. The $^{29}$Si MAS NMR spectra were collected at 79.5 MHz using a 1.9 µs π/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS).

For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 4

$^{29}$Si Solid-State NMR Spectra Regarding $Q^3$ and $Q^4$ Structures

The effect of the inventive water treatment on the molding related to $Q^3$ and $Q^4$ structures in the material was characterized by comparing the changes in $^{29}$Si solid-state NMR spectra under comparable conditions.

All $^{29}$Si solid-state NMR experiments were performed using a Bruker Advance spectrometer with 300 MHz $^1$H Larmor frequency (Bruker Biospin, Germany). Samples were packed in 7 mm $ZrO_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm.

The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm (see FIG. 10 for the molding of Example 2).

Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit.

After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively.

For the quantification of spectrum changes, a ratio was calculated that reflects changes in the peak areas "left hand" and "right hand", as follows. The six peaks as described in FIG. 10 were labeled with 1, 2, 3, 4, 5, and 6, and the ratio Q was calculated with the formula $100 * \{[a_1 + a_2]/[a_4 + a_5 + a_6]\}/a_3$. In this formula, $a_{i,\ i=1\ \ldots\ 6}$ represents the area of the fitted peak to which this number was attributed.

Reference Example 5

FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken.

Reference Example 6

Water Adsorption/Desorption

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 wt. %). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 wt. % from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 wt. % to 5 wt. % with a step of 10% and the change in the weight of the sample (water uptake) was monitored and recorded.

Reference Example 7

PO Test

In the PO test, the moldings of the present invention are tested as catalysts in a mini autoclave by reaction of propene with an aqueous hydrogen peroxide solution (30 wt. %) to yield propylene oxide. In particular, 0.63 g of the moldings of the invention were introduced together with 79.2 g of acetonitrile and 12.4 g of propene at room temperature, and 22.1 g of hydrogen peroxide (30 wt. % in water) were introduced in a steel autoclave. After a reaction time of 4 hours at 40° C., the mixture was cooled and depressurized, and the liquid phase was analyzed by gas chromatography with respect to its propylene oxide content.

The propylene oxide content of the liquid phase (in wt. %) is the result of the PO test.

Reference Example 8

Determination of Dv10, Dv50, and Dv90 Values

1. Sample Preparation
    1.0 g of the micropowder is suspended in 100 g deionized water and stirred for 1 min.
2. Apparatus and Respective Parameters Used
    Mastersizer S long bed version 2.15, ser. No. 33544-325; supplier: Malvern Instruments GmbH, Herrenberg, Germany
    focal width: 300RF mm
    beam length: 10.00 mm
    module: MS17
    shadowing: 16.9%
    dispersion model: 3$$D
    analysis model: polydisperse
    correction: none Reference Example 9

Determination of the Filtration Resistance of a Suspension and of the Washing Resistance of a Filter Cake The filtration resistance R(F) of a given suspension was determined according to the formula:

$$R(F) = [2*t(end)*A*\text{delta } p]/[V(F,end)*H(end)]$$

wherein
t(end)=endpoint of filtration (in s) (time after start of filtration when the fluid level in the filtration device has the same height as the filter cake)
A=filter area (in $m^2$)
delta p=filtration pressure (in Pa) (pressure difference over the filter cake)
V(F,end)=volume of the filtrate at t(end) (in $m^3$)
H(end)=filter cake height at t(end) (in m)

The washing resistance R(W) of a given filter cake was determined according to the formula:

$$R(W) = [t(end)*A*\text{delta } p]/[V(F,end)*H(end)]$$

wherein
t(end)=endpoint of washing (in s) (time after start of washing when the fluid level of the washing agent in the filtration device has the same height as the filter cake)
A=filter area (in $m^2$)
delta p=filtration pressure (in Pa) (pressure difference over the filter cake)
V(F,end)=volume of the filtrate at t(end) (in $m^3$)
H(end)=filter cake height at t(end) (in m)

Reference Example 10

Determination of Crystallinity Via XRD

The particle size and the crystallinity of the zeolitic materials according to the present invention were determined by XRD analysis. The data were collected using a standard Bragg-Brentano diffractometer with a Cu—X-ray source and an energy dispersive point detector. The angular range of 2° to 70° (2 theta) was scanned with a step size of 0.02°, while the variable divergence slit was set to a constant illuminated sample length of 20 mm. The data were then analyzed using TOPAS V4 software, wherein the sharp diffraction peaks were modeled using a Pawley fit containing a unit cell with the following starting parameters: a=14.4 Angstrom and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Example 1

Preparation of a Micropowder

From 347.1 kg of the mixture of the filter cakes obtained from Reference Example 1.5, an aqueous suspension was prepared with deionized water, the suspension having a solid content of 15 wt.-%. This suspension was subjected to spray-drying in a spray-tower with the following spray-drying conditions:
    apparatus used: spray tower with one nozzle
    operation mode: nitrogen straight
    configuration: dehumidifier-filter-scrubber
    dosage:
        flexible-tube pump VF 10 (supplier: Verder)
        nozzle with a diameter of 4 mm (supplier: Niro)
        filter material: Nomex® needle-felt 10 $m^2$

|  |  | Runtime/h | | | | |
| --- | --- | --- | --- | --- | --- | --- |
|  |  | 0.5 | 1.5 | 2.5 | 3.5 | 4.5 |
| Flow rate gas/(kg/h) |  | 550 | 550 | 550 | 550 | 550 |
| Temperature | spray tower (in) | 305 | 305 | 305 | 305 | 305 |
| drying gas/° C. | spray tower (out) | 151 | 151 | 151 | 151 | 151 |
|  | Filter (in) | 140 | 137 | 130 | 127 | 126 |
|  | Scrubber (in) | 110 | 110 | 110 | 108 | 105 |
|  | Scrubber (out) | 14 | 14 | 15 | 15 | 15 |
| Differential | spray tower | 3.1 | 3 | 3 | 2.8 | 2.9 |
| pressure/ | Filter | 1.7 | 1.7 | 1.8 | 1.8 | 2.1 |
| mbar | Scrubber | 3.8 | 4.1 | 4.2 | 4.2 | 4.2 |
| Pressure/ mbar | spray tower | −103 | −1.2 | −0.9 | −0.9 | −1.1 |
| Nozzle gas | Flow rate kg/h | 23 | 23 | 23 | 23 | 23 |
|  | Temperature/° C. | r.t.*) | r.t.*) | r.t.*) | r.t.*) | r.t.*) |
|  | Pressure/bar | 2.5 | 2.5 | 2.5 | 2.5 | 2.5 |
| Spray-dried product | Temperature/° C. | r.t.*) | r.t.*) | r.t.*) | r.t.*) | r.t.*) |

*)room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material thus obtained had a Zn content of 1.4 wt. %, a Ti content of 1.7 wt. %, a Si content of 40 wt. %, and a TOO content of 0.27 wt. %

The spray-dried product was then subjected to calcination for 2 h at 650° C. under air in a rotary furnace, yielding 76.3 kg of calcined spray-dried ZnTiMWW.

Characterization of the Calcined Spray-Dried Micropowder:

The calcined spray-dried material thus obtained had a Zn content of 1.4 wt. %, a Ti content of 1.7 wt. %, a Si content of 42 wt. %, and a C content of 0.14 wt. %.

The bulk density of the calcined spray-dried ZnTiMWW was 90 g/l (gram/liter).

The mesopores of the micropowder had an average pore diameter (4V/A) of 27.2 nm as determined by Hg porosimetry according to DIN 66133.

The macropores of the micropowder had an average pore diameter (4V/A) of 95.6 nm as determined by Hg porosimetry according to DIN 66133.

The micropores of the ZnTiMWW contained in the micropowder had an average pore diameter of 1.13 nm as determined by nitrogen adsorption according to DIN 66134 (Horward-Kawazoe method).

The Dv10 value of the particles of the micropowder as determined according to Reference Example 8 was 5.18 micrometers. The Dv50 value of the particles of the micropowder as determined according to Reference Example 8 was 24.8 micrometers. The Dv90 value of the particles of the micropowder as determined according to Reference Example 8 was 93.53 micrometers. The respective result is further illustrated in FIG. 12.

The degree of crystallization determined via XRD was 86%+/−10%, the average crystallite size 38.5 nm+/−10%. The XRD of the material is shown in FIG. 2. It was found that the crystalline phase exhibits a pure MWW structure. No other crystalline titania phases such as anatase, rutile or brookite, or crystalline zinc silicate ($Zn_2SiO_4$) such as willemite could be detected.

SEM pictures of a representative sample of the calcined spray-dried material are shown in FIG. 5-8. FIGS. 5 and 6 in particular give an overview of the particle sizes and the respective size distribution of the micropowder of the present invention. FIG. 7 nicely illustrates the fact that the particles of the inventive micropowder are highly porous whereas FIG. 8 clearly shows the platelet substructure of a typical micropowder particle according to the present invention, wherein the platelets are typical for a zeolitic material having MWW structure.

Other Characteristics:

The Langmuir surface are determined via nitrogen adsorption at 77 K according to DIN 66134 was 586 $m^2/g$, the multipoint BET specific surface area determined via nitrogen adsorption at 77 K according t DIN 66134 was 423 $m^2/g$. The total intrusion volume determined according to Hg porosimetry according to DIN 66133 was 4.3 ml/g (milliliter/gram), the respective total pore area 80.7 $m^2/g$.

Example 2

Preparation of a Molding

Starting from the calcined spray-dried ZnTiMWW material obtained in Example 1, a molding was prepared, dried, and calcined. Therefor, 22 batches were prepared, each starting from 3.4 kg of the calcined spray-dried ZnTiMWW material obtained in Example 1, 0.220 kg Walocel™ (Walocel MW 15000 GB, Wolff Cellulosics GmbH & Co. KG, Germany), 2.125 kg Ludox® AS-40 and 6.6 l deionized water, as follows:

3.4 kg ZnTiMWW and 0.220 kg Walocel were subjected to kneading in an edge mill for 5 min. Then, during further kneading, 2.125 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head outlet, the strands were not subjected to a cutting to length.

The strands thus obtained were dried for 16 h at 120° C. in a drying chamber under air.

In total (sum of the 22 batches), 97.1 kg white strands with a diameter of 1.7 mm were obtained.

65.5 kg of the dried strands were subjected to calcination in a rotary furnace at 550° C. for 1 h under air, yielding 62.2 kg calcined strands. Thereafter, the strands were sieved (mesh size 1.5 mm), and the yield, after sieving, was 57.7 kg.

Characterization of the Strands Obtained According to Example 2:

The thus obtained moldings exhibited a bulk density of 322 g/l (gram per liter) and had a Zn content of 1.2 wt. %, a Ti content of 1.4 wt. %, a Si content of 43 wt. %, and a C content of 0.13 wt. %. The sodium (Na) content was 0.07 wt. %.

The mesopores of the micropowder had an average pore diameter (4V/A) of 20.1 nm as determined by Hg porosimetry according to DIN 66133.

The macropores of the micropowder had an average pore diameter (4V/A) of 46.8 nm as determined by Hg porosimetry according to DIN 66133.

The degree of crystallization determined via XRD was 74+/−%, the average crystallite size 38.0 nm+/−10%. The XRD of the material is shown in FIG. 3.

The crush strength of the moldings as determined according to the method using a crush strength test machine Z2.5/TS1S as described in Reference Example 2 was 5.3 N (standard deviation: 1.31N). The minimum value found when testing the 10 samples was 4.13 N, the maximum value 8.13 N.

The concentration of silanol groups with respect to the total number of Si atoms of the moldings, as determined according to $^{29}$Si MAS NMR, was 5.2 wt. %. As to the specific determination of the silanol concentration, reference is made to Reference Example 3. The $^{29}$Si MAS NMR is shown in FIG. 10. After the curve had been deconvolved by the proper Gaussian-Lorentzian line shapes, six peaks were clearly observed.

The parameter Q as determined according to Reference Example 4 was found to be 1.65.

The total amount of adsorbed water as determined according to Reference Example 6 of the molding was 7.5 weight-%. In FIG. 13, the isotherms are shown.

Other Characteristics:

The Langmuir surface are determined via nitrogen adsorption at 77 K according to DIN 66133 was 499 m$^2$/g, the multipoint BET specific surface area determined via nitrogen adsorption at 77 K according t DIN 66133 was 361 m$^2$/g. The total intrusion volume (please explain) determined according to Hg porosimetry according to DIN 66133 was 1.2 ml/g (milliliter/gram), the respective total pore area 92.2 m$^2$/g.

It was found that the crystalline phase of the moldings exhibits an essentially pure MWW structure. In particular, no other crystalline titania phases such as anatase, rutile or brookite, or crystalline zinc silicate ($Zn_2SiO_4$) such as willemite could be detected via XRD.

Example 3

Post-Treatment of the Molding

Starting from the calcined strands obtained according to Example 2, a post-treatment stage was performed as follows:

590 kg deionized water were filled in a vessel. Then, 29.5 kg of the calcined moldings obtained according to Example 2 were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h.

The water-treated strands were subjected to filtration and washed with deionized water.

The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 27.5 kg.

Characterization of the Strands Obtained According to Example 3:

The thus obtained water-treated moldings exhibited a bulk density of 340 g/l (gram per liter) and had a Zn content of 1.3 wt. %, a Ti content of 1.4 wt. %, a Si content of 43 wt. %, and a C content of 0.10 wt. %.

The mesopores of the micropowder had an average pore diameter (4V/A) of 20.2 nm as determined by Hg porosimetry according to DIN 66133. Thus, the inventive water treatment has practically no influence on the mesopore characteristics of the molding (cf. the molding according to Example 2, having a respective average pore diameter of 20.1 nm).

The macropores of the micropowder had an average pore diameter (4V/A) of 45.9 nm as determined by Hg porosimetry according to DIN 66133. Thus, the inventive water treatment has practically no influence on the macropore characteristics of the molding (cf. the molding according to Example 2, having a respective average pore diameter of 46.8 nm).

The degree of crystallization determined via XRD was 64%+/−10%, the average crystallite size 39.4 nm+/−10%. The XRD of the material is shown in FIG. 4. Thus, while not having a significant influence on the average crystallite size (cf. Example 2: 38.0 nm+/−10%), the inventive water treatment had a considerable influence on the degree of crystallization which is decreased from a value of 74% (cf. Example 2) to a value of 64%.

The crush strength of the moldings as determined according to the method using a crush strength test machine Z2.5/TS1S as described in Reference Example 2 was 12.71 N (standard deviation: 2.06). The minimum value found when testing the 10 samples was 9.87 N, the maximum value 15.59 N. These values clearly show that the inventive water treatment of the ZnTiMWW micropowder containing molding leads to a significant increase in the mechanical resistance of the molding (cf. the non-water treated moldings according to Example 2 having a crush strength of only 5.3 N). Due to the fact that in industrial-scale processes where such moldings are preferably employed as catalysts in continuous processes, and due to the fact that the preferred use of the moldings in these processes is in the form of fixed-bed catalysts which are exposed to a continuous mechanical stress, the inventive water treatment allows for significantly improving the mechanical suitability of the moldings.

The concentration of silanol groups with respect to the total number of Si atoms of the moldings, as determined according to $^{29}$Si MAS NMR, was 2.5 wt. %. As to the specific determination of the silanol concentration, reference is made to Reference Example 3. The $^{29}$Si MAS NMR is shown in FIG. 11. After the curve had been deconvolved by the proper Gaussian-Lorentzian line shapes, six peaks were clearly observed.

The parameter Q as determined according to Reference Example 4 was found to be 1.03. Clearly, the Q was considerably decreased by the inventive water treatment from 1.65 to 1.03.

The total amount of adsorbed water as determined according to Reference Example 6 of the molding was 6.2 weight-%. Therefore, it is clearly shown that the inventive water treatment increases the hydrophobicity of the molding. In FIG. 13, the isotherms are shown.

The intensity ratio of the infrared band in the region of 3746+/−20 cm$^{-1}$ attributed to the first type of silanol groups, relative to the infrared band in the region of 3678+/−20 cm$^{-1}$ attributed to second type of silanol groups was smaller than 1.2. Compared to the respective intensity ratio of the non-water-treated molding according to Example 2, the intensity ratio was decreased. The IR spectrum of the molding according to Example 2 is shown in FIG. 14, the IR spectrum of the molding according to Example 3 is shown in FIG. 15.

Other Characteristics

The Langmuir surface are determined via nitrogen adsorption at 77 K according to DIN 66133 was 418.1 m$^2$/g, the multipoint BET specific surface area determined via nitrogen adsorption at 77 K according t DIN 66133 was 299.8 m$^2$/g. The total intrusion volume determined according to Hg porosimetry according to DIN 66133 was 1.1322 ml/g (milliliter/gram), the respective total pore area 92.703 m$^2$/g.

It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Example 4

Test of the Moldings as Catalyst for the Epoxidation of Propene 4.1 Catalytic Test of the Micropowder According to the Present Invention The micropowder as obtained from Example 1 was subjected to the PO test as described in Reference Example 7 The following value was obtained:

PO test: 12.4 wt. % PO

Clearly, the PO test shows that the micropowder according to present may serve as a good catalyst for the preparation of propylene oxide from propene in acetonitrile as solvent, using hydrogen peroxide as oxidizing agent.

4.2 Continuous Epoxidation Reaction with the Molding of Example 2 a) Experimental Setup

The continuous epoxidation reaction was carried out in a vertically arranged steel tube reactor having a length of 1,200 mm and an inner diameter of 7 mm. The tube was equipped with a cooling jacket through which a thermostatized heat-transfer medium (either water or water/glycol mixture) was circulated in order to control the temperature. The flow rate of the heat-transfer medium was chosen in such a way that the difference between inlet and outlet temperature was less than 1° C. and the medium was circulated in co-current flow with respect to the reaction medium. The inlet temperature of the heat-transfer medium was used as the control temperature for the thermostat. The reactor was charged with glass beads to a height of 10 mm, then with 15 g of the moldings as obtained according to Example 2 (non-water-treated molding) and any room at the top of the reactor was filled with glass beads, thus obtaining a fixed-bed reactor. As starting materials, acetonitrile (puriss.), hydrogen peroxide (aqueous solution, concentration of hydrogen peroxide 40 weight-%, commercial product from Solvay), and propene (polymer grade, 99.3 weight-% propene, 0.7 weight-% propane) were continuously fed to a mixing point using three separate metering pumps with the following flow rates:

hydrogen peroxide: 16.7 g/h
acetonitrile: 68 g/h
propene: 10.8 g/h

The mixed stream was fed to the bottom of the reactor. At the top of the reactor the pressure was controlled by a pressure control valve set to 20 bars. The pressure was chosen so that no gas was present in the product mixture. In order to provide comparable results, the experiment was carried out at an essentially constant hydrogen peroxide conversion of (90+/−3)% which was achieved by adjusting the temperature of the cooling water depending on the hydrogen peroxide conversion which in turn was calculated by colorimetrically measuring the amount of hydrogen peroxide contained in the reactor output (titanyl-sulfate method) relative to the amount of hydrogen peroxide introduced into the reactor. The temperature, T, which is referred to in the following and which is shown in the respective figures as discussed herein under is to be understood as the temperature of the heat-transfer medium at the cooling jacket inlet.

In order to analyze the reactor discharge, the discharge was expanded, and the gaseous phase was separated from the liquid phase. The amount of both the gaseous phase and the liquid phase was metered and both were analyzed using calibrated gas chromatography with respect to their respective contents of propylene oxide, propene, hydroperoxypropanols (ROOH, mixture of two 1-hydroperoxy-2-propanol and 2-hydroperoxy-1-propanol), oxygen, and propylene glycol (named 'diol' for short in the figures). The ROOH content was determined by reducing the ROOH with triphenyl phosphine (TPP) and determining the content of propylene glycol prior to and after the reduction. The hydrogen peroxide content was determined using the colorimetric titanyl sulfate method.

b) Results

The results discussed below are shown in FIGS. 16 and 17.

After a time on stream of about 100 h, the reaction system was essentially stable, and the conversion of hydrogen peroxide was in the range of about (90+/−2)%. In order to maintain the conversion in this range, the temperature of the heat-transfer medium, which was about 48° C. after 100 hours, was increased to about 57° C. after 330 hours, i.e. in a comparatively narrow temperature window of about 9° C. From a time on stream of 100 h to a time on stream of 330 hours, the selectivity of propylene oxide relative to propene exhibited excellent and essentially constant values of about 98%. The selectivity of propylene oxide relative to hydrogen peroxide also exhibited very good values of about 95%. The use of the molding of Example 2 further allowed for oxygen selectivities in the range of from about 1 to 2%, ROOH selectivities of about 3 to 3.6%, and diol selectivities of at most about 0.6%. The oxygen, ROOH, and diol selectivities are to be understood as selectivities relative to hydrogen peroxide, based on the following stoichiometries:

propene+$H_2O_2$→propylene glycol (diol)

propene+$2H_2O_2$→hydroperoxypropanols (ROOH)+$H_2O$ $2H_2O_2$→$O_2$+$2H_2O$

Summarized, the continuous epoxidation reaction, i.e. the epoxidation reaction carried out in a mode which is especially suitable in industrial-scale processes and, thus, interesting for commercial purposes, convincingly showed that the molding of the present invention as obtained from Example 2 is an ideal catalyst, allowing, at a constantly high hydrogen peroxide conversion of about (90+/−2)%, for excellent selectivities with regard to propylene oxide, in particular with regard to propylene oxide based on propene. Therefore, the molding according to Example 2 allows for an excellent utilization of the starting materials hydrogen peroxide and propene, with the utilization of propene being even better than the utilization of hydrogen peroxide.

4.3 Continuous Epoxidation Reaction with the Water-Treated Molding of Example 3 a) Experimental Setup

The experimental setup used for the continuous epoxidation reaction with the water-treated molding of Example 3 was identical to the setup as described in 4.2 a) hereinabove.

b) Results for a Time on Stream Between 100 and 330 h—Comparison with 4.2

The results discussed below are shown in FIGS. 18 and 19.

After a run-time of about 100 h, the reaction system was stable, and the conversion of hydrogen peroxide was in the range of about (92+/−2)% and, thus, at values slightly higher than the values in 4.2 above.

In order to maintain this conversion, the temperature of the heat-transfer medium which was about 45° C. after 100 hours did not have to be increased at all until the 330 hours time on stream were reached. Therefore, compared to the moldings according to Example 2, the water-treated molding, after the same time of 330 hours, necessitated no temperature increase in order to maintain a hydrogen peroxide conversion which was even slightly higher than the conversion achieved when using the non-water-treated molding. Therefore, the rate of deactivation of the catalyst, deltaT/deltat (in ° C./h), is essentially 0° C./h whereas in Example 4.2, the respective deactivation rate is 9° C./230 h=0.039° C./h. Without any doubt, the water-treated catalyst represents a highly advantageous embodiment of the present invention.

Additionally, during the first 330 hours, both the selectivity of propylene oxide with regard to propene and the selectivity of propylene oxide with regard to hydrogen peroxide are higher than the respective values achieved with the non-water-treated moldings, although, as mentioned, the conversion and thus the activity of the water-treated molding is higher. In particular, the selectivity of propylene oxide with regard to propene is at an essentially constant value of about 99% (non-water-treated molding: about 98%), and the selectivity of propylene oxide with regard to hydrogen peroxide is at an essentially constant value of about 98% (non-water-treated molding: about 95%).

Still further, the use of the molding of Example 3 and thus the specific inventive water treatment also allowed for significantly improving, i.e. decreasing the selectivities with regard to the by-products ROOH, diol, and oxygen. Specifically, it was found that the oxygen selectivities were in the range of from about 0.5 to less than 1% (non-water-treated molding: about 1-2%), ROOH selectivities of about 0.5 to 1% (non-water-treated molding: about 3 to 3.5%), and diol selectivity of well below 0.5% (non-water-treated molding: at most about 0.5%). All selectivities are to be understood as selectivities relative to hydrogen peroxide.

In the following table, the results for times on stream up to 330 h are summarized. This table directly shows the significant improvement achieved according to the specific inventive water treatment if applied to a molding according to the invention:

TABLE

Comparison of the moldings according to Examples 2 and 3 Run-time up to 330 h

| catalytic property | molding example 2 | molding example 3 | improvement |
|---|---|---|---|
| hydrogen peroxide conversion | 90 +/− 2% | 92 +/− 2% | yes |
| propylene oxide selectivity based on propene | 98% | 99% | yes |
| propylene oxide selectivity based on hydrogen peroxide | 95% | 98% | yes |
| oxygen selectivity based on hydrogen peroxide | 0.5-1% | 1-2% | yes |
| peroxides selectivity based on hydrogen peroxide | 0.5-1% | 3-3.5% | yes |
| diol selectivity based on hydrogen peroxide | <<0.5% | <0.5% | yes | c) Run-Times of More than 330 h

Most surprisingly, it was further found that these extremely advantageous characteristics of the water-treated moldings according to the present invention are essentially maintained at longer run-times, in particular at runtimes of up to 720 h.

First, in order to maintain the conversion of (92+/−2)%, the temperature of the cooling medium had to be increased for only about 2° C. which is a very narrow temperature window in terms of an epoxidation catalyst used in a liquid phase epoxidation of propene. In particular, it is noted that after 720 h, the deactivation rate deltaT/deltat=2° C./720 h=0.003° C./h and, thus, more than an order of magnitude lower than the deactivation rate of the non-water-treated catalyst after only 230 h (0.039° C./h.

Second, the selectivity of propylene oxide with regard to propene remained essentially constant within 720 h, and the selectivity of propylene oxide with regard to hydrogen peroxide only slightly decreased within the 390 h following the first 330 hours on stream.

Third, oxygen selectivities increased to values which were still below 1.5% after 720 h (the non-water-treated molding exhibited oxygen conversion of about 2 already after 330 h) whereas the ROOH selectivities even slightly decreased, and the diol selectivities only slightly increased and, after 720 h, were still below 0.5%.

In other words: in addition to the extremely advantageous characteristics within the first 330 h which show that the water-treated moldings are significantly better catalysts than the non-water-treated moldings, the water-treated moldings additionally show a long-time stability with essentially no deactivation of the catalyst for run-times of more than 330 h.

4.4 Summary

Compared to the non-water-treated molding according to Example 2 which already exhibited very good catalytic properties, the water-treated molding according to Example 3, i.e. the molding of Example 2 having been subjected to the specific inventive water-treatment, was found to be an almost perfect catalyst, in particular for the preparation of propylene oxide from propene in acetonitrile as solvent using hydrogen peroxide as oxidizing agent. Thus, it was found that the specific inventive water treatment allows for significantly improving the catalytic properties of an already good catalyst. In particular, it was found that the properties of the water-treated molding such as the specific crush strength, the $Q^3$ and $Q^4$ structures, the hydrophobicity characterized by the water absorption/desorption, as well the silanol concentration and the intensity ratio of the FT-IR peaks as discussed above, which parameters are all influenced by the specific inventive water treatment, indeed define the extraordinary catalytic properties of the inventive water-treated molding.

Example 5

Preparation of a Molding Containing ZnTiMWW Spray Powder

Example 5.1

Preparation of a BMWW Spray Powder a) Hydrothermal Synthesis
  480 kg de-ionized water were provided in a vessel. Under stirring at 70 rpm (rounds per minute), 166 kg boric acid were suspended in the water. The suspension was stirred for another 3 h. Subsequently, 278 kg piperidine were added, and the mixture was stirred for another hour. To the resulting solution, 400 kg Ludox® AS-40 were added, and the resulting mixture was stirred at 70 rpm for another hour.
  In this synthesis mixture, the boron source boric acid, calculated as elemental boron, relative to the silicon source Ludox® AS-40, calculated as elemental silicon, was present in a molar ratio of 1:1; the water relative to the silicon source Ludox® AS-40, calculated as elemental silicon, was present in a molar ratio of 10:1; and the template compound piperidine relative to the silicon source Ludox® AS-40, calculated as elemental silicon, was present in a molar ratio of 1.2:1.
  The finally obtained mixture was transferred to a crystallization vessel and heated to 175° C. within 5 h under autogenous pressure and under stirring (50 rpm). The temperature of 175° C. was kept essentially constant for 60 h; during these 60 h, the mixture was stirred at 50 rpm. Subsequently, the mixture was cooled to a temperature of from 50-60° C. within 5 h.
  The mother liquor containing the crystallized BMWW precursor had a pH of 11.3 as determined via measurement with a pH electrode.
b) pH Adjustment
  To the mother liquor obtained in a), 1400 kg of a 10 weight-% $HNO_3$ aqueous solution were added under stirring at 50 r.p.m. (rounds per minute). The adding was carried out at a temperature of the suspension of 40° C.
  After the addition of the 10 weight-% $HNO_3$ aqueous solution, the resulting suspension was further stirred for 5 h under stirring at 50 r.p.m. at a temperature of the suspension of 40° C.
  The pH of the thus pH-adjusted mother liquor as determined via measurement with a pH electrode was 7.
  The Dv10 value of the particles contained in the pH-adjusted mother liquor, as determined as described in Reference Example 8 hereinabove, was 3.0 micrometer, the respective Dv50 value was 4.9 micrometer, and the respective Dv90 value was 8.1 micrometer.
c) Separation
  From the pH-adjusted mother liquor obtained in b), the B-MWW precursor was separated by filtration using different types of filtration devices (suction filter with filter material Sefar Tetex® Mono 24-1100-SK 012, centrifugal filter, candle filter). For all filtration devices, the filtration resistance of the pH-adjusted mother liquor obtained in b) was (30+/−10) mPa*s/m$^2$ as determined as described in Reference Example 9 hereinabove.
  The filter cake was then washed with de-ionized water until the washing water had a conductivity of less than 200 microSiemens/cm.
  The washing resistance of the pH-adjusted mother liquor obtained in b) was (30+/−10)mPa*s/m$^2$ as determined as described in Reference Example 9 hereinabove.
d) Spray-Drying and Calcination
  From the washed filter cake obtained according to c) an aqueous suspension was prepared having a solids content of 15 weight-%. This suspension was subjected to spray-drying in a spray-tower with the following spray-drying conditions:
drying gas, nozzle gas: technical nitrogen
temperature drying gas:
  temperature spray tower (in): 270-340° C.
  temperature spray tower (out): 150-167° C.
  temperature filter (in): 140-160° C.
  temperature scrubber (in): 50-60° C.
  temperature scrubber (out): 34-36° C.
pressure difference filter: 8.3-10.3 mbar
nozzle:
  two-component nozzle supplier Gerig; size 0
  nozzle gas temperature: room temperature
  nozzle gas pressure: 2.5 bar
operation mode: nitrogen straight
apparatus used: spray tower with one nozzle
configuration: spray tower-filter-scrubber
gas flow: 1900 kg/h
filter material: Nomex® needle-felt 20 m$^2$
dosage via flexible tube pump: SP VF 15 (supplier: Verder)
  The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.
  The spray-dried material was then subjected to calcination at 650° C. in a rotary calciner with a throughput in the range of from 0.8 to 1.0 kg/h.
  The obtained zeolitic material BMWW had a boron content of 1.3 weight-%, a silicon content of 45 weight-%, a total organic carbon (TOC) content of <0.1 weight-% and a crystallinity of 82%, determined by XRD according to Reference Example 10. The BET specific surface area determined via nitrogen adsorption at 77 K according to DIN 66134 was 463 m$^2$/g, the pore volume determined according to Hg porosimetry according to DIN 66133 was 5.2 mL/g, the particle size distribution Dv10 was 5.7 micrometer, Dv50 was 10.56 micrometer, and Dv90 was 18.8 micrometer.

Example 5.2

Preparation of a Spray Powder Containing Deboronated BMWW a) Deboronation
  1485 kg water were passed into a vessel equipped with a reflux condenser. Under stirring at 40 r.p.m., 99 kg of the spray-dried material obtained according to Example 5.1 were suspended into the water. Subsequently, the vessel was closed and the reflux condenser put into operation. The stirring rate was increased to 70 r.p.m. Under stirring at 70 r.p.m., the content of the vessel was heated to 100° C. within 10 h and kept at this temperature for 10 h. Then, the content of the vessel was cooled to a temperature of less than 50° C.

The resulting deboronated zeolitic material having an MWW framework structure was separated from the suspension by filtration under a nitrogen pressure of 2.5 bar and washed four times with deionized water. After the filtration, the filter cake was dried in a nitrogen stream for 6 h.

The obtained deboronated zeolitic material having an MWW framework structure had a residual moisture content of 80%, as determined using an IR (infrared) scale at 160° C.

b) Spray-Drying and Calcination

From the nitrogen-dried filter cake having a residual moisture content of 79% obtained according to section c) above, an aqueous suspension was prepared with deionized water, the suspension having a solid content of 15 weight-%. This suspension was subjected to spray-drying in a spray-tower with the following spray-drying conditions:

drying gas, nozzle gas: technical nitrogen
temperature drying gas:
    temperature spray tower (in): 290-310° C.
    temperature spray tower (out): 140-160° C.
    temperature filter (in): 140-160° C.
    temperature scrubber (in): 40-60° C.
    temperature scrubber (out): 20-40° C.
pressure difference filter: 6.0-10.0 mbar
nozzle:
    two-component nozzle: supplier Niro, diameter 4 mm
    nozzle gas pressure: 2.5 bar
operation mode: nitrogen straight
apparatus used: spray tower with one nozzle
configuration: spray tower-filter-scrubber
gas flow: 1900 kg/h
filter material: Nomex® needle-felt 20 m$^2$
dosage via flexible tube pump: VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged.

The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

Characterization

The obtained spray-dried zeolitic material having an MWW framework structure had a boron content of 0.08 weight-%, a silicon content of 45 weight-%, a total organic carbon (TOC) content of <0.1 weight-%, and a crystallinity of 79%, determined a by XRD according to Reference Example 10. The BET specific surface area determined via nitrogen adsorption at 77K according to DIN 66134 was 451 m$^2$/g, the pore volume determined according to Hg porosimetry according to DIN 66133 was 4.99 mUg. The particle size distribution was characterized by Dv10 of 5.6 micrometer, Dv50 of 11.1 micrometer, and Dv90 of 24.1 micrometer.

Example 5.3

Preparation of a TiMWW Spray Powder a) Hydrothermal Synthesis

Based on the zeolitic material having an MWW framework structure as obtained according to Example 5.2, a titanium zeolitic material having an MWW framework structure was prepared.

Starting materials:
    deionized water: 263 kg
    piperidine: 97 kg
    tetrabutylorthotitanate: 13.8 kg
    zeolitic material obtained according to 5.2: 64 kg 64 kg of the zeolitic material having an MWW framework structure were transferred in to a first vessel A.

In a second vessel B, 150 kg deionized water were transferred and stirred at 80 r.p.m. 97 kg piperidine were added under stirring, and during addition, the temperature of the mixture increased for about 15° C. Subsequently, 12.8 kg tetrabutylorthotitanate and 23 kg deionized water were added. Stirring was then continued for 60 min.

The mixture of vessel B was then transferred into vessel A, and stirring in vessel A was started (70 r.p.m.). 90.00 kg deionized water were filled into vessel A and transferred to vessel B.

After said stirring at 70 r.p.m., the frequency was decreased to 50 r.p.m., and the mixture in vessel B was heated to a temperature of 170° C. within 5 h. At a constant stirring rate of 50 r.p.m., the temperature of the mixture in vessel B was kept at an essentially constant temperature of 170° C. for 48 h under autogenous pressure. During this crystallization of titanium-containing zeolitic material having an MWW framework structure, a pressure increase of up to 10 bar was observed. Subsequently, the obtained suspension containing the titanium-containing zeolitic material having an MWW framework structure was cooled within 5 h.

b) Spray-Drying

The obtained suspension was diluted with water to have a concentration of water of 85 weight-% and directly subjected to spray-drying in a spray-tower with the following spray-drying conditions:

drying gas, nozzle gas: technical nitrogen
temperature drying gas:
    temperature spray tower (in): 290-310° C.
    temperature spray tower (out): 150-170° C.
    temperature filter (in): 150-170° C.
    temperature scrubber (in): 30-50° C.
    temperature scrubber (out): 30-50° C.
pressure difference filter: 6.0-10.0 mbar
nozzle:
    two-component nozzle: supplier Niro, diameter 4 mm
    nozzle gas pressure: 1.5 bar
operation mode: nitrogen straight
apparatus used: spray tower with one nozzle
configuration: spray tower-filter-scrubber
gas flow: 1800 kg/h
filter material: Nomex® needle-felt 20 m$^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

Characterization

The spray-dried titanium-containing zeolitic material having an MWW framework structure had a silicon content of 36 weight-%, a titanium content of 2.4 weight-%, a total organic carbon (TOC) content of 11 weight-%, a nitrogen content of 2.3 weight-%, and a crystallinity of 79%, determined by XRD according to Reference Example 10. The particle size distribution Dv10 was 5.3 micrometer, Dv50 was 11.8 micrometer, and Dv90 was 44.0 micrometer.

c) Acid Treatment

The spray-dried titanium-containing zeolitic material having an MWW framework structure as obtained in b) was subjected to acid treatment as described in the following Starting materials:
  deionized water: 1233 kg
  nitric acid (10% aqueous solution) 287 kg
  spray-dried Ti-MWW obtained according to b): 76 kg
  1233 kg deionized water were filled in a vessel. 287 kg nitric acid were added, and 76 kg of the spray-dried titanium-containing zeolitic material having an MWW framework structure were added under stirring at 50 r.p.m. The resulting mixture was stirred for another 15 min. Subsequently, the stirring rate was increased to 70 r.p.m.

The mixture in the vessel was heated to 100° C. and kept at this temperature and under autogenous pressure for 1 h under stirring. The thus obtained mixture was then cooled within 1 h to a temperature of less than 50° C.

d) Separation

The cooled mixture was subjected to filtration, and the filter cake was washed six times with deionized water under a nitrogen pressure of 2.5 bar.

e) Spray-Drying

From the filter cake obtained from v), an aqueous suspension was prepared with deionized water, the suspension having a solid content of 85 weight-%. This suspension was subjected to spray-drying in a spray-tower with the following spray-drying conditions:
drying gas, nozzle gas: technical nitrogen
temperature drying gas:
  temperature spray tower (in): 200-330° C.
  temperature spray tower (out): 140-165° C.
  temperature filter (in): 140-160° C.
  temperature scrubber (in): 50-60° C.
  temperature scrubber (out): 20-40° C.
pressure difference filter: 7.0-11.0 mbar
nozzle:
  two-component nozzle: supplier Niro, diameter 4 mm
  nozzle gas throughput: 23 kg/h
  nozzle gas pressure: 2.5 bar
operation mode: nitrogen straight
apparatus used: spray tower with one nozzle
configuration: spray tower-filter-scrubber
gas flow: 1900 kg/h
filter material: Nomex® needle-felt 20 m²
dosage via flexible tube pump: S VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

Characterization

The spray-dried acid-treated titanium-containing zeolitic material having an MWW framework structure material had a silicon content of 40 weight-%, a titanium content of 1.6 weight-%, and a total organic carbon (TOC) content of 2.0 weight-%.

f) Calcination

The spray-dried material was then subjected to calcination at 650° C. in a rotary calciner with a throughput of 0.8-1.0 kg/h.

Characterization

The calcined material had a silicon content of 44 weight-%, a titanium content of 1.8 weight-% and a total organic carbon (TOC) content of less than 0.1 weight-%. The lattice parameter c of the framework structure has a value of 25.2±0.2 Angstrom, as determined via XRD. The UV/VIS spectrum showed a band with a maximum in the range of from 200 to 215 nm, wherein the UV/VIS spectrum showed no band with a maximum in the range of above 250 nm. The Langmuir surface is determined via nitrogen adsorption at 77 K according to DIN 66134 was 634 m²/g, the multipoint BET specific surface area determined via nitrogen adsorption at 77 K according to DIN 66134 was 458 m²/g. The degree of crystallization determined via XRD was 84% according to Reference Example 10, the average crystallite size 30.5 nm. The particle size distribution the particle size distribution Dv10 was 4.5 micrometer, Dv50 was 8.5 micrometer, and Dv90 was 14.6 micrometer.

Example 5.4

Preparation of a ZnTiMWW Spray Powder

The acid-treated, spray-dried and calcined material obtained in in Example 5.3 (TiMWW) was then subjected to an impregnation stage.
  Starting materials:
    deionized water: 1566.0 kg
    zinc acetate dihydrate: 9.58 kg
    calcined TiMWW: 52.2 kg
  Impregnation was carried out in 2 batches a) to b) as follows:
  a) In a vessel equipped with a reflux condenser, a solution of 981 kg deionized water and 6.0 kg zinc acetate dihydrate was prepared within 30 min. Under stirring (40 r.p.m.), 32.7 kg of the calcined TiMWW material were suspended. Subsequently, the vessel was closed and the reflux condenser put into operation. The stirring rate was increased to 70 r.p.m.
  b) In a vessel equipped with a reflux condenser, a solution of 585 kg deionized water and 3.58 kg zinc acetate dihydrate was prepared within 30 min. Under stirring (40 r.p.m.), 19.5 kg of the calcined TiMWW material were suspended.

Subsequently, the vessel was closed and the reflux condenser put into operation. The stirring rate was increased to 70 r.p.m.

In all batches a) and b), the mixture in the vessel was heated to 100° C. within 1 h and kept under reflux for 2 h at a stirring rate of 70 r.p.m. Then, the mixture was cooled within 2 h to a temperature of less than 50° C. For each batch a) and b), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h.

In total 297 kg of nitrogen dried filter cake were obtained.

The thus dried Zn-impregnated TiMWW material (Zn-TiMWW), had a Si content of 42 weight-%, a Ti content of 1.8 weight-%, a Zn content of 1.3 weight-%.

From 297 kg of the mixture of the filter cake obtained above, an aqueous suspension was prepared with deionized water, the suspension having a solid content of 15 wt.-%. This suspension was subjected to spray-drying in a spray-tower with the following spray-drying conditions:
   apparatus used: spray tower with one nozzle
   operation mode: nitrogen straight
   configuration: dehumidifier-filter-scrubber
   dosage:
      flexible-tube pump VF 10 (supplier: Verder)
      nozzle with a diameter of 4 mm (supplier: Niro)
   filter material: Nomex® needle-felt 10 m²

|  |  | Runtime/h | | | | |
|---|---|---|---|---|---|---|
|  |  | 0.5 | 1.5 | 2.5 | 3.5 | 4.5 |
| Flow rate gas/(kg/h) | | 550 | 550 | 550 | 550 | 550 |
| Temperature drying gas/° C. | spray tower (in) | 305 | 305 | 305 | 305 | 305 |
|  | spray tower (out) | 151 | 151 | 151 | 151 | 151 |
|  | Filter (in) | 140 | 137 | 130 | 127 | 126 |
|  | Scrubber (in) | 110 | 110 | 110 | 108 | 105 |
|  | Scrubber (out) | 14 | 14 | 15 | 15 | 15 |
| Differential pressure/ mbar | spray tower | 3.1 | 3 | 3 | 2.8 | 2.9 |
|  | Filter | 1.7 | 1.7 | 1.8 | 1.8 | 2.1 |
|  | Scrubber | 3.8 | 4.1 | 4.2 | 4.2 | 4.2 |
| Pressure/ mbar | spray tower | −103 | −1.2 | −0.9 | −0.9 | −1.1 |
| Nozzle gas | Flow rate kg/h | 23 | 23 | 23 | 23 | 23 |
|  | Temperature/° C. | r.t.*⁾ | r.t.*⁾ | r.t.*⁾ | r.t.*⁾ | r.t.*⁾ |
|  | Pressure/bar | 2.5 | 2.5 | 2.5 | 2.5 | 2.5 |
| Spray-dried product | Temperature/° C. | r.t.*⁾ | r.t.*⁾ | r.t.*⁾ | r.t.*⁾ | r.t.*⁾ |

*⁾room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material thus obtained had a Zn content of 1.4 weight-%, a Ti content of 1.7 weight-%, a Si content of 41 weight-%, and a TOC content of <0.5 weight-%.

The spray-dried product was then subjected to calcination for 2 h at 650° C. under air in a rotary furnace, yielding 43.8 kg of calcined spray-dried ZnTiMWW.

Characterization of the Calcined Spray-Dried Micropowder:

The calcined spray-dried material thus obtained had a Zn content of 1.3 weight-%, a Ti content of 1.8 weight-%, a Si content of 42.5 weight-%, and a C content of <0.1 weight-%.

The bulk density of the calcined spray-dried ZnTiMWW was 90 g/l (gram/liter).

The mesopores of the micropowder had an average pore diameter (4V/A) of 27.2 nm as determined by Hg porosimetry according to DIN 66133.

The macropores of the micropowder had an average pore diameter (4V/A) of 95.6 nm as determined by Hg porosimetry according to DIN 66133.

The micropores of the ZnTiMWW contained in the micropowder had an average pore diameter of 1.06 nm as determined by nitrogen adsorption according to DIN 66134 (Horward-Kawazoe method).

The Dv10 value of the particles of the micropowder as determined according to Reference Example 8 was 4.10 micrometers. The Dv50 value of the particles of the micropowder as determined according to Reference Example 8 was 8.19 micrometers. The Dv90 value of the particles of the micropowder as determined according to Reference Example 8 was 14.04 micrometers.

The degree of crystallization determined via XRD according to Reference Example 10 was 77%+/−10%, the average crystallite size 35.0 nm+/−10%. It was found that the crystalline phase exhibits a pure MWW structure. No other crystalline titania phases such as anatase, rutile or brookite, or crystalline zinc silicate ($Zn_2SiO_4$) such as willemite could be detected.

The XRD spectrum of the calcined spray-dried ZnTiMWW micropowder is shown in FIG. 20.

Other Characteristics:

The Langmuir surface are determined via nitrogen adsorption at 77 K according to DIN 66134 was 610 m²/g, the multipoint BET specific surface area determined via nitrogen adsorption at 77 K according to DIN 66134 was 440 m²/g. The total intrusion volume determined according to Hg porosimetry according to DIN 66133 was 5.1 ml/g (milliliter/gram), the respective total pore area 88.6 m²/g.

Example 5.5

Preparation of a Molding Containing the ZnTiMWW Spray Powder

Starting from the calcined spray-dried ZnTiMWW material obtained above, a molding was prepared, dried, and calcined. Therefor, 12 batches were prepared, each starting from 3.5 kg of the calcined spray-dried ZnTiMWW material obtained according to Example 5.4, 0.226 kg Walocel™ (Walocel MW 15000 GB, Wolff Cellulosics GmbH & Co. KG, Germany), 2.188 kg Ludox® AS-40 and 6.6 l deionized water, as follows:

3.5 kg ZnTiMWW and 0.226 kg Walocel were subjected to kneading in an edge mill for 5 min. Then, during further kneading, 2.188 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length.

The strands thus obtained were dried for 16 h at 120° C. in a drying chamber under air.

In total (sum of the 12 batches), 56 kg white strands with a diameter of 1.7 mm were obtained.

56 kg of the dried strands were subjected to calcination in a rotary furnace at 550° C. for 1 h under air, yielding 52 kg calcined strands. Thereafter, the strands were sieved (mesh size 1.5 mm), and the yield, after sieving, was 50.0 kg.

Characterization of the Strands

The thus obtained moldings exhibited a bulk density of 322 g/l (gram per liter) and had a Zn content of 1.1 weight-%, a Ti content of 1.4 weight-%, a Si content of 43 weight-%, and a C content of <0.1 weight-%.

The mesopores of the micropowder had an average pore diameter (4V/A) of 20.9 nm as determined by Hg porosimetry according to DIN 66133.

The macropores of the micropowder had an average pore diameter (4V/A) of 50.0 nm as determined by Hg porosimetry according to DIN 66133.

The degree of crystallization determined via XRD was 70+/−%, the average crystallite size 32.5 nm+/−10%.

The XRD diffraction pattern of the material is shown in FIG. 25.

The crush strength of the moldings as determined according to the method using a crush strength test machine Z2.5/TS1S was 4.4 N (standard deviation: 0.5 N). The minimum value found when testing the 10 samples was 3.5 N, the maximum value 5.1 N.

The $^{29}$Si MAS NMR is shown in FIG. 21. After the curve had been deconvolved by the proper Gaussian-Lorentzian line shapes, six peaks were clearly observed.

The $Q^3/Q^4$ ratio as determined according to Reference Example 4 was found to be 2.2.

The total amount of adsorbed water as determined according to Reference Example 6 of the molding was 6.9 weight-%. The respective adsorption/desorption isotherms are shown in FIG. 27.

Other Characteristics:

The Langmuir surface are determined via nitrogen adsorption at 77 K according to DIN 66133 was 518 m$^2$/g, the multipoint BET specific surface area determined via nitrogen adsorption at 77 K according to DIN 66133 was 373 m$^2$/g. The total intrusion volume (please explain) determined according to Hg porosimetry according to DIN 66133 was 1.3 ml/g (milliliter/gram), the respective total pore area 100.2 m$^2$/g.

It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Example 5.6

Water Treatment of the Molding Containing the ZnTiMWW Spray Powder

Starting from the calcined strands, a post-treatment stage was performed as follows:

1000 kg deionized water were filled in a vessel. Then, 50 kg of the calcined moldings were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h.

The water-treated strands were subjected to filtration and washed with deionized water.

The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 49.1 kg.

Characterization of the Strands Obtained According to Post-Treatment:

The thus obtained water-treated moldings exhibited a bulk density of 332 g/l (gram per liter) and had a Zn content of 1.1 weight-%, a Ti content of 1.4 weight-%, a Si content of 42 weight-%, and a C content of <0.10 weight-%.

The mesopores of the micropowder had an average pore diameter (4V/A) of 22.1 nm as determined by Hg porosimetry according to DIN 66133. Thus, the inventive water treatment has practically no influence on the mesopore characteristics of the molding (cf. the molding according to Example 5.4, having a respective average pore diameter 20.9 of nm).

The macropores of the micropowder had an average pore diameter (4V/A) of 52.0 nm as determined by Hg porosimetry according to DIN 66133. Thus, the inventive water treatment has practically no influence on the macropore characteristics of the molding (cf. the molding according to Example 5.4, having a respective average pore diameter of 50.0 nm).

The degree of crystallization determined via XRD was 69%+/−10%, the average crystallite size 30.5 nm+/−10%. Thus, while not having a significant influence on the average crystallite size (cf. Example 5.5: 32.0 nm+/−10%), the inventive water treatment had an influence on the degree of crystallization which is decreased from a value of 70% (cf. Example 5.5) to a value of 69%.

The XRD diffraction pattern of the material is shown in FIG. 26.

The crush strength of the moldings as determined according to the method using a crush strength test machine Z2.5/TS1S was 13.7 N (standard deviation: 2.5). The minimum value found when testing the 10 samples was 10.2 N, the maximum value 17.6 N. These values clearly show that the inventive water treatment of the ZnTiMWW micropowder containing molding leads to a significant increase in the mechanical resistance of the molding (cf. the non-water treated moldings according to Example 5.5 having a crush strength of only 4,4 N). Due to the fact that in industrial-scale processes where such moldings are preferably employed as catalysts in continuous processes, and due to the fact that the preferred use of the moldings in these processes is in the form of fixed-bed catalysts which are exposed to a continuous mechanical stress, the inventive water treatment allows for significantly improving the mechanical suitability of the moldings.

The $^{29}$Si MAS NMR is shown in FIG. 22. After the curve had been deconvolved by the proper Gaussian-Lorentzian line shapes, six peaks were clearly observed.

The $Q^3/Q^4$ ratio as determined according to Reference Example 4 was found to be 1.39. Clearly, the $Q^3/Q^4$ was considerably decreased by the inventive water treatment from 2.20 to 1.39.

The total amount of adsorbed water as determined according to Reference Example 6 of the molding was 6.7 weight-%. Therefore, it is clearly shown that the inventive water treatment increases the hydrophobicity of the molding. The respective adsorption/desorption isotherms are shown in FIG. 27.

The intensity ratio of the infrared band in the region of 3708+/−20 cm$^{-1}$ attributed to the free silanol groups, relative to the infrared band in the region of 3688+/−20 cm$^{-1}$ attributed to vicinal silanol groups was smaller than 1.35. Compared to the respective intensity ratio of the non-water-treated molding according to Example 5.4 (respective intensity ratio of 1.9), the intensity ratio was decreased. The IR spectrum of the molding according to Example 5.5 is shown in FIG. 23, the IR spectrum of the molding according to Example 5.6 is shown in FIG. 24.

Other Characteristics

The Langmuir surface are determined via nitrogen adsorption at 77 K according to DIN 66133 was 421 m$^2$/g, the multipoint BET specific surface area determined via nitrogen adsorption at 77 K according to DIN 66133 was 303 m$^2$/g. The total intrusion volume determined according to Hg porosimetry according to DIN 66133 was 1.3 ml/g (milliliter/gram), the respective total pore area 98.7 m$^2$/g.

It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Example 5.7

Test of the Moldings as Catalyst for the Epoxidation of Propene

Catalytic Test of the Micropowder According to the Present Invention

The Zn/Ti-MWW micropowder was subjected to the PO test. The following value was obtained:
PO test 14.6%

Clearly, the PO test shows that the micropowder according to present may serve as a good catalyst for the preparation of propylene oxide from propene in acetonitrile as solvent, using hydrogen peroxide as oxidizing agent.

The Extrudates of Zn/Ti-MWW

The non-water-treated molding containing the Zn/Ti-MWW micropowder was subjected to the PO test. The following value was obtained:
PO test 8.1%

The water-treated molding containing the Zn/Ti-MWW micropowder was subjected to the PO test. The following value was obtained:
PO test of 8.4

Clearly, the PO test shows that both the non-water-treated and the water-treated moldings according to present serve as a good catalyst for the preparation of propylene oxide from propene in acetonitrile as solvent, using hydrogen peroxide as oxidizing agent. Although containing binder material, the non-water-treated molding still exhibits a very good PO test value compared to the pure micropowder. The water-treated molding exhibits an even better PO test value showing the advantageous impact of the inventive water treatment of the moldings.

SHORT DESCRIPTION OF THE FIGURES

Figure 1:
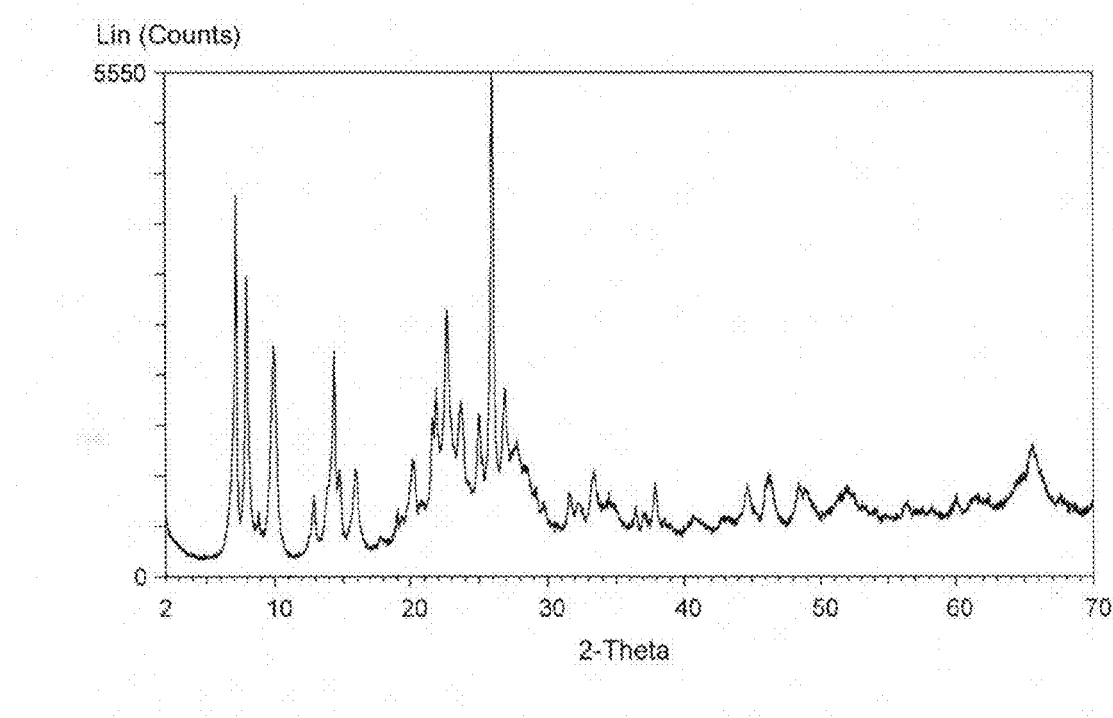
FIG. 1 shows the X-ray diffraction pattern (copper K alpha radiation) of the acid-treated, spray-dried and calcined TiMWW material as obtained according to Reference Example 1.4. On the x axis, the degree values (2 Theta) are shown, on the y axis, the intensity (Lin (Counts)).
Figure 2:
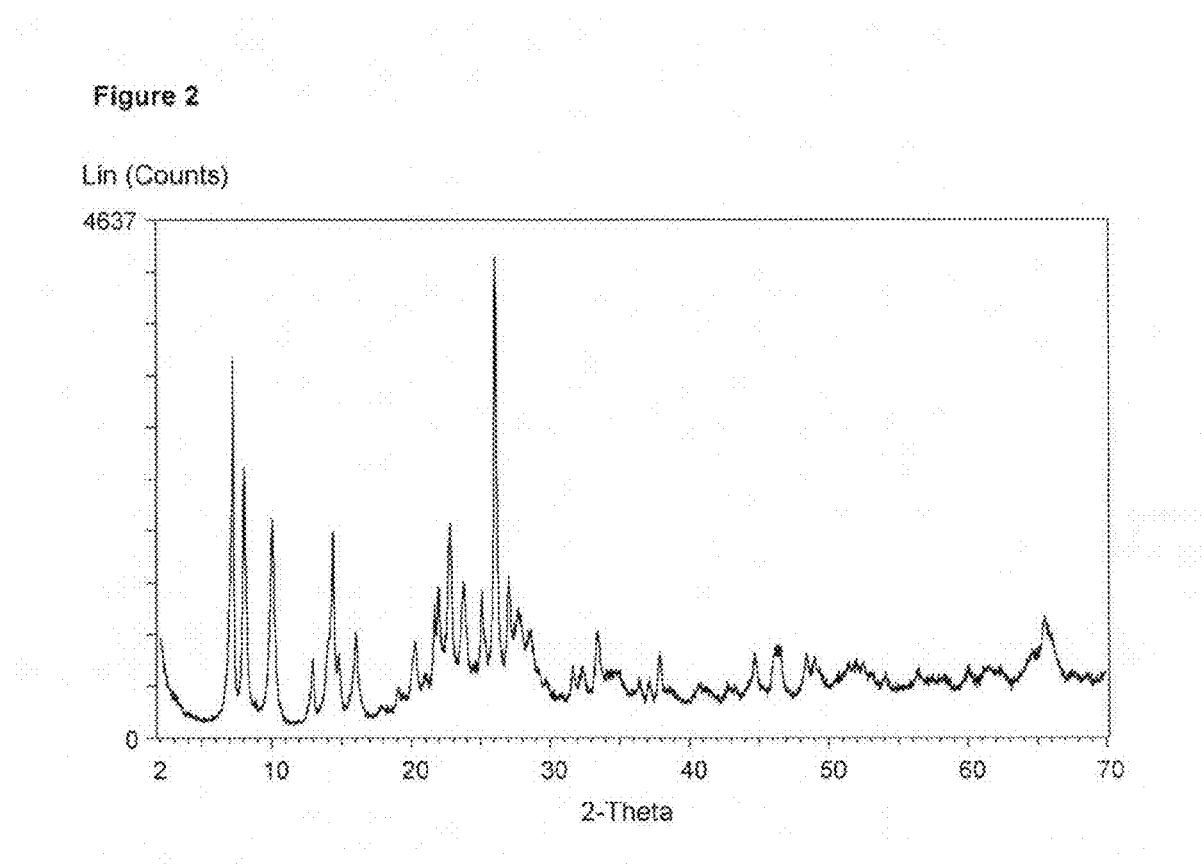
FIG. 2 shows the X-ray diffraction pattern (copper K alpha radiation) of the calcined spray-dried ZnTiMWW material as obtained according to Example 1. On the x axis, the degree values (2 Theta) are shown, on the y axis, the intensity (Lin (Counts)).
Figure 3:
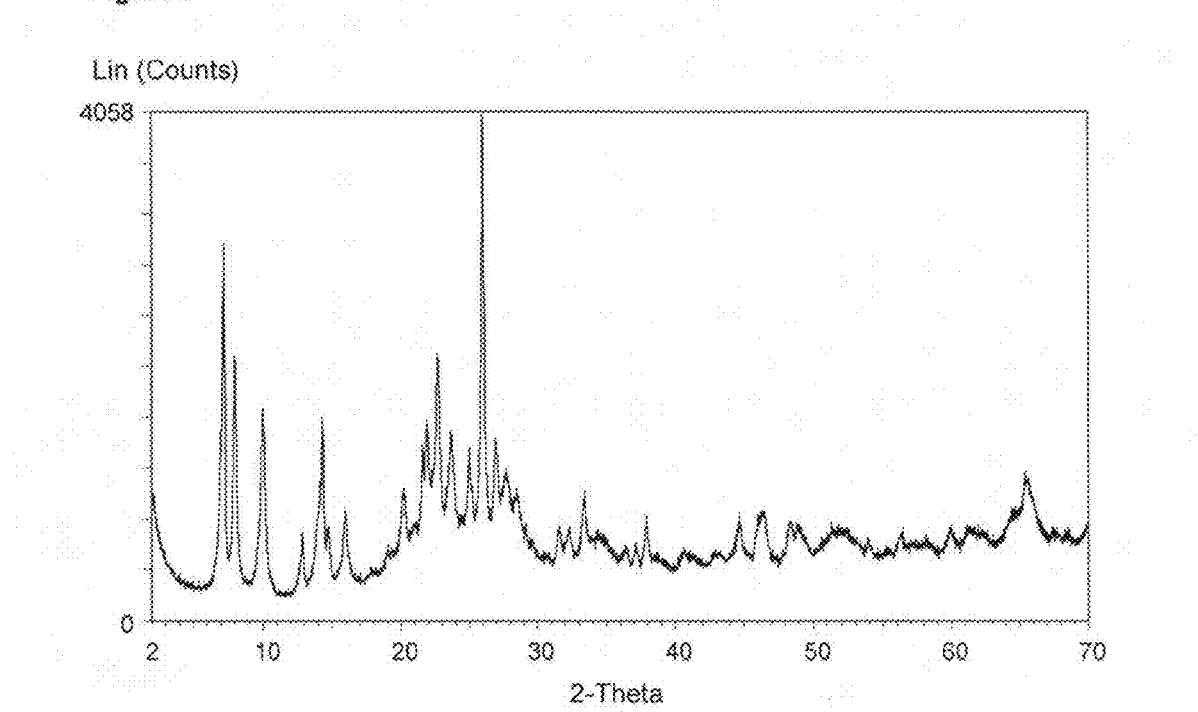
FIG. 3 shows the X-ray diffraction pattern (copper K alpha radiation) of the calcined molded ZnTiMWW material as obtained according to Example 2. On the x axis, the degree values (2 Theta) are shown, on the y axis, the intensity (Lin (Counts)).
Figure 4:
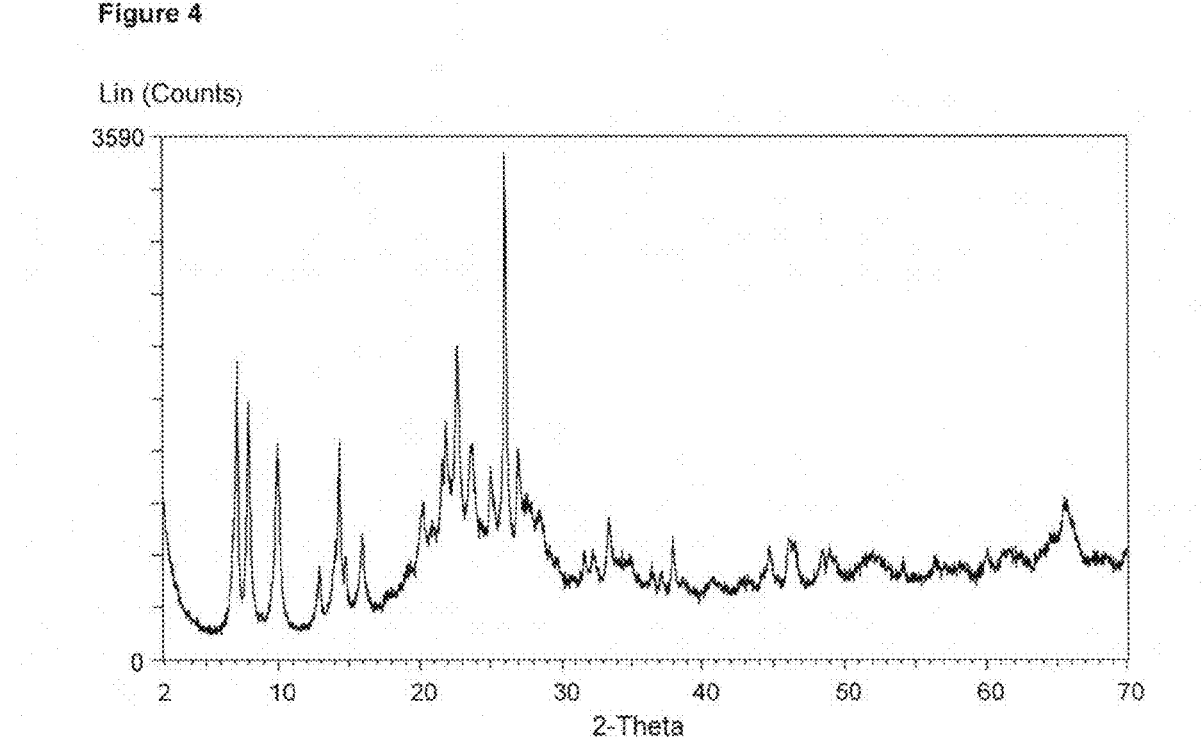
FIG. 4 shows the X-ray diffraction pattern (copper K alpha radiation) of the calcined molded and water-treated ZnTiMWW material as obtained according to Example 3. On the x axis, the degree values (2 Theta) are shown, on the y axis, the intensity (Lin (Counts)).
Figure 5:
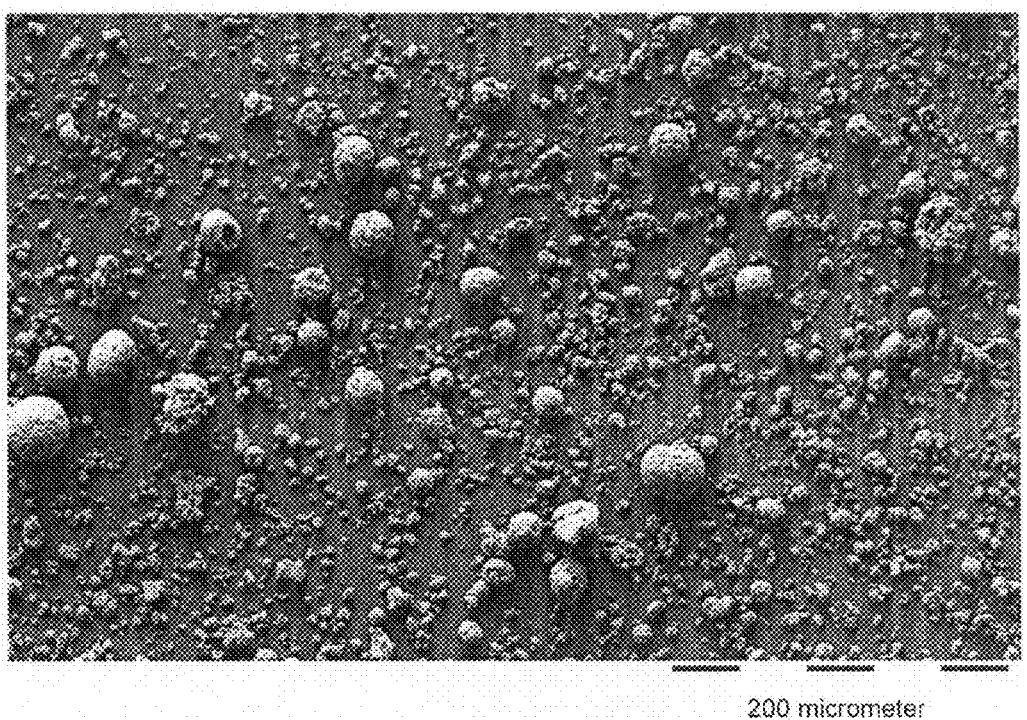
FIG. 5 shows an SEM (Scanning Electron Microscopy) picture (secondary electron (SE) picture at 5 kV (kiloVolt)) of a representative sample of the spray-dried calcined ZnTiMWW material as obtained according to Example 1. The scale is indicated in the lower right hand corner by the rule having a length of 200 micrometer.
Figure 6:
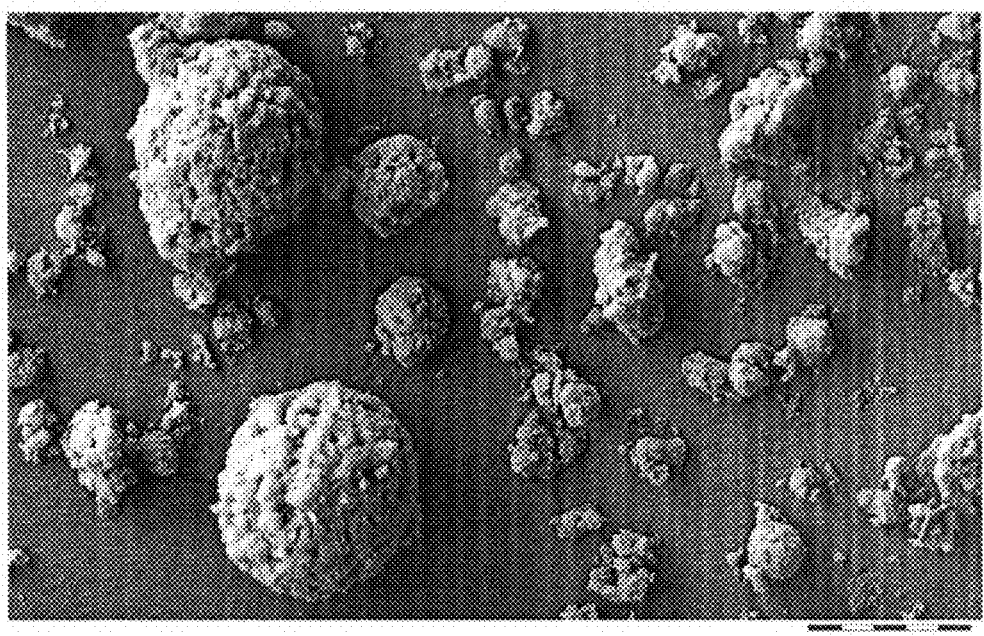
FIG. 6 shows an SEM (Scanning Electron Microscopy) picture (secondary electron (SE) picture at 5 kV (kiloVolt)) of a representative sample of the spray-dried calcined ZnTiMWW material as obtained according to Example 1. The scale is indicated in the lower right hand corner by the rule having a length of 20 micrometer.
Figure 7:
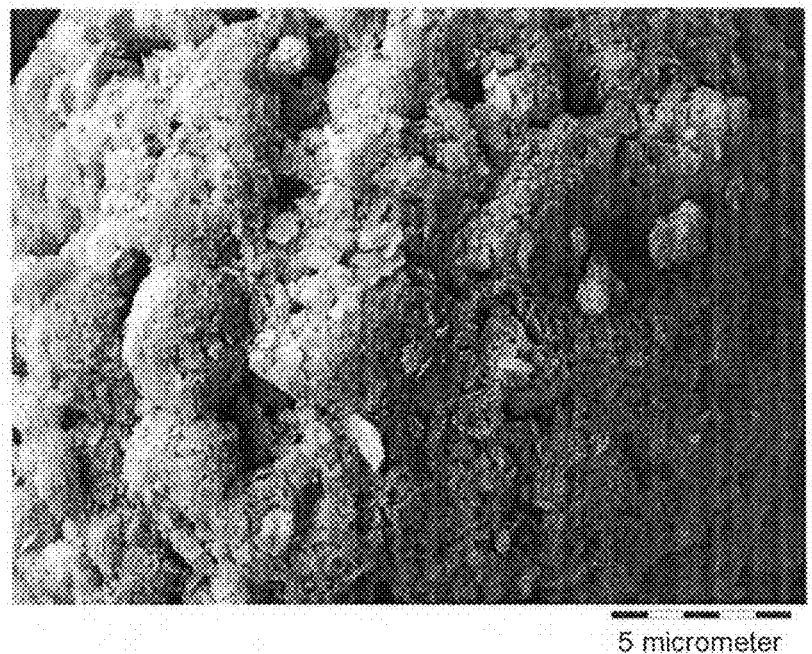
FIG. 7 shows an SEM (Scanning Electron Microscopy) picture (secondary electron (SE) picture at 5 kV (kiloVolt)) of a representative sample of the spray-dried calcined ZnTiMWW material as obtained according to Example 1. The scale is indicated in the lower right hand corner by the rule having a length of 5 micrometer.
Figure 8:
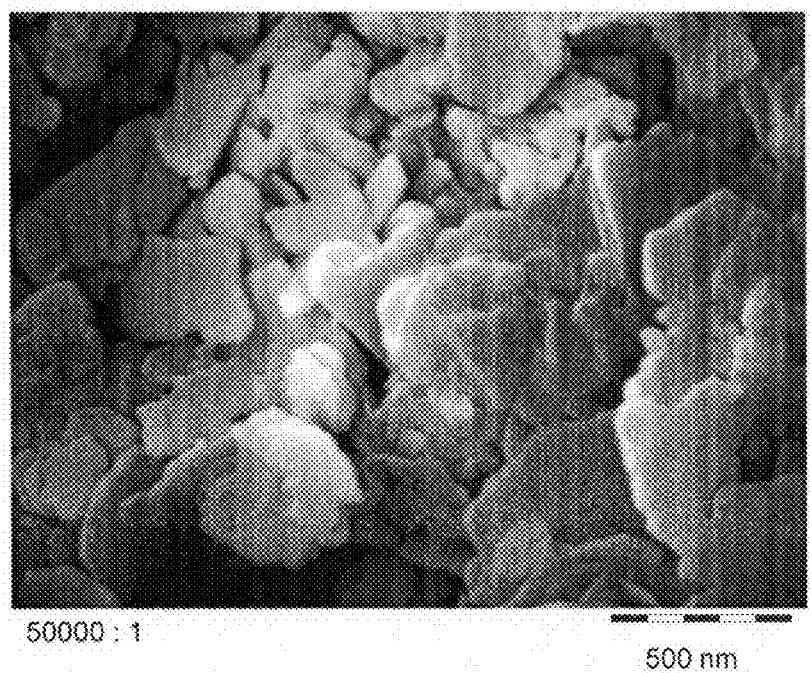
FIG. 8 shows an SEM (Scanning Electron Microscopy) picture (secondary electron (SE) picture at 5 kV (kiloVolt)) of a representative sample of the spray-dried calcined ZnTiMWW material as obtained according to Example 1. The scale is indicated in the lower right hand corner by the rule having a length of 500 nanometer.
Figure 9:
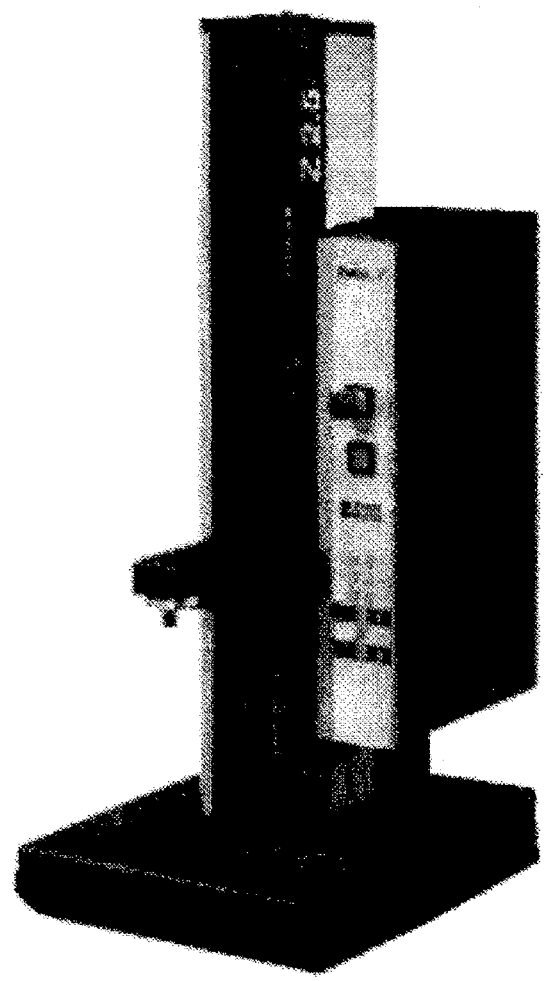
FIG. 9 shows the title page of the instruction manual of the Zwick crush strength testing machine referred to in Reference Example 2.
Figure 10:
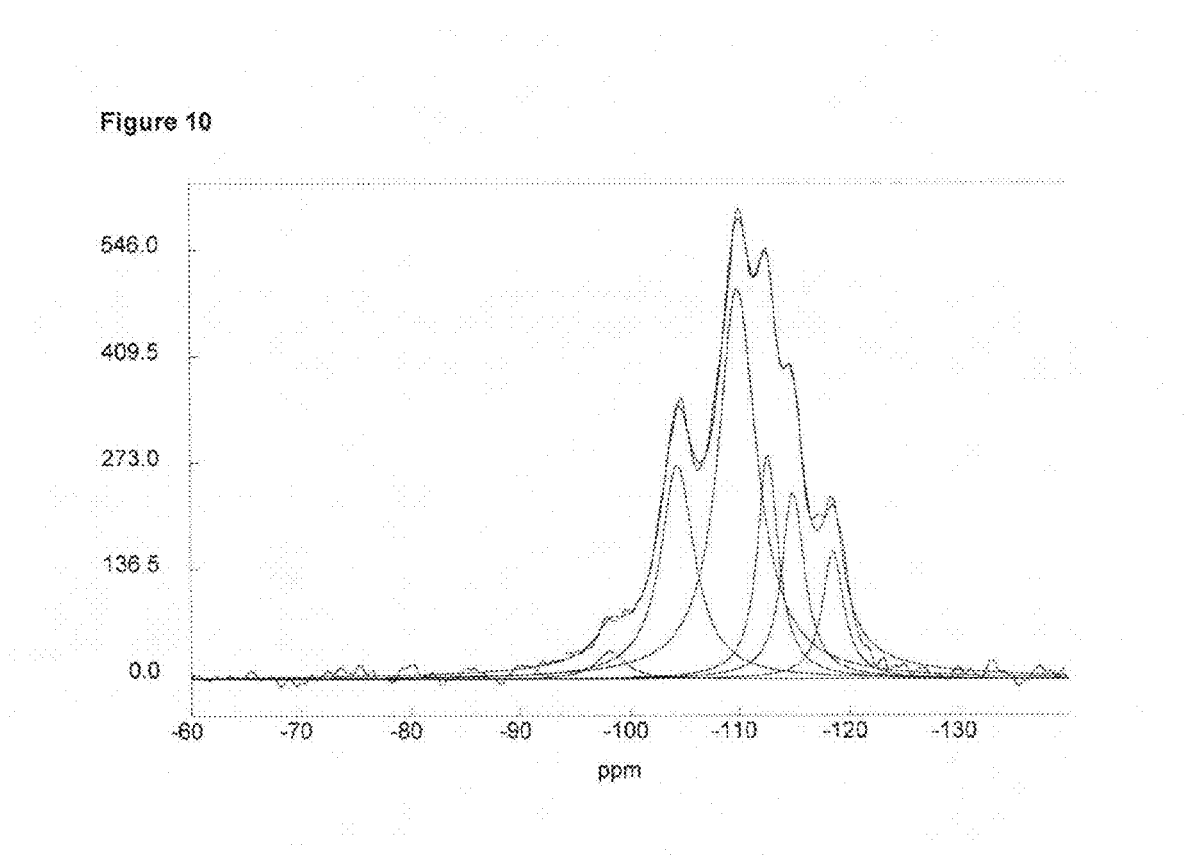

FIG. 10 shows the $^{29}$Si MAS NMR spectrum of the material as obtained from Example 2. On the x axis, the shifts are shown in ppm. FIG. 10 additionally shows the six peaks obtained after having deconvolved by the proper Gaussian-Lorentzian line shapes.

Figure 11:
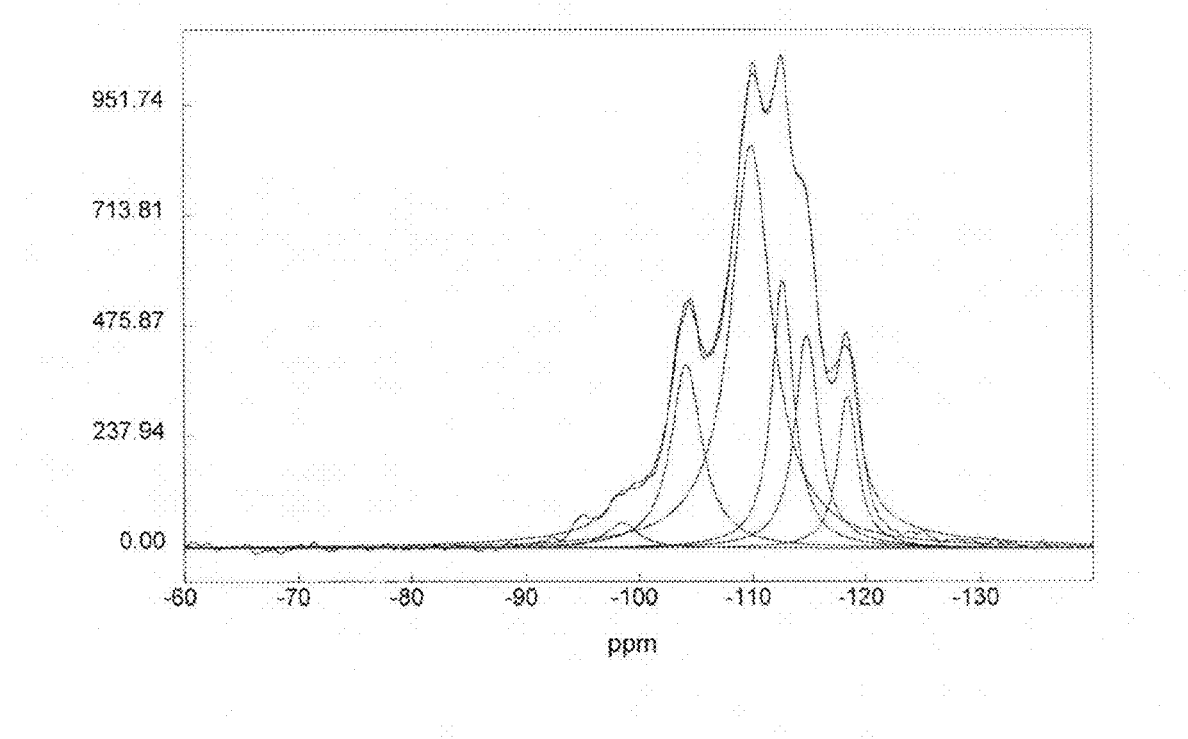

FIG. 11 shows the $^{29}$Si MAS NMR spectrum of the material as obtained from Example 3. On the x axis, the shifts are shown in ppm. FIG. 11 additionally shows the six peaks obtained after having deconvolved by the proper Gaussian-Lorentzian line shapes.

Figure 12:
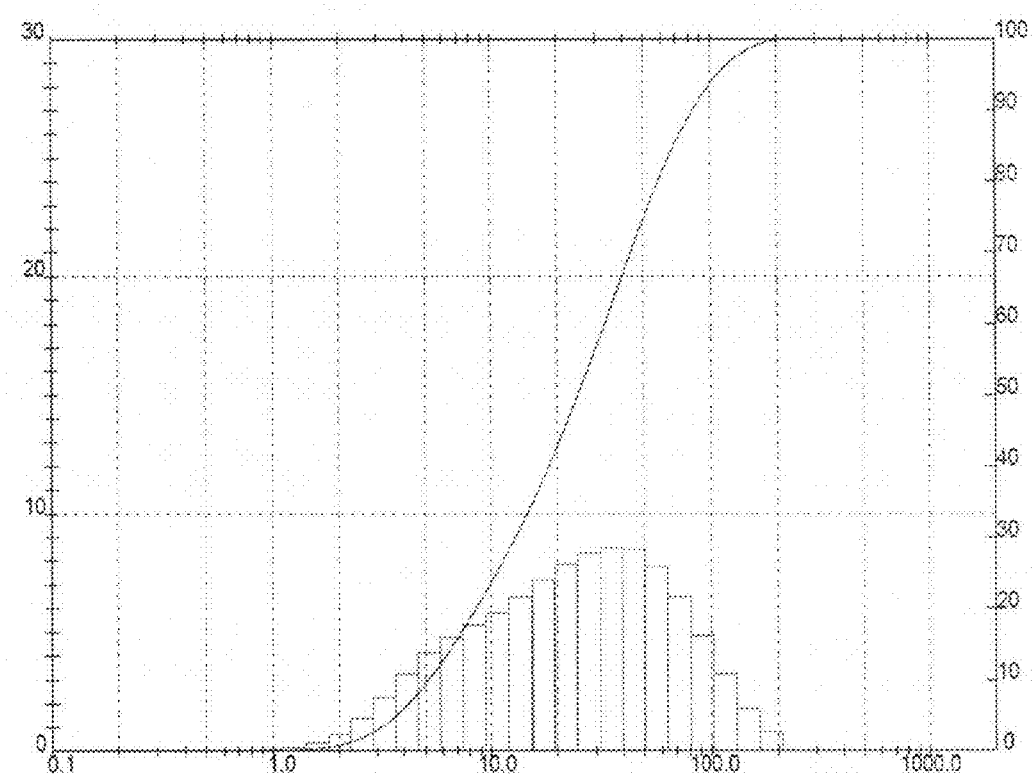

FIG. 12 shows the result of the determination of the Dv10, Dv50, and Dv90 values of the micropowder as obtained according to Example 1. As to the parameters used for the determination, reference is made to Reference Example 8. On the x axis, the particle diameter/micrometer is shown. On the left and right y axis, the volume-% of the particles of the micropowder is shown. The values of the left y axis refer to the distribution as indicated by the rectangles whereas the values of the right y axis refer to the distribution as indicated by the integral curve.

Figure 13:
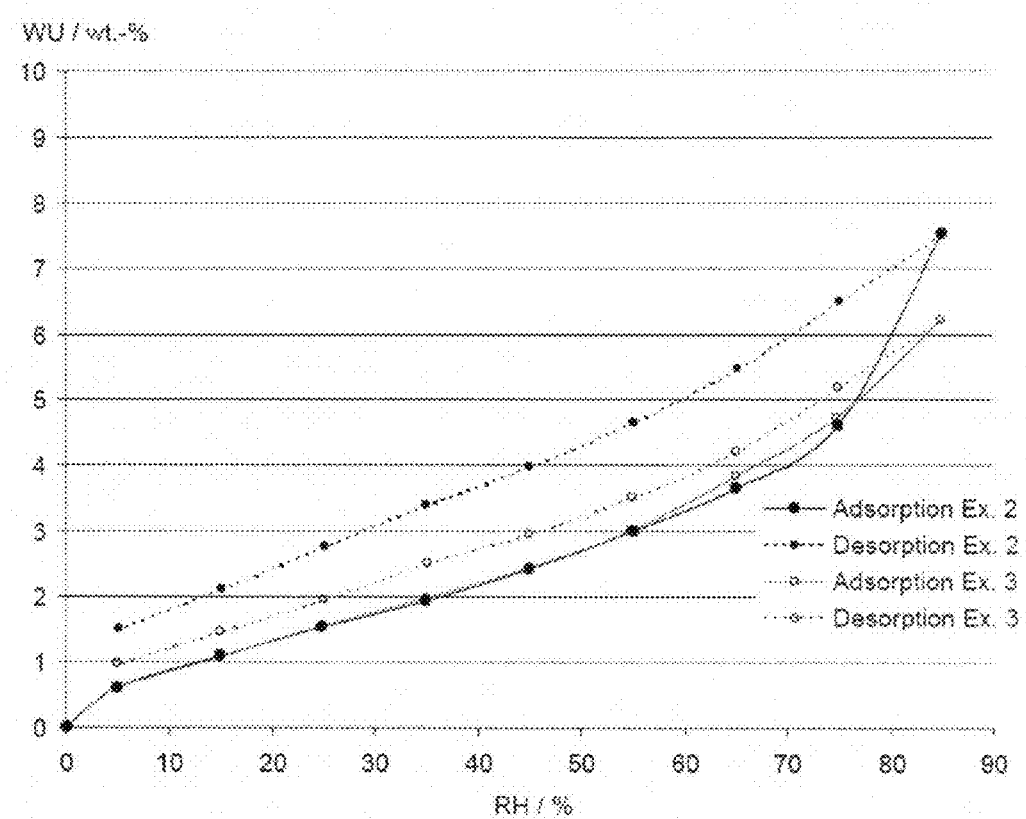

FIG. 13 shows the result of the water adsorption/desorption isotherms measurements of the moldings according to Example 2 and Example 3. On the x axis, the relative humidity (RH)/% is shown. On the y axis, the water uptake (WU) in weight-% is shown.

Figure 14:
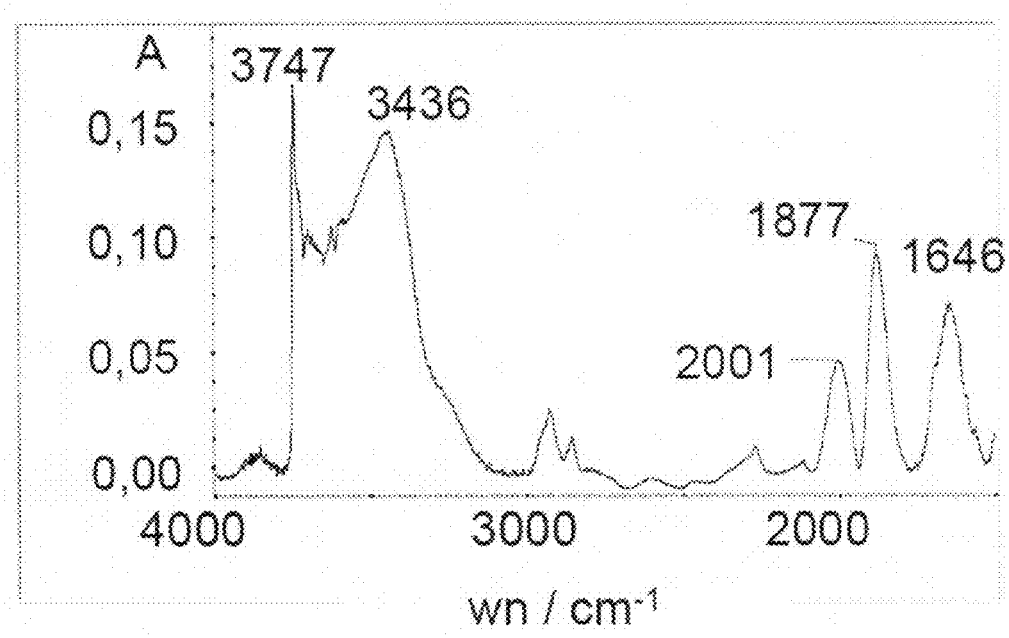

FIG. 14 shows the FT-IR spectrum of the sample of Example 2 (non-water-treated molding). The x axis shows the wavenumber (wn) in $cm^{-1}$, the y axis shows the absorbance (A).

Figure 15:
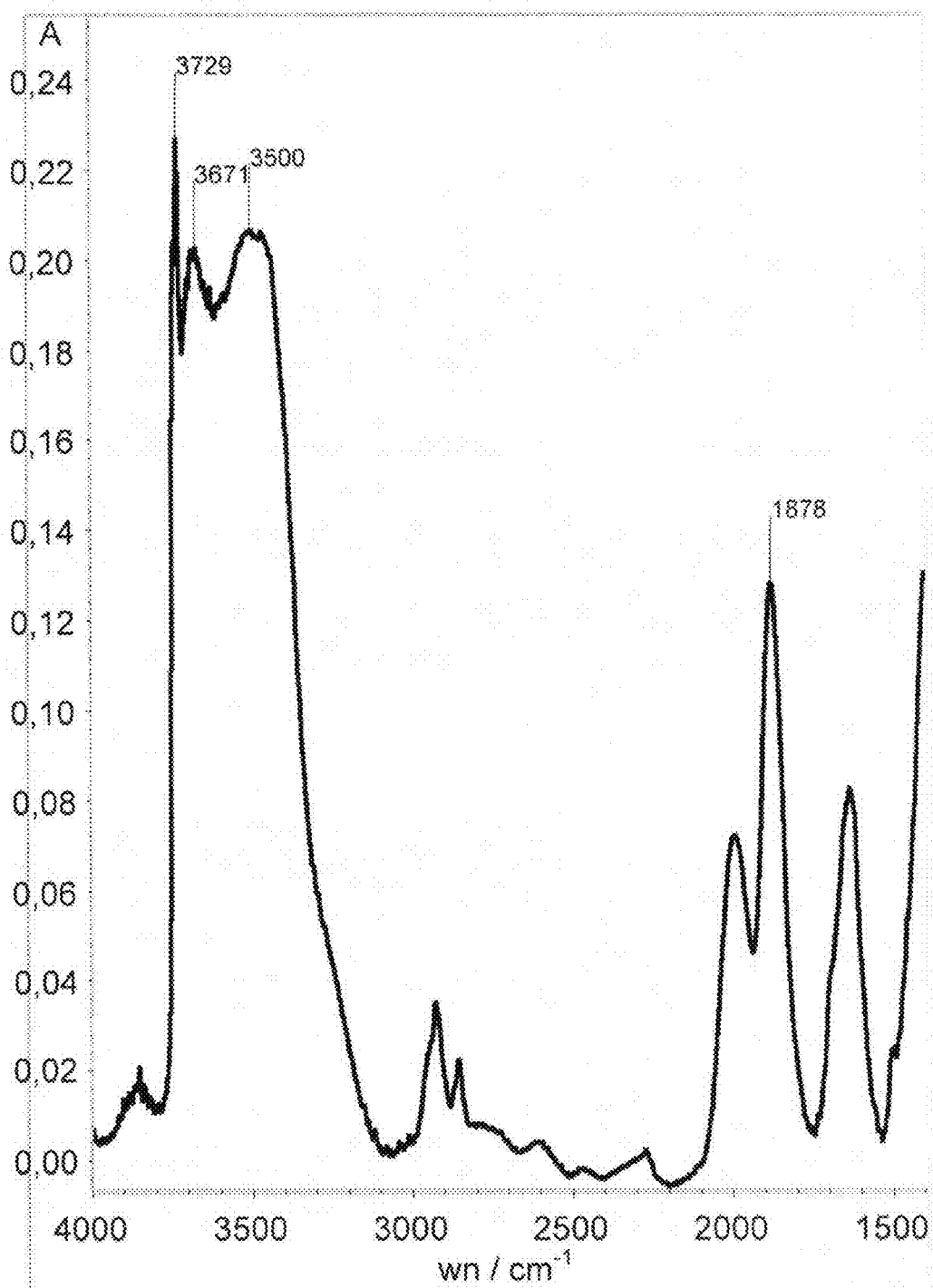

FIG. 15 shows the FT-IR spectrum of the sample of Example 3 (water-treated molding). The x axis shows the wavenumber (wn) in $cm^{-1}$, the y axis shows the absorbance (A).

Figure 16:
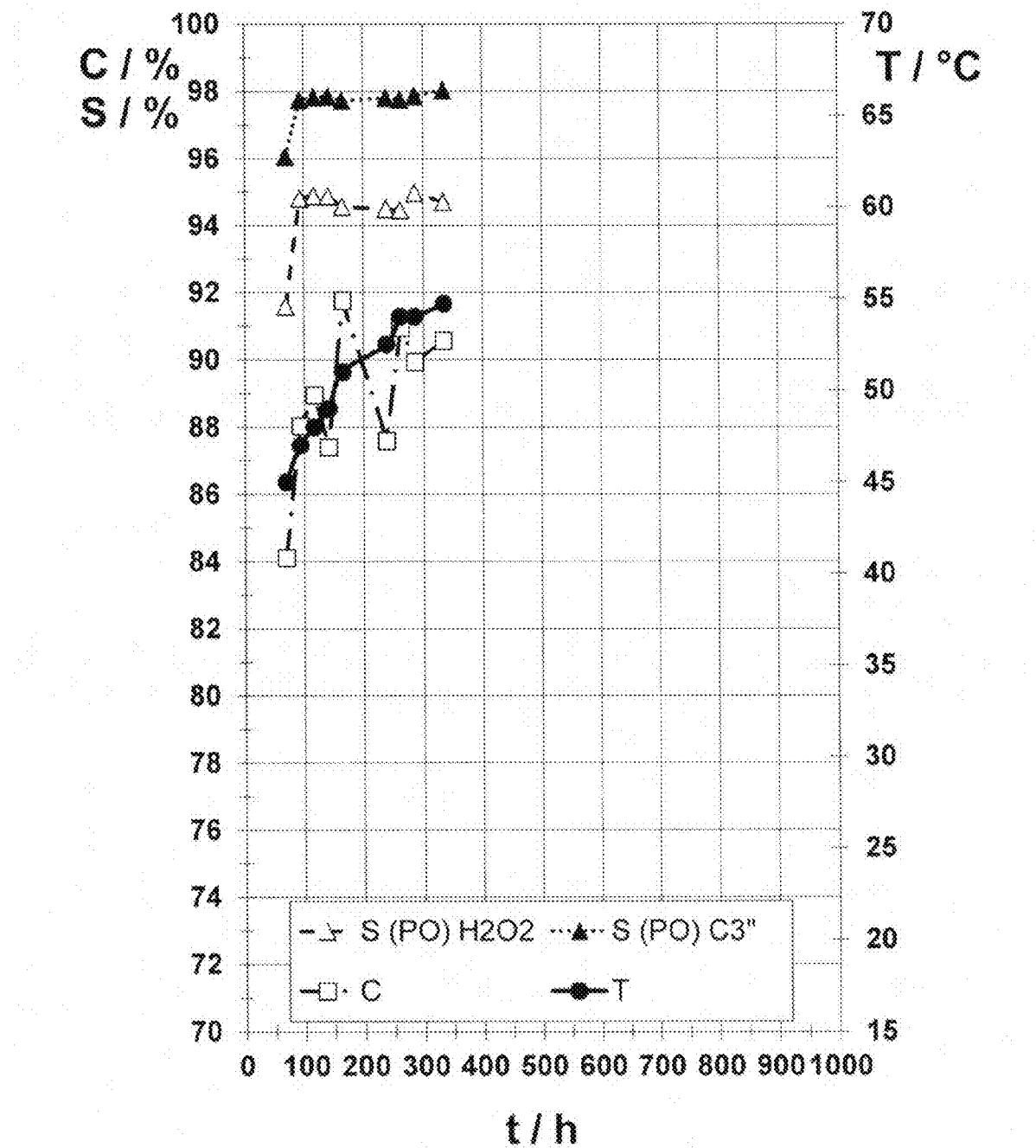

FIG. 16 shows the results of the continuous epoxidation reaction according to Example 2 in terms of the valuable product propylene oxide and the hydrogen peroxide conversion. The symbols FIG. 16 have the following meanings:
- S(PO)H2O2 in % (left y axis) (symbol: non-filled triangle) is the selectivity for propylene oxide based on $H_2O_2$ defined as moles of propylene oxide formed per unit time divided by moles of $H_2O_2$ consumed per unit time×100
- S(PO)C3" in % (left y axis) (symbol: filled triangle) is the selectivity for propylene oxide based on propylene defined as moles of propylene oxide formed per unit time divided by moles of propylene consumed per unit time×100
- C in % (left y axis) (symbol: non-filled square) is the conversion of $H_2O_2$ defined as moles of $H_2O_2$ consumed per unit time divided by moles of $H_2O_2$ fed to the reactor per unit time×100
- T in ° C. (right y axis) (symbol: filled circle) is the inlet temperature of the heat-transfer medium
- t in hours (x-axis) is the time on stream. The starting point (t=0) is taken as the time at which the $H_2O_2$ metering pump is started (all other pumps are started earlier)

Figure 17:
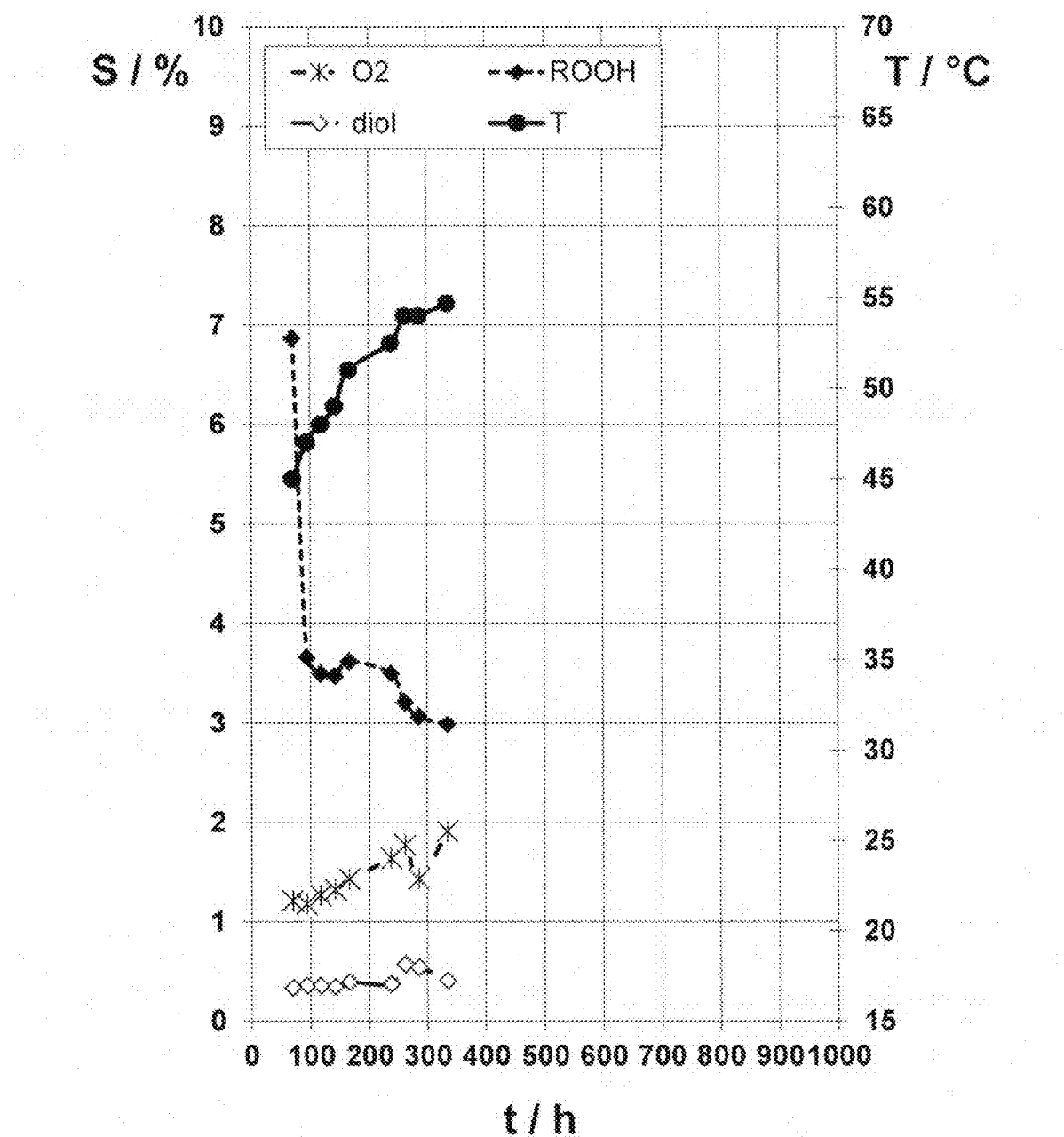

FIG. 17 shows the result of the continuous epoxidation reaction according to Example 2 in terms of the by-products oxygen, hydroperoxides, and diol. The symbols in FIG. 17 have the following meanings:
- O2 in % (left y axis) (symbol: star) is the selectivity for $O_2$ based on $H_2O_2$ defined as twice the number of moles of $O_2$ formed per unit time divided by the moles of $H_2O_2$ consumed per unit time×100
- ROOH in % (left y axis) (symbol: filled square) is the selectivity to hydroperoxypropanols based on $H_2O_2$ defined as twice the number of moles of hydroperoxypropanols formed per unit time divided by the moles of $H_2O_2$ consumed per unit time×100
- diol in % (left axis) (symbol: non-filled circle) is the selectivity to propylene glycol based on on $H_2O_2$ defined as the number of moles of propylene glycol formed per unit time divided by the moles of $H_2O_2$ consumed per unit time×100
- T in ° C. (right y axis) (symbol: filled circle) is the inlet temperature of the heat-transfer medium
- t in hours (x-axis) is the time on stream. The starting point (t=0) is taken as the time at which the $H_2O_2$ metering pump is started (all other pumps are started earlier)

Figure 18:
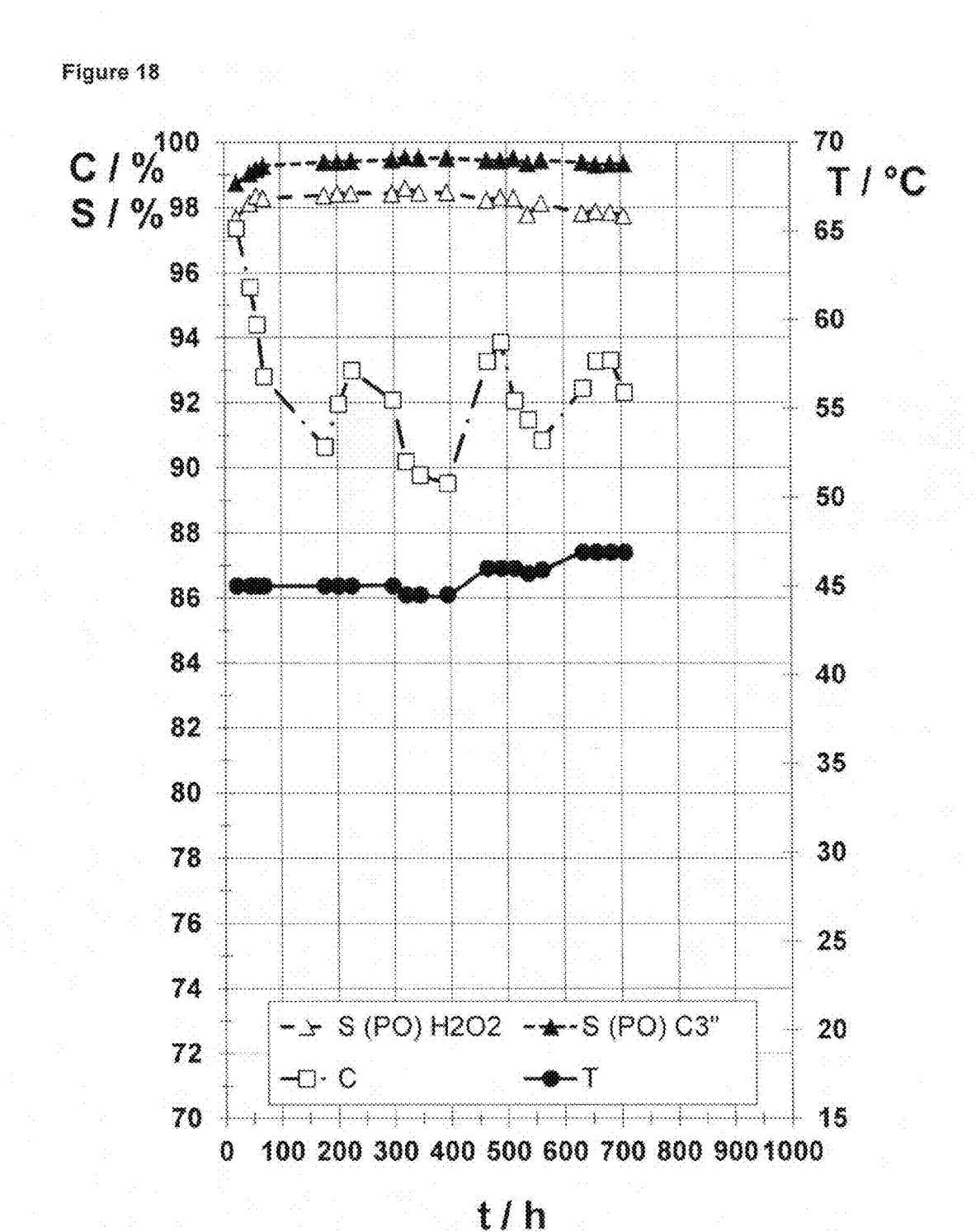

FIG. 18 shows the result of the continuous epoxidation reaction according to Example 3 in terms of the valuable product propylene oxide and the hydrogen peroxide conversion. The symbols FIG. 18 have the following meanings:
- S(PO)H2O2 in % (left y axis) (symbol: non-filled triangle) is the selectivity for propylene oxide based on $H_2O_2$ defined as moles of propylene oxide formed per unit time divided by moles of $H_2O_2$ consumed per unit time×100
- S(PO)C3" in % (left y axis) (symbol: filled triangle) is the selectivity for propylene oxide based on propylene defined as moles of propylene oxide formed per unit time divided by moles of propylene consumed per unit time×100
- C in % (left y axis) (symbol: non-filled square) is the conversion of $H_2O_2$ defined as moles of $H_2O_2$ consumed per unit time divided by moles of $H_2O_2$ fed to the reactor per unit time×100
- T in ° C. (right y axis) (symbol: filled circle) is the inlet temperature of the heat-transfer medium
- t in hours (x-axis) is the time on stream. The starting point (t=0) is taken as the time at which the $H_2O_2$ metering pump is started (all other pumps are started earlier)

Figure 19:
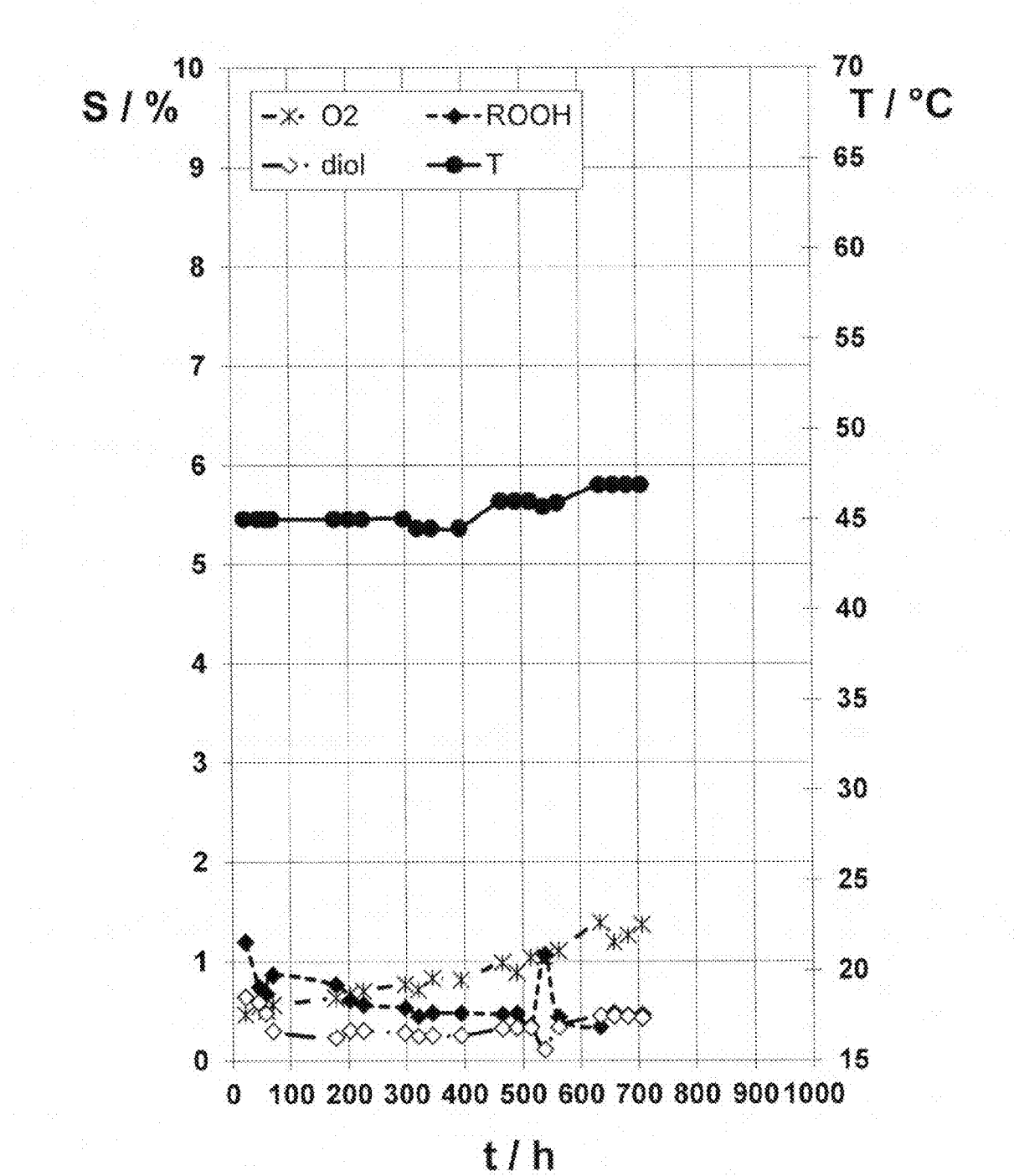

FIG. 19 shows the result of the continuous epoxidation reaction according to Example 3 in terms of the by-products oxygen, hydroperoxides, and diol. The symbols in FIG. 19 have the following meanings:
- O2 in % (left y axis) (symbol: star) is the selectivity for $O_2$ based on $H_2O_2$ defined as twice the number of moles of $O_2$ formed per unit time divided by the moles of $H_2O_2$ consumed per unit time×100
- ROOH in % (left y axis) (symbol: filled square) is the selectivity to hydroperoxypropanols based on $H_2O_2$ defined as twice the number of moles of hydroperoxypropanols formed per unit time divided by the moles of $H_2O_2$ consumed per unit time×100
- diol in % (left axis) (symbol: non-filled circle) is the selectivity to propylene glycol based on on $H_2O_2$ defined as the number of moles of propylene glycol formed per unit time divided by the moles of $H_2O_2$ consumed per unit time×100
- T in ° C. (right y axis) (symbol: filled circle) is the inlet temperature of the heat-transfer medium
- t in hours (x-axis) is the time on stream. The starting point (t=0) is taken as the time at which the $H_2O_2$ metering pump is started (all other pumps are started earlier)

Figure 20:
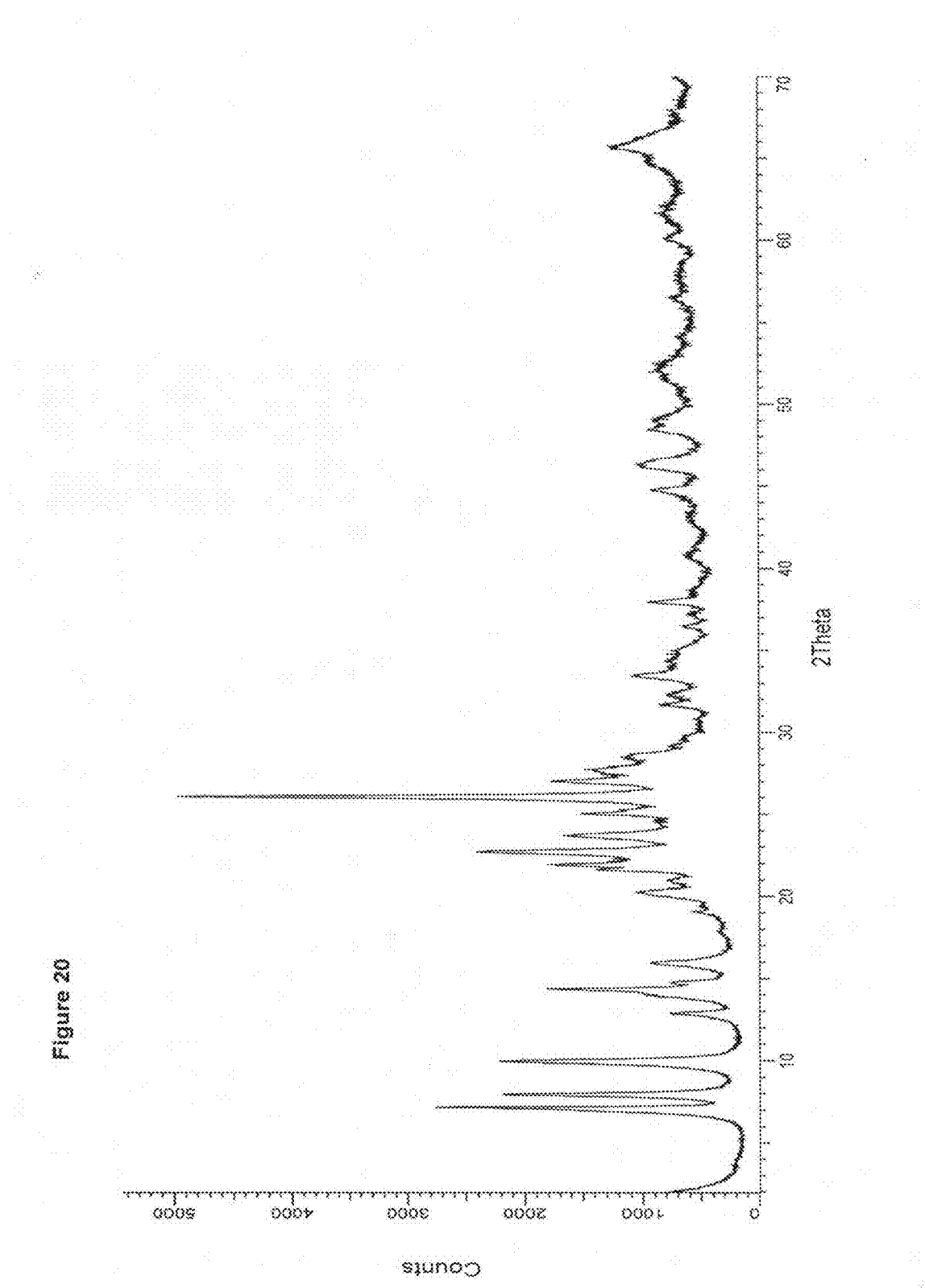

FIG. 20 shows the X-ray diffraction pattern (copper K alpha radiation) of the acid-treated, spray-dried and calcined ZnTiMWW micropowder as obtained according to Example 5.4. On the x axis, the degree values (2 Theta) are shown, on the y axis, the intensity (Lin (Counts)).

Figure 21:
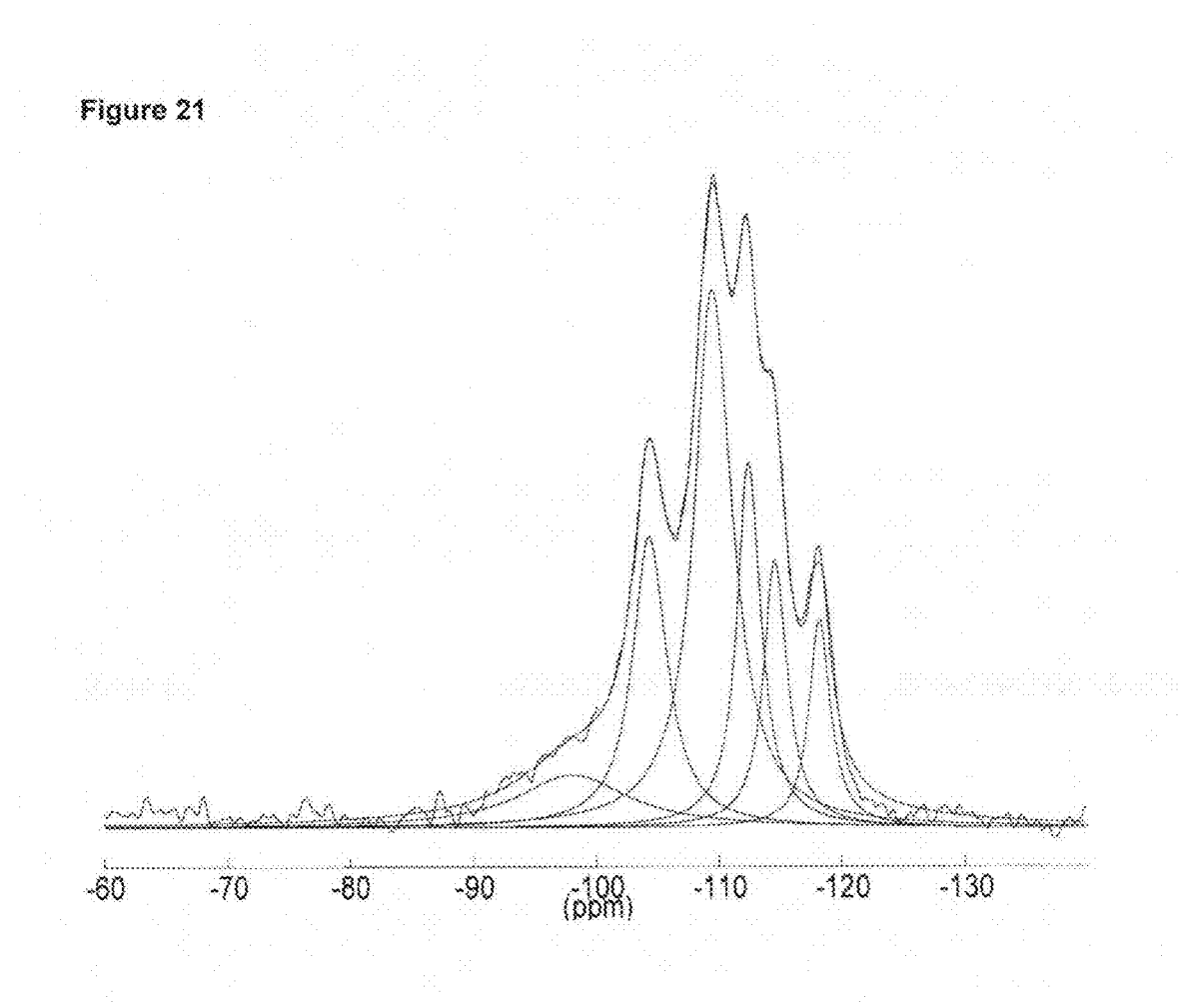

FIG. 21 shows the $^{29}Si$ MAS NMR spectrum of the material as obtained from Example 5.5. On the x axis, the shifts are shown in ppm. FIG. 21 additionally shows the six peaks obtained after having deconvolved by the proper Gaussian-Lorentzian line shapes.

Figure 22:
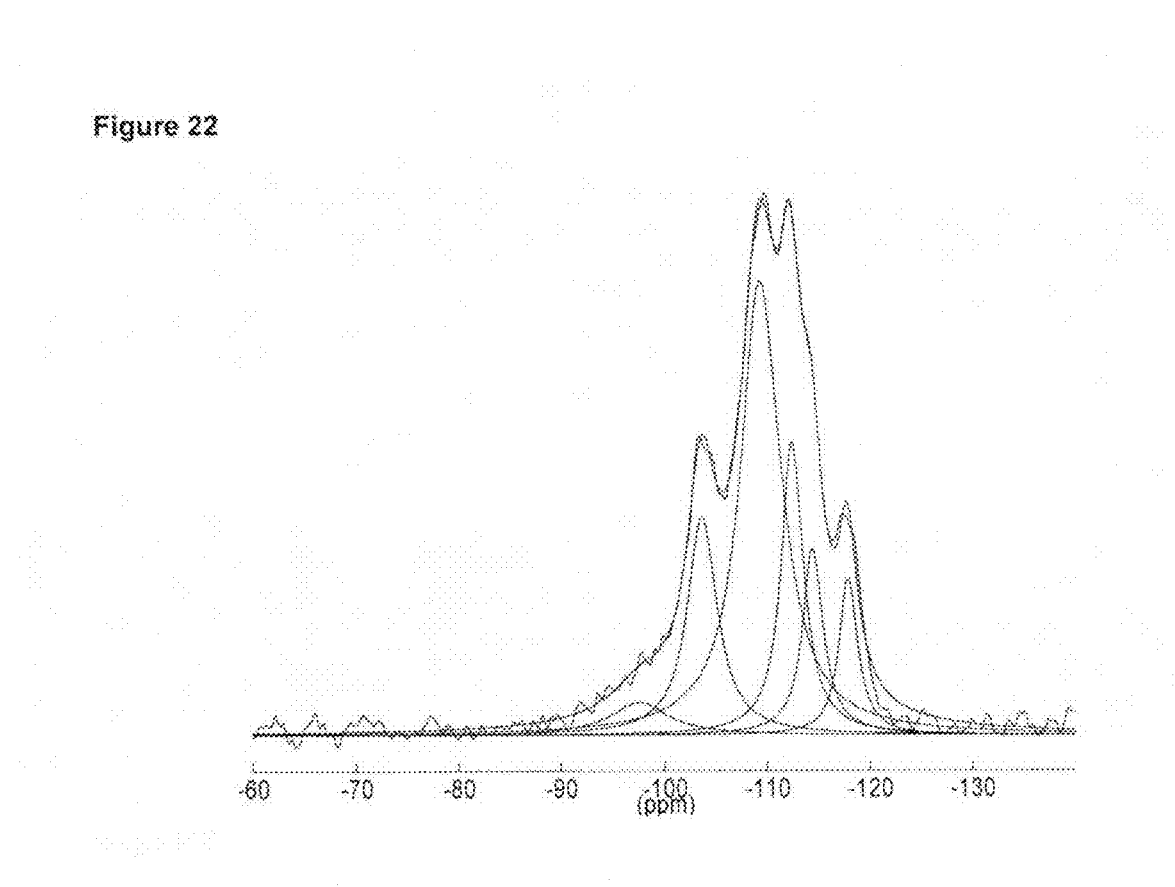

FIG. 22 shows the $^{29}Si$ MAS NMR spectrum of the material as obtained from Example 5.6. On the x axis, the shifts are shown in ppm. FIG. 22 additionally shows the six peaks obtained after having deconvolved by the proper Gaussian-Lorentzian line shapes.

Figure 23:
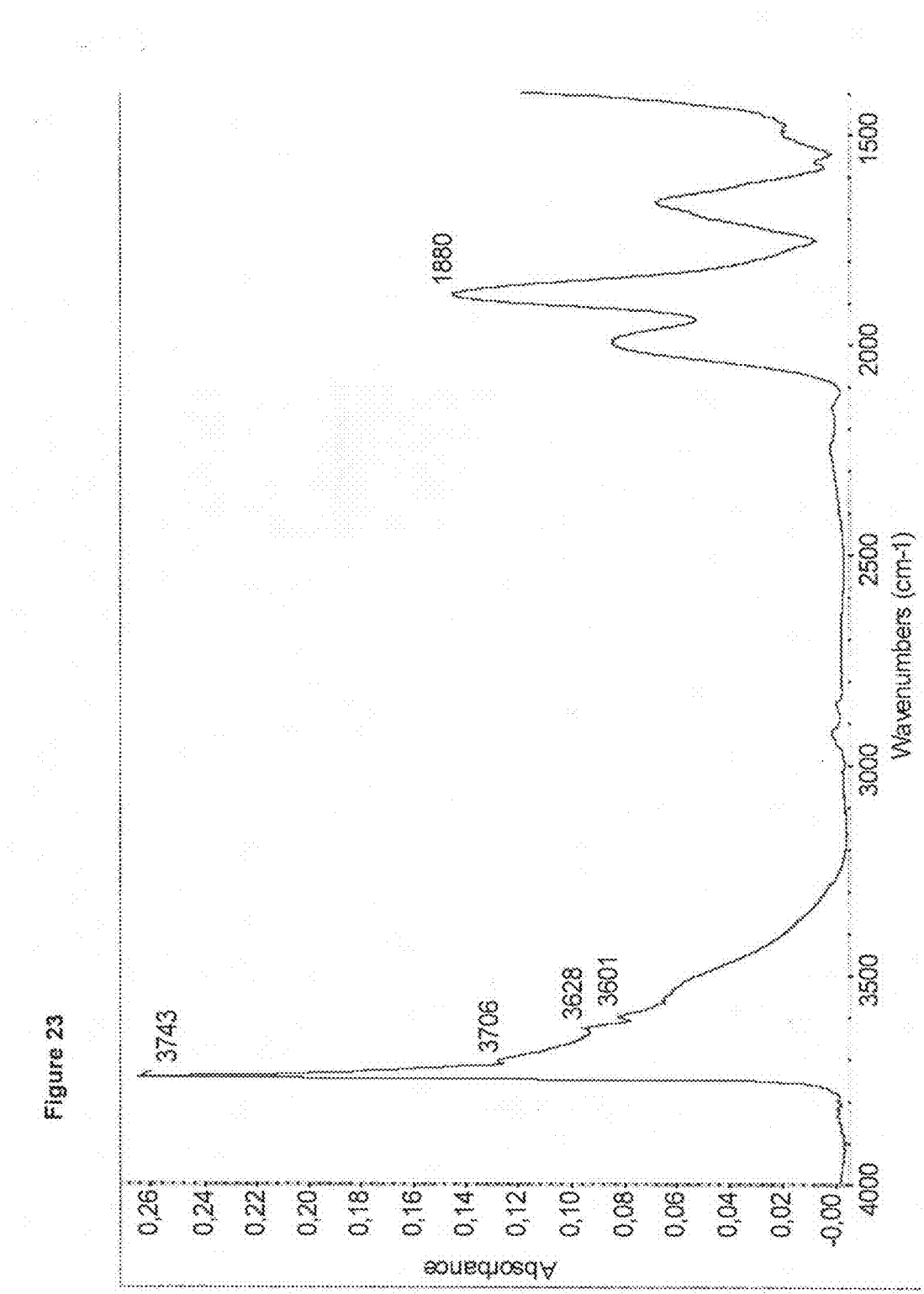

FIG. 23 shows the FT-IR spectrum of the sample of Example 5.5 (non-water-treated molding). The x axis shows the wavenumber (wn) in $cm^{-1}$, the y axis shows the absorbance (A).

Figure 24:
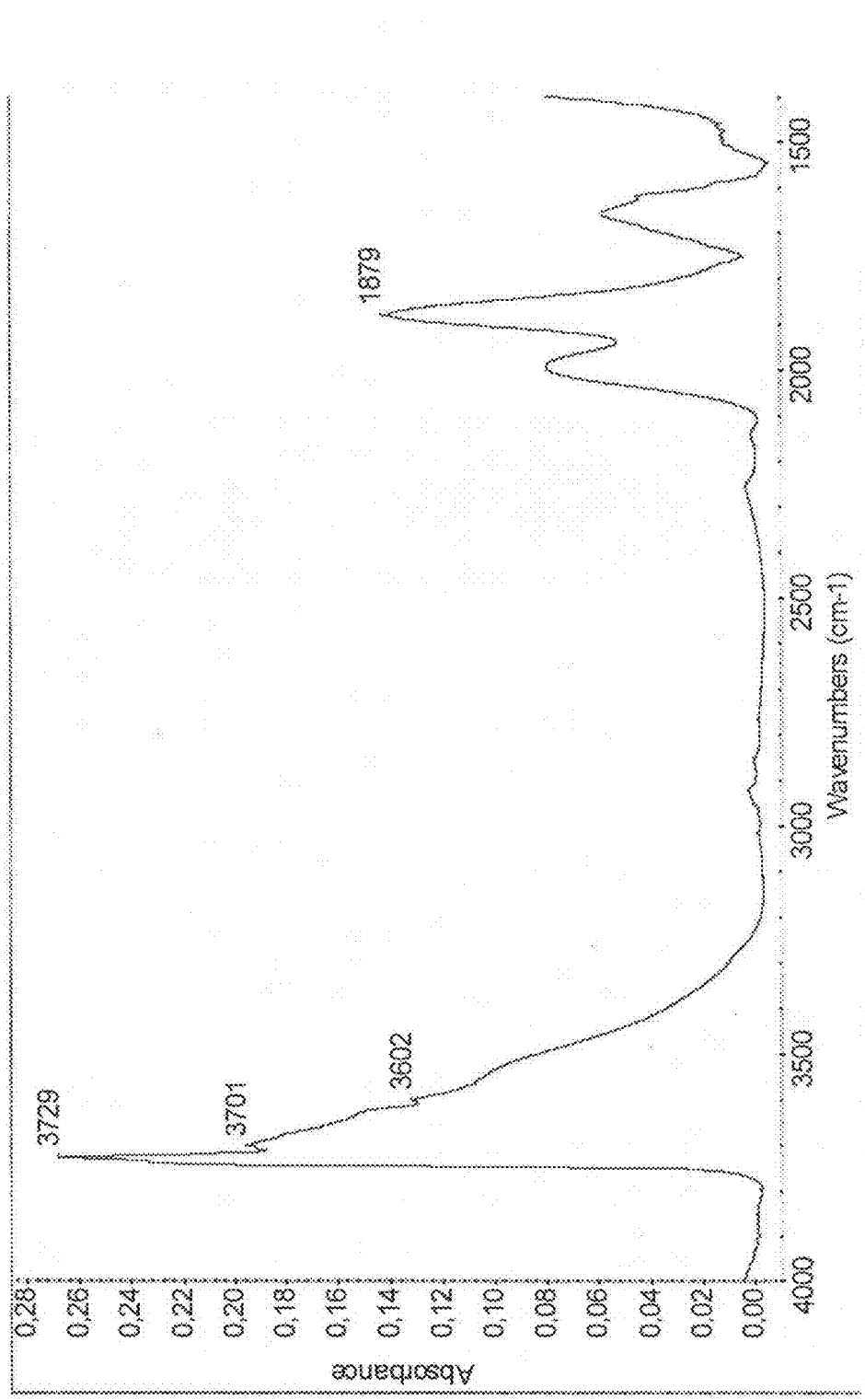

FIG. 24 shows the FT-IR spectrum of the sample of Example 5.6 (water-treated molding). The x axis shows the wavenumber (wn) in $cm^{-1}$, the y axis shows the absorbance (A).

Figure 25:
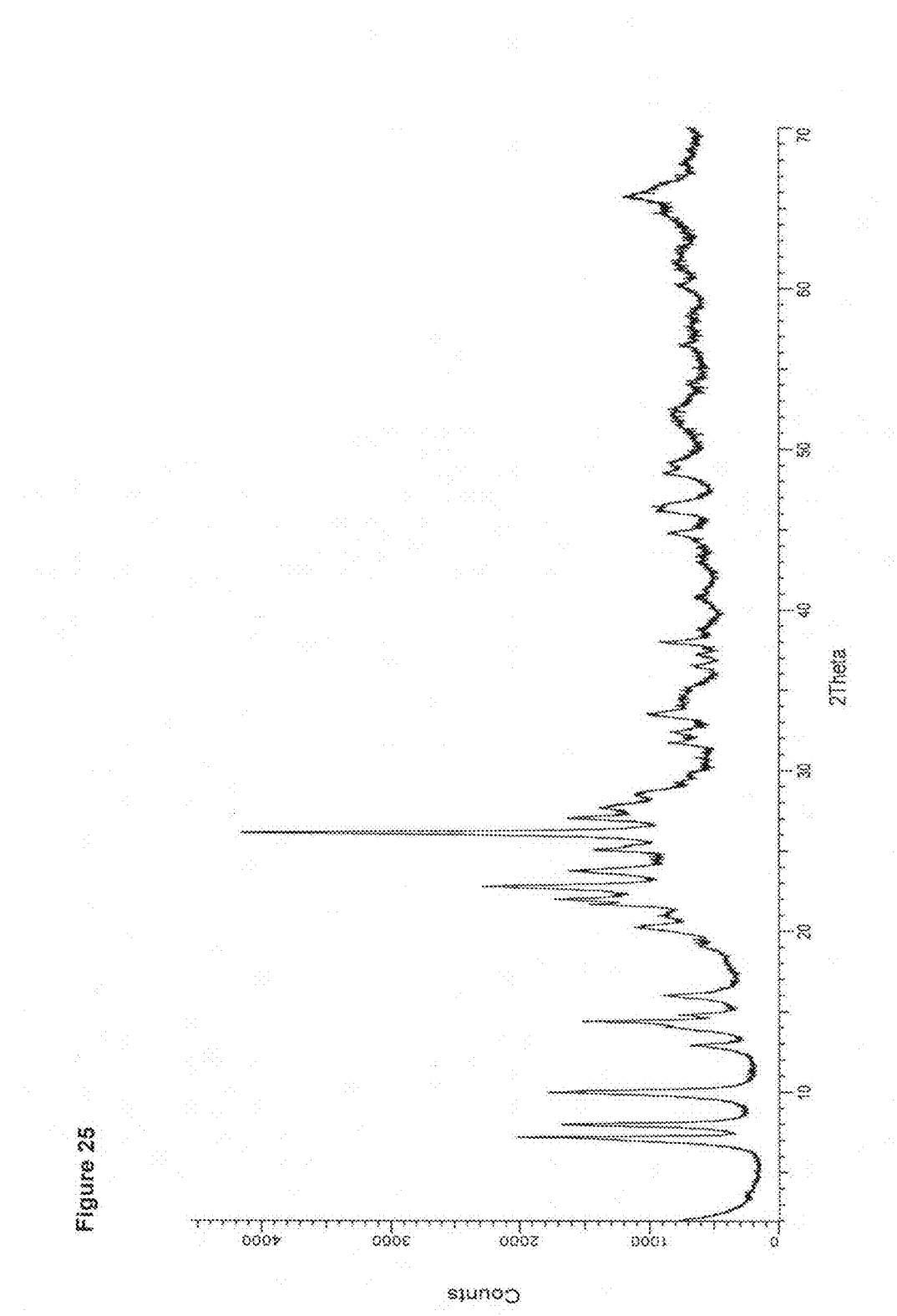

FIG. 25 shows the X-ray diffraction pattern (copper K alpha radiation) of the calcined molded ZnTiMWW material as obtained according to Example 5.5. On the x axis, the degree values (2 Theta) are shown, on the y axis, the intensity (Lin (Counts)

Figure 26:
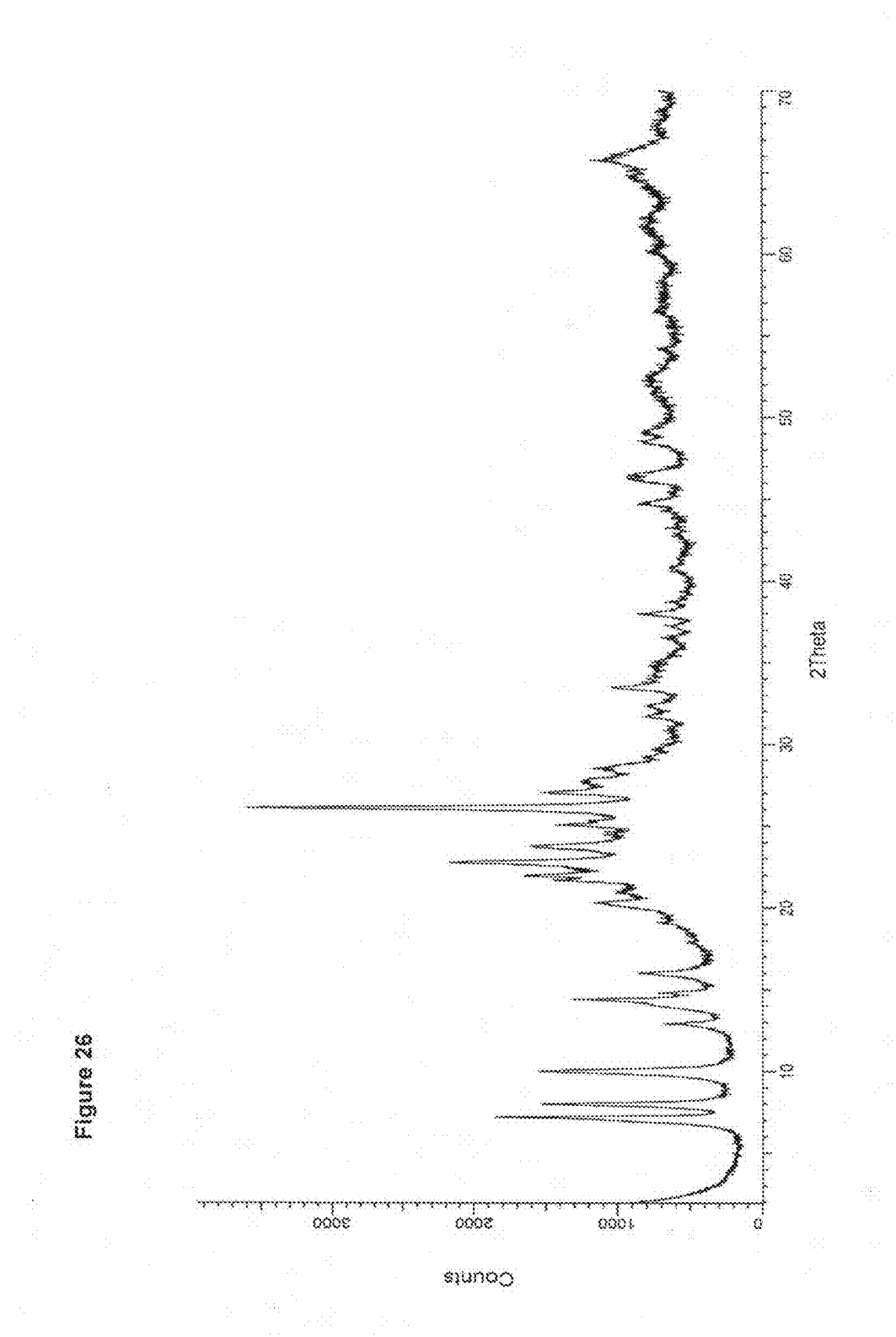

FIG. 26 shows the X-ray diffraction pattern (copper K alpha radiation) of the calcined and water-treated molded ZnTiMWW material as obtained according to Example 5.6.

On the x axis, the degree values (2 Theta) are shown, on the y axis, the intensity (Lin (Counts)

Figure 27:
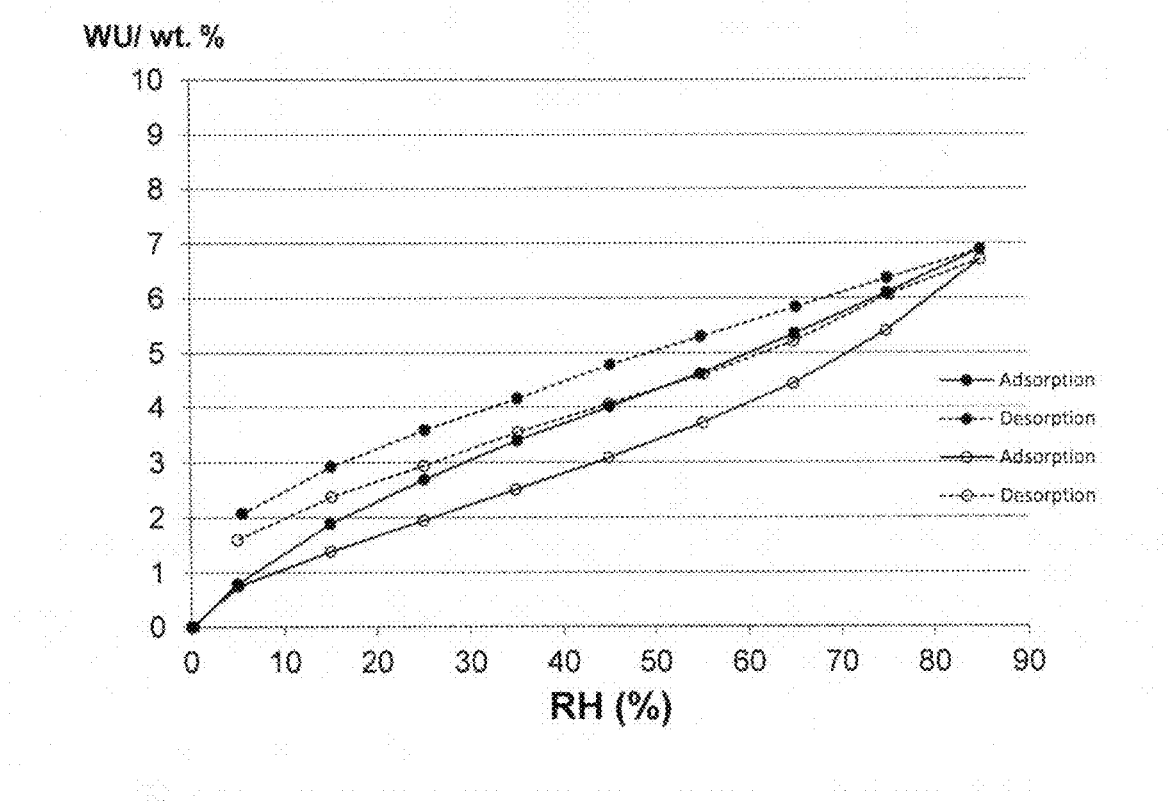

FIG. 27 shows the result of the water adsorption/desorption isotherms measurements of the moldings according to Example 5.5 (filled circles) and Example 5.6 (empty circles). On the x axis, the relative humidity (RH)/% is shown. On the y axis, the water uptake (WU) in weight-% is shown.

CITED LITERATURE

Chemistry Letters (2000) pp. 774-775
J. Phys. Chem. B 105 (2001) p. 2897
U.S. Pat. No. 6,759,540
U.S. Pat. No. 7,608,728
JP 2008-200553 A
U.S. Pat. No. 7,273,826
U.S. Pat. No. 7,476,770
U.S. Pat. No. 6,114,552

The invention claimed is:

1. A micropowder, the particles of which have a Dv10 value of at least 2 micrometer, said micropowder particles comprise mesopores having an average pore diameter 4V/A of from 2 to 50 nm as determined by Hg porosimetry according to DIN 66133, wherein V is the accumulated volume and A is the accumulated surface of the mesopores having an average pore diameter of from 2 to 50 nm;
wherein the micropowder comprises at least 95 weight %, based on the weight of the micropowder, of a microporous aluminum-free zeolitic material having structure type MWW comprising titanium and zinc.

2. The micropowder of claim 1,
wherein the micropowder particles have the Dv10 value of from 2 to 5.5 micrometer.

3. The micropowder of claim 1,
wherein the micropowder particles have the Dv50 value of from 7 to 25 micrometer.

4. The micropowder of claim 1,
wherein the mesopores have an average pore diameter 4V/A of from 10 to 50 nm, as determined by Hg porosimetry according to DIN 66133.

5. The micropowder of claim 1, additionally comprising macropores having an average pore diameter of more than 50 nm, as determined by Hg porosimetry according to DIN 66133.

6. The micropowder of claim 1,
wherein the micropores of the aluminum-free zeolitic material have an average pore diameter of from 1.0 to 1.2 nanometer as determined by nitrogen adsorption according to DIN 66135.

7. The micropowder of claim 1, comprising,
at least 99 weight %, based on the weight of the micropowder, of the aluminum-free zeolitic material.

8. The micropowder of claim 1,
wherein the aluminum-free zeolitic material comprises from 1.0 to 2.0 weight % of zinc, calculated as Zn and based on a weight of the aluminum-free zeolitic material.

9. The micropowder of claim 1,
wherein the aluminum-free zeolitic material comprises from 1.0 to 2.0 weight % of titanium, calculated as Ti and based on a weight of the aluminum-free zeolitic material.

10. The micropowder of claim 1, having a crystallinity, as determined by an X-ray diffraction analysis, of at least (80+/−10) %.

11. The micropowder of claim 1, comprising, based on the total weight of the micropowder and calculated as element: less than 0.001 weight % of a noble metal selected from the group consisting of gold, silver, platinum, palladium, iridium, ruthenium, osmium, and a mixture thereof.

12. The micropowder of claim 1, comprising, based on the total weight of the micropowder and calculated as element, less than 0.1 weight % of boron.

13. The micropowder of claim 1, having a bulk density of from 80 to 100 g/ml.

14. The micropowder of claim 1, wherein the micropowder is a spray powder.

15. The micropowder of claim 1, wherein the micropowder is comprised in a molding, and said molding additionally comprises a binder.

16. The micropowder of claim 1, wherein the micropowder is suitable for a catalyst, or as an intermediate for preparation of a catalyst.

17. The micropowder of claim 1,
wherein the micropowder particles have the Dv10 value of from 3 to 5.5 micrometer.

18. A process comprising
(i) providing a suspension containing a microporous aluminum-free zeolitic material of structure type MWW containing titanium and zinc (ZnTiMWW);
(ii) subjecting the suspension provided in (i) to spray-drying to obtain a micropowder;
(iii) calcining the micropowder obtained in (ii), wherein the micropowder obtained in (iii) is the micropowder according to claim 1.

19. The process of claim 18, wherein the suspension provided in (i) has a solid content in the range of from 5 to 25 weight-%, the suspension being an aqueous suspension.

20. The process of claim 18, wherein the ZnTiMWW according to (i) contains zinc in an amount of from 1.0 to 2.0 weight-%, calculated as Zn, and titanium in an amount of from 1.0 to 2.0 weight-%, calculated as Ti, based on the weight of the ZnTiMWW.

21. The process of claim 18, wherein in (ii), a spray-apparatus is used for spray-drying the suspension, said apparatus having at least one spray-nozzle having a diameter in the range of from 3.5 to 4.5 mm.

22. The process of claim 18, wherein in (ii), a spray-apparatus is used for spray-drying the suspension, said apparatus being operated with a nozzle gas having a temperature in the range of from 20 to 50° C., and a drying gas having a temperature in the range of from 250 to 350° C., said nozzle gas being an inert gas.

23. The process of claim 22, wherein in (iii), the micropowder is calcined at a temperature in the range of from 600 to 700° C. for a duration in the range of from 0.5 to 6 h.

24. The process of claim 22 wherein said drying gas is an inert gas.

25. The process of claim 18, further comprising
(iv) shaping the micropowder obtained in (iii) to obtain a molding;
(v) optionally drying and/or calcining the molding obtained in (iv).

26. The process of claim 25, wherein the shaping according to (iv) comprises
(aa) mixing the micropowder with a silica binder or a silica binder precursor,
wherein the weight ratio of the ZnTiMWW contained in the micropowder relative to silica contained in or resulting from the silica binder is in the range of from 3:7 to 1:4, to obtain a mixture;
(bb) shaping the mixture obtained in (aa) to obtain the molding, said shaping comprising subjecting the mixture obtained in (aa) to extrusion from which strands are obtained having a diameter in the range of from 1.0 to 2.0 mm.

27. The process of claim 26, wherein in (aa), a carbohydrate and/or water is/are added as pasting agent.

28. The process of claim 26, wherein the mixing in (aa) is carried out for a duration in the range of from 15 to 60 min.

29. The process of claim 25, wherein in (iv), no mesopore-forming agent selected from the group consisting of polyalkylene oxides such as polyethylene oxides, polystyrene, polyacrylates, polymethacrylates, polyolefins, polyamides, and polyesters is added.

30. The process of claim 25, wherein in (v), the molding is dried at a temperature in the range of from 100 to 150° C. for a duration in the range of from 10 to 20 h and calcined at a temperature in the range of from 500 to 600° C. for a duration in the range of from 0.5 to 2 h.

31. The process of claim 25, further comprising
(vi) subjecting the molding obtained in (iv) or (v) to a water-treatment;
(vii) optionally drying and/or calcining the water-treated molding.

32. The process of claim 31 wherein the molding obtained in (vi) or (vii) comprises a microporous aluminum-free zeolitic material of the structure type MWW containing titanium and zinc.

33. The process of claim 31, wherein in (vi), the water-treatment comprises treating the molding with liquid water in an autoclave under autogenous pressure at a temperature in the range of from 100 to 200° C. for a period of from 2 to 24 hours.

34. The process of claim 31, wherein in (vi), the weight ratio of the molding relative to the water is in the range of from 0.02 to 0.08.

35. The process of claim 31, wherein in (vii), the water-treated molding is dried at a temperature in the range of from 100 to 150° C. for a duration in the range of from 10 to 20 h and calcined
at a temperature in the range of from 400 to 500° C. for a duration in the range of from 1 to 3 h.

36. The process of claim 25, wherein the molding is not subjected to steaming.

37. A micropowder, obtained by the process according to claim 18.

* * * * *